(12) United States Patent
Bindschaedler et al.

(10) Patent No.: US 9,968,087 B2
(45) Date of Patent: May 15, 2018

(54) AZOLINE COMPOUNDS

(71) Applicant: BASF SE, Ludwigshafen (DE)

(72) Inventors: Pascal Bindschaedler, Roemerberg (DE); Wolfgang Von Deyn, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/121,493

(22) PCT Filed: Feb. 25, 2015

(86) PCT No.: PCT/EP2015/053899
§ 371 (c)(1),
(2) Date: Aug. 25, 2016

(87) PCT Pub. No.: WO2015/128358
PCT Pub. Date: Sep. 3, 2015

(65) Prior Publication Data
US 2016/0366887 A1    Dec. 22, 2016

Related U.S. Application Data

(60) Provisional application No. 62/094,091, filed on Dec. 19, 2014, provisional application No. 61/944,588, filed on Feb. 26, 2014.

(51) Int. Cl.

| | | |
|---|---|---|
| A01N 43/80 | (2006.01) |
| C07D 413/12 | (2006.01) |
| A01N 43/78 | (2006.01) |
| C07D 417/12 | (2006.01) |
| A01N 43/54 | (2006.01) |
| C07D 207/20 | (2006.01) |
| A01N 43/36 | (2006.01) |
| C07D 409/12 | (2006.01) |
| C07D 401/12 | (2006.01) |
| C07D 261/04 | (2006.01) |
| A01N 43/82 | (2006.01) |
| A01N 43/40 | (2006.01) |
| C07D 263/16 | (2006.01) |
| C07D 207/22 | (2006.01) |

(52) U.S. Cl.
CPC ............ *A01N 43/80* (2013.01); *A01N 43/36* (2013.01); *A01N 43/40* (2013.01); *A01N 43/54* (2013.01); *A01N 43/78* (2013.01); *A01N 43/82* (2013.01); *C07D 207/20* (2013.01); *C07D 207/22* (2013.01); *C07D 261/04* (2013.01); *C07D 263/16* (2013.01); *C07D 401/12* (2013.01); *C07D 409/12* (2013.01); *C07D 413/12* (2013.01); *C07D 417/12* (2013.01)

(58) Field of Classification Search
None
See application file for complete search history.

(56) References Cited

U.S. PATENT DOCUMENTS 8,410,153 B2 *  4/2013  Lahm .................. C07D 261/04
                                                514/378

FOREIGN PATENT DOCUMENTS

| EP | 1731512 | 12/2006 |
|---|---|---|
| EP | 1932836 | 6/2008 |
| EP | 2172448 | 4/2010 |
| JP | 2007091708 | 4/2007 |
| JP | 2008133273 | 6/2008 |
| WO | WO-2009/080250 | 7/2009 |
| WO | WO-2010/020522 | 2/2010 |
| WO | WO-2010/149506 | 12/2010 |
| WO | WO-2011/067272 | 6/2011 |
| WO | WO-2011/073444 | 6/2011 |
| WO | WO-2011/161130 | 12/2011 |
| WO | WO-2012/007426 | 1/2012 |
| WO | WO-2012/163959 | 12/2012 |
| WO | WO-2013/026929 | 2/2013 |
| WO | WO-2014/019951 | 2/2014 |

OTHER PUBLICATIONS

International Search Report for PCT/EP2015/053899 dated Apr. 29, 2015.
International Preliminary Report on Patentability for PCT/EP2015/053899 dated Sep. 9, 2016.

* cited by examiner

*Primary Examiner* — Kamal Saeed
(74) *Attorney, Agent, or Firm* — Brinks Gilson & Lione

(57) ABSTRACT

The present invention relates to azoline compounds of formula I

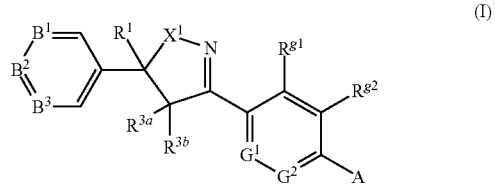

(I)

wherein A, $B^1$, $B^2$, $B^3$, $G^1$, $G^2$, $X^1$, $R^1$, $R^{3a}$, $R^{3b}$, $R^{g1}$ and $R^{g2}$ are as defined in the claims and the description. The compounds are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

23 Claims, No Drawings

AZOLINE COMPOUNDS

This application is a National Stage application of International Application No. PCT/EP2015/053899, filed Feb. 25, 2015, which claims the benefit of U.S. Provisional Application No. 62/094,091, filed Dec. 19, 2014 and U.S. Provisional Application No. 61/944,588, filed Feb. 26, 2014.

The present invention relates to azoline compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

Related compounds are described in WO 2013/026929, WO 2012/163959, WO 2012/007426, WO 2011/067272, WO 2010/149506, WO 2010/020522, WO 2009/080250, EP-A-1731512, JP-A-2007091708 and JP-A-2008133273. However, these documents do not describe compounds having the characteristic substituents and substituents' arrangement as claimed in the present invention.

It is an object of the present invention to provide compounds that have a good pesticidal activity, in particular insecticidal activity, and show a broad activity spectrum against a large number of different invertebrate pests, especially against difficult to control arthropod pests and/or nematodes.

The object of the present invention is moreover to provide compounds which are less persistent, bioaccumulative and/or toxic than the compounds of the prior art. Especially isoxazoline insecticides of the prior art show a high persistency in the soil and thus accumulate there.

It has been found that these objectives can be achieved by azoline compounds of the formula I below, by their stereoisomers and by their salts, in particular their agriculturally or veterinarily acceptable salts.

Therefore, in a first aspect, the invention relates to azoline compounds of the formula I

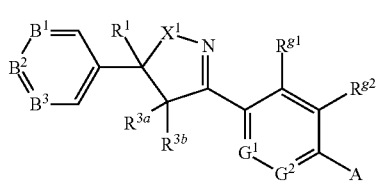
(I)

wherein
$X^1$ is O or $CH_2$;
A is a group of following formula:

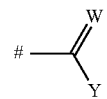
(A)

wherein
# denotes the bond to the aromatic ring of formula (I);
W is selected from O and S;
Y is selected from hydrogen, $-N(R^5)R^6$ and $-OR^9$;
$B^1$, $B^2$ and $B^3$ are each independently selected from the group consisting of N and $CR^2$, with the proviso that at most two of $B^1$, $B^2$ and $B^3$ are N;
$G^1$ and $G^2$ are each independently selected from the group consisting of N and $CR^4$, with the proviso that at most one of G1 and $G^2$ is N;
$R^{g1}$ and $R^{g2}$ form together a bridging group selected from $-CH_2CH_2CH_2CH_2-$ and $-CH_2CH_2CH_2-$;
$R^1$ is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl-, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and $-C(=O)OR^{15}$;
each $R^2$ is independently selected from the group consisting of hydrogen, halogen, cyano, azido, nitro, $-SCN$, $-SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$,
$-Si(R^{12})_3$, $-OR^9$, $-S(O)_nR^9$ and $-NR^{10a}R^{10b}$;
$R^{3a}$, $R^{3b}$ are each independently selected from the group consisting of hydrogen, halogen, hydroxyl, $-CO_2R^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group $=O$, $=C(R^{3c})_2$, $=NOH$ or $=NOCH_3$;
each $R^{3c}$ is independently selected from the group consisting of hydrogen, halogen, $CH_3$ and $CF_3$;
$R^{3d}$ is selected from the group consisting of hydrogen, $C_1$-$C_6$-alkyl and $C_1$-$C_3$-alkyloxy-$C_1$-$C_3$-alkyl-;
each $R^4$ is independently selected from the group consisting of hydrogen, halogen, cyano, azido, nitro, $-SCN$, $-SF_5$, $C_1$-$C_6$-alkyl which may be partially or fully halogenated and/or may be substituted by one or more radicals $R^8$, $C_3$-$C_8$-cycloalkyl which may be partially or fully halogenated and/or may be substituted by one or more radicals $R^8$, $C_2$-$C_6$-alkenyl which may be partially or fully halogenated and/or may be substituted by one or more radicals $R^8$, $C_2$-$C_6$-alkynyl which may be partially or fully halogenated and/or may be substituted by one or more radicals $R^8$,
$-Si(R^{12})_3$, $-OR^9$, $-S(O)_nR^9$, and $-NR^{10a}R^{10b}$;
each $R^5$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$; and
each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$,
$-OR^9$, $-NR^{10a}R^{10b}$; $-C(=O)NR^{10a}N(R^{10a})R^{10b}$, $-Si(R^{12})_3$, $-C(=O)R^8$, $-CH=NOR^9$,
phenyl which may be substituted with 1, 2, 3, 4, or 5 substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;

or $R^5$ and $R^6$ together form a group =$C(R^8)_2$, =$S(O)_m(R^9)_2$, =$NR^{10a}$ or =$NOR^9$;

each $R^8$ is independently selected from the group consisting of cyano, azido, nitro, —SCN, —$SF_5$, $C_3$-$C_8$-cycloalkyl, $C_3$-$C_8$-halocycloalkyl, where the cycloaliphatic moieties in the two last-mentioned radicals may be substituted by one or more radicals $R^{13}$;

—$Si(R^{12})_3$, —$OR^9$, —$OSO_2R^9$, —$S(O)_nR^9$, —$N(R^{10a})R^{10b}$, —C(=O)N($R^{10a}$)$R^{10b}$, —C(=S)N($R^{10a}$)$R^{10b}$, —C(=O)$R^9$, —CH=$NOR^9$, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =C($R^{13}$)$_2$; =S; =$S(O)_m(R^{15})_2$, =$S(O)_mR^{15}$N($R^{14a}$)$R^{14b}$, =$NR^{10a}$, =$NOR^9$; or =NN($R^{10a}$)$R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and $SO_2$, as ring members, and where the carbocyclic or heterocyclic ring is optionally substituted with one or more substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more radicals $R^{13}$; and $R^8$ in the groups —C(=O)$R^8$ and =$C(R^8)_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$, —$C_1$-$C_6$-alkyl-C(=O)$OR^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=$NR^{14}$)N($R^{14a}$)$R^{14b}$, —$Si(R^{12})_3$, —$S(O)_nR^{15}$, —$S(O)_nN(R^{14a})R^{14b}$, —$N(R^{10a})R^{10b}$, —N=C($R^{13}$)$_2$, —C(=O)$R^{13}$, —C(=O)N($R^{14a}$)$R^{14b}$, —C(=S)N($R^{14a}$)$R^{14b}$, —C(=O)$R^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$; and $R^9$ in the groups —$S(O)_nR^9$ and —$OSO_2R^9$ is additionally selected from the group consisting of $C_1$-$C_6$-alkoxy and $C_1$-$C_6$-haloalkoxy;

$R^{10a}$, $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$;

—$C_1$-$C_6$-alkyl-C(=O)$OR^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=$NR^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio, —$S(O)_nR^{15}$, —$S(O)_nN(R^{14a})R^{14b}$, —C(=O)$R^{13}$, —C(=O)$OR^{15}$, —C(=O)N($R^{14a}$)$R^{14b}$, —C(=S)$R^{13}$, —C(=S)$SR^{15}$, —C(=S)N($R^{14a}$)$R^{14b}$, —C(=$NR^{14}$)$R^{13}$;

phenyl, optionally substituted with 1, 2, 3, 4 or 5 substituents $R^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more substituents $R^{16}$;

or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and $SO_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5 substituents $R^{16}$, and a 3-, 4-, 5-, 6,- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring optionally carries one or more substituents $R^{16}$;

or $R^{10a}$ and $R^{10b}$ together form a group $=C(R^{13})_2$, $=S(O)_m(R^{15})_2$, $=S(O)_mR^{15}N(R^{14a})R^{14b}$, $=NR^{14}$ or $=NOR^{15}$;

$R^{11}$ is independently selected from the group consisting of halogen, cyano, azido, nitro, —SCN, —$SF_5$, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more radicals $R^8$, —$OR^9$, —$NR^{10a}R^{10b}$, —$S(O)_nR^9$, —$Si(R^{12})_3$;

phenyl, optionally substituted with 1, 2, 3, 4, or 5 substituents selected independently from $R^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and $SO_2$, as ring members, where the heterocyclic ring is optionally substituted with one or more substituents selected independently from $R^{16}$;

or two $R^{11}$ present on the same ring carbon atom of an unsaturated or partially unsaturated heterocyclic ring may together form a group $=O$, $=C(R^{13})_2$; $=S$; $=S(O)_m(R^{15})_2$; $=S(O)_mR^{15}N(R^{14a})R^{14b}$, $=NR^{14}$, $=NOR^{15}$, or $=NN(R^{14a})R^{14b}$;

or two $R^{11}$ present on the same S or SO ring member of a heterocyclic ring may together form a group $=NR^{14}$, $=NOR^{15}$, or $=NN(R^{14a})R^{14b}$;

or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from C=O, C=S and C=$NR^{14}$ as ring members, and wherein the ring may be substituted by one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5 substituents $R^{16}$;

each $R^{13}$ is independently selected from the group consisting of cyano, nitro, —OH, —SH, —SCN, —$SF_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, —C(=O)N($R^{14a}$)$R^{14b}$, $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted or carry 1, 2, 3, 4 or 5 substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by 1, 2 or 3 substituents $R^{16}$;

or two $R^{13}$ present on the same carbon atom of an alkyl, alkenyl, alkynyl or cycloalkyl group may together be $=O$, $=CH(C_1$-$C_4$-alkyl), $=C(C_1$-$C_4$-alkyl)$C_1$-$C_4$-alkyl, $=N(C_1$-$C_6$-alkyl) or $=NO(C_1$-$C_6$-alkyl);

and $R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo;

and $R^{13}$ in the groups $=C(R^{13})_2$, —N=$C(R^{13})_2$, —C(=O)$R^{13}$, —C(=S)$R^{13}$ and —C(=$NR^{14}$)$R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_6$-cycloalkyl which may be substituted by 1 or 2 substituents selected from halogen and cyano; and oxo;

$C_3$-$C_8$-cycloalkyl which may be unsubstituted, partially or fully halogenated and/or may carry 1 or 2 radicals selected from cyano, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano; and oxo;

phenyl, benzyl, pyridyl, phenoxy, wherein the cyclic moieties in the four last-mentioned radicals may be unsubstituted and/or carry 1, 2, 3 or 4 substituents selected from halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and ($C_1$-$C_6$-alkoxy)carbonyl; and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$;

$R^{14a}$ and $R^{14b}$, independently of each other, have one of the meanings given for $R^{14}$;

or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

or $R^{14a}$ and $R^{14}$ or $R^{14b}$ and $R^{14}$, together with the nitrogen atoms to which they are bound in the group —C(=NR$^{14}$)N(R$^{14a}$)R$^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

$C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or or two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

each n is independently 0, 1 or 2; and each m is independently 0 or 1;

and the N-oxides, stereoisomers and agriculturally or veterinarily acceptable salts thereof.

Preferably, however, the invention relates to compounds of formula I wherein $X^1$ is O or $CH_2$;

A is a group of following formula:

wherein # denotes the bond to the aromatic ring of formula (I);

W is selected from O and S;

Y is selected from hydrogen, —N(R$^5$)R$^6$ and —OR$^9$;

$B^1$, $B^2$ and $B^3$ are each independently $CR^2$;

$G^1$ and $G^2$ are each independently $CR^4$;

$R^{g1}$ and $R^{g2}$ form together a bridging group selected from —$CH_2CH_2CH_2CH_2$— and —$CH_2CH_2CH_2$—;

$R^1$ is $CF_3$;

each $R^2$ is independently selected from the group consisting of hydrogen, halogen, $C_1$-$C_2$-haloalkoxy and $C_1$-$C_2$-haloalkyl;

$R^{3a}$, $R^{3b}$ are each independently selected from the group consisting of hydrogen, halogen, hydroxyl, —$CO_2R^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group =O, =C($R^{3c}$)$_2$, =NOH or =NOCH$_3$;

each $R^{3c}$ is independently selected from the group consisting of hydrogen, halogen, CH$_3$ and CF$_3$;

$R^{3d}$ is selected from the group consisting of hydrogen, $C_1$-$C_6$-alkyl and $C_1$-$C_3$-alkyloxy-$C_1$-$C_3$-alkyl-;

each $R^4$ is independently selected from the group consisting of hydrogen, halogen and cyano;

$R^5$ selected from hydrogen, $C_1$-$C_6$-alkyl, $C_2$-$C_3$-alkynyl and CH$_2$—CN;

$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;

—N($R^{101a}$)$R^{101b}$, wherein $R^{101a}$ is selected from hydrogen and $C_1$-$C_6$-alkyl; and $R^{101b}$ is selected from hydrogen, —C(=O)N($R^{14a}$)$R^{14b}$, wherein $R^{14a}$ is selected from the group consisting of hydrogen and $C_1$-$C_6$-alkyl; and $R^{14b}$ is selected from the group consisting of hydrogen, $C_1$-$C_6$-alkyl, $C_2$-$C_4$-alkynyl, CH$_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy;

$R^{101b}$ is further selected from phenyl, optionally substituted with 1, 2, 3, 4 or substituents $R^{16}$, and a heterocyclic ring selected from rings of formulae E-1 to E-42

E-1

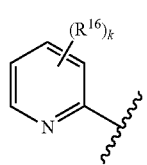

E-2

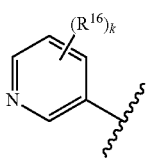

E-3

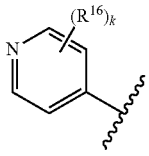

E-4

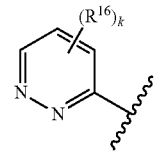

E-5

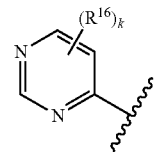

E-6

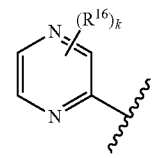

E-7

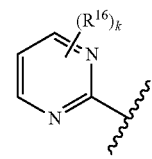

E-8

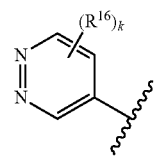

E-9

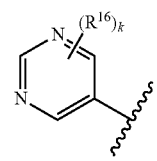

E-10

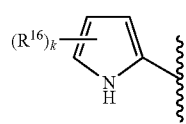

E-11

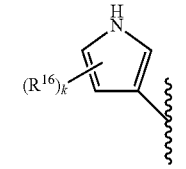

E-12

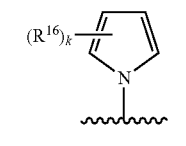

E-13

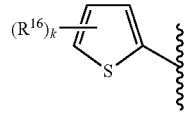

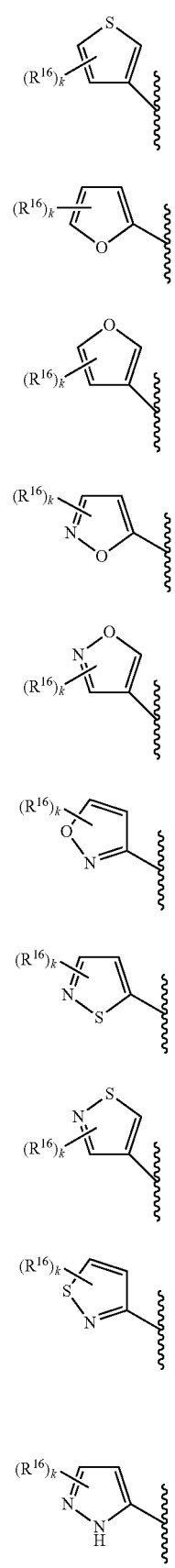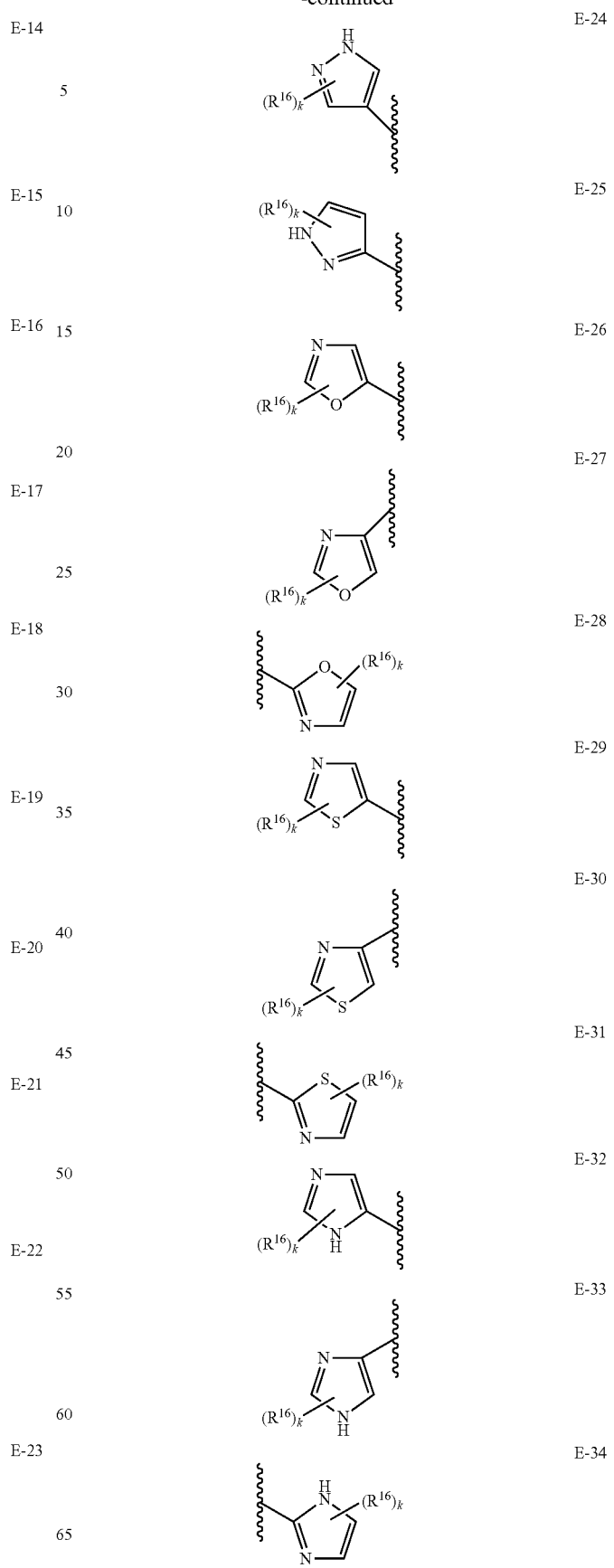

-continued

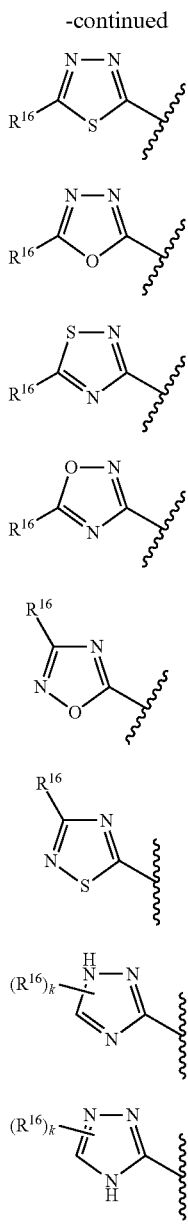

where in these rings E-1 to E-42 as a meaning for $R^{101b}$ the zigzag line denotes the attachment point to the remainder of the molecule;

k is 0, 1, 2 or 3, and each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl;

$R^6$ is further selected from —CH=NOR$^{9a}$, wherein $R^{9a}$ is selected from hydrogen, $C_1$-$C_6$-alkyl and $C_1$-$C_6$-haloalkyl;

phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and SO$_2$, as ring members, where the heteromonocyclic ring may be substituted with one or more substituents $R^{11}$;

wherein each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated heterocyclic ring may form together =O or =S; or two $R^{11}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

each $R^8$ is independently selected from OH, CN, $C_3$-$C_8$-cycloalkyl which optionally carries a CN or a $C_1$-$C_2$-haloalkyl substituent; $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2, 3 or 4 heteroatoms or heteroatom groups independently selected from N, O, S, NO, SO and SO$_2$, as ring members, where the heteromonocyclic ring may be substituted with one or more substituents $R^{16}$;

wherein $R^{102a}$ is selected from the group consisting of hydrogen, $C_1$-$C_6$-alkyl, $C_2$-$C_3$-alkynyl and CH$_2$—CN;

$R^{102b}$ is selected from the group consisting of hydrogen, $C_1$-$C_6$-alkyl, $C_2$-$C_4$-alkenyl, $C_2$-$C_4$-alkynyl, CH$_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_6$-alkoxy, $C_1$-$C_6$-haloalkoxy, phenyl which is optionally substituted with 1, 2, 3, 4 or 5 substituents selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-42 as defined above and E-43 to E-57:

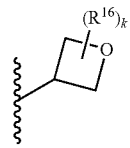

E-43

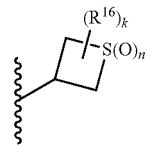

E-44

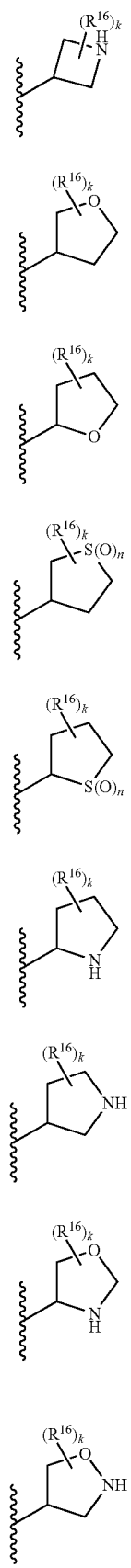

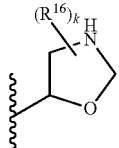
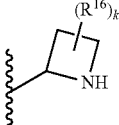
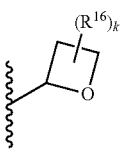
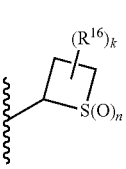

where in these rings E-43 to E-57
the zigzag line denotes the attachment point to the remainder of the molecule;
k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or
two $R^{16}$ present on the same carbon atom of a saturated ring may form together =O or =S; and each $R^{16}$ as a substituent on phenyl (as a meaning of $R^8$) or the heterocyclic rings (as a meaning of $R^8$) is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated heterocyclic ring may form together =O or =S; or
two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

or
$R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

or $R^5$ and $R^6$ together form a group =$S(R^{9b})_2$, where $R^{9b}$ is selected from $C_1$-$C_6$-alkyl and $C_1$-$C_6$-haloalkyl;

$R^9$ is selected from the group consisting of hydrogen, $C_1$-$C_6$-alkyl, $C_1$-$C_6$-haloalkyl and $C_1$-$C_6$-alkyl substituted by one radical $R^{13}$; where $R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-57 as defined above;

where in these rings E-1 to E-57 as a meaning of $R^{13}$ the zigzag line denotes the attachment point to the remainder of the molecule;

k is 0, 1, 2 or 3, n is 0, 1 or 2; and each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or two $R^{16}$ present on the same carbon atom of a saturated ring may form together =O or =S; and each $R^{16}$ in all other cases (i.e. as a substituent on phenyl as a meaning for $R^{101b}$) is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C(($C_1$-$C_4$-alkyl)$C_1$-$C_4$-alkyl; or or two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

and the N-oxides, stereoisomers and agriculturally or veterinarily acceptable salts thereof.

In a particular embodiment, $R^{11}$, in addition to the above definitions, is further selected from $C_3$-$C_6$-cycloalkyl-$C_1$-$C_4$-alkyl.

In a particular embodiment, the invention relates to compounds I as defined in the above preferred embodiment, the N-oxides, stereoisomers and agriculturally or veterinarily acceptable salts thereof, where however each $R^8$ is independently selected from OH, CN, $C_3$-$C_8$-cycloalkyl which optionally carries a CN or $CF_3$ substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{16}$;

wherein $R^{102a}$ is selected from the group consisting of hydrogen, $C_1$-$C_6$-alkyl, $C_2$-$C_3$-alkynyl and $CH_2$—CN;

$R^{102b}$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_6$-alkoxy, $C_1$-$C_6$-haloalkoxy, phenyl which is optionally substituted with 1, 2, 3, 4 or 5 substituents selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-42 as defined above and E-43 to E-57:

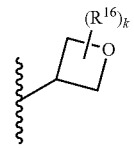

E-43

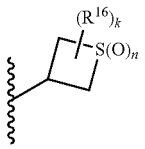

E-44

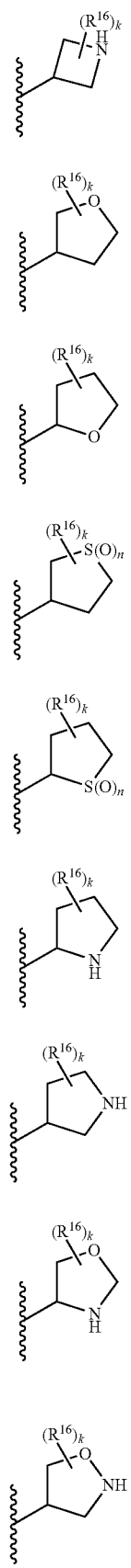

where in these rings E-43 to E-57
the zigzag line denotes the attachment point to the remainder of the molecule;
k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or
two $R^{16}$ present on the same carbon atom of a saturated ring may form together =O or =S; and
each $R^{16}$ as a substituent on phenyl (as a meaning of $R^8$) or the heterocyclic rings (as a meaning of $R^8$) is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated heterocyclic ring may form together =O or =S; or
two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$.

The present invention also provides an agricultural composition comprising at least one compound of the formula I as defined herein, a stereoisomer thereof and/or at least one agriculturally acceptable salt thereof and at least one inert liquid and/or solid agriculturally acceptable carrier.

The present invention also provides a veterinary composition comprising at least one compound of the formula I as defined herein, a stereoisomer thereof and/or at least one veterinarily acceptable salt thereof and at least one inert liquid and/or solid veterinarily acceptable carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I, a stereoisomer thereof and/or at least one agriculturally acceptable salt thereof as defined herein.

The method serves in particular for protecting plants from attack or infestation by invertebrate pests, and thus comprises treating the plants with a pesticidally effective amount of at least one compound of the formula I as defined above, a stereoisomer thereof and/or at least one agriculturally acceptable salt thereof. The method further serves in particular for protecting plant propagation material and/or the plants which grow therefrom from attack or infestation by invertebrate pests, and thus comprises treating the plant propagation material with a pesticidally effective amount of at least one compound of the formula I as defined above, a stereoisomer thereof and/or at least one agriculturally acceptable salt thereof.

The present invention also relates to plant propagation material, in particular seed, comprising at least one compound of formula I, a stereoisomer thereof and/or at least one agriculturally acceptable salt thereof as defined herein.

The present invention further relates to a method for treating or protecting an animal from infestation or infection by parasites (invertebrate pests) which comprises bringing the animal in contact with a parasiticidally/pesticidally effective amount of a compound of the formula I, a stereoisomer thereof and/or at least one veterinarily acceptable salt thereof as defined herein. Bringing the animal in contact with the compound I, its salt or the veterinary composition of the invention means applying or administering it to the animal.

The present invention further relates to compounds of the formula I, stereoisomers thereof and/or veterinarily acceptable salts thereof as defined herein for use as a medicament, especially for use as a medicament for treating or protecting an animal from infestation or infection by parasites (invertebrate pests).

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isoxazoline or pyrroline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

In a specific embodiment, the compounds I are present in form of a mixture of compounds I.1 and I.2

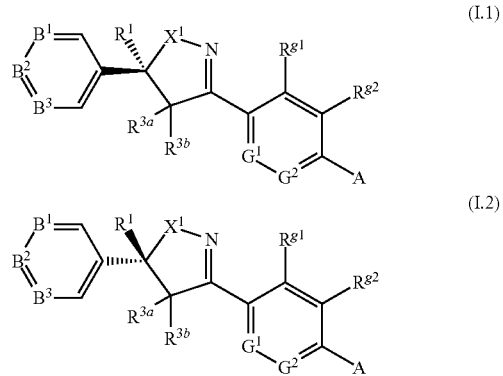

where compound I.1 is present in an amount of more than 50% by weight, in particular of at least 70% by weight, specifically of at least 90% by weight, based on the total weight of compounds I.1 and I.2.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of the isoxazoline/pyrroline moiety and/or, if $G^1$ or $G^2$ is N, this nitrogen atom, and/or of the bridging group formed by $R^{g1}$ and $R^{g2}$ and/or of any nitrogen-containing heterocyclic group present in group A with a suitable oxidizing agent, such as peroxo carboxylic acids or other peroxides. The person skilled in the art knows if and in which positions compounds of the present invention may form N-oxides.

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetraethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibit-tors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins.

Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (*Diptera*), and moths (*Lepidoptera*) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to ("$C_1$-$C_{10}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally n-butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof. $C_2$-$C_4$-Alkyl is ethyl, propyl, isopropyl, n-butyl, 1-methylpropyl (sec-butyl), 2-methylpropyl (isobutyl) or 1,1-dimethylethyl (tert-butyl).

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), 2 to 6 ("$C_2$-$C_6$-alkenyl"), 2 to 8 ("$C_2$-$C_8$-alkenyl") or 2 to 10 ("$C_2$-$C_{10}$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl"), 2 to 6 ("$C_2$-$C_6$-alkynyl"), 2 to 8 ("$C_2$-$C_8$-alkynyl"), or 2 to 10 ("$C_2$-$C_{10}$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 2 to 8 ("$C_2$-$C_8$-haloalkynyl") or 2 to 10 ("$C_2$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl, apart those mentioned for $C_3$-$C_6$-cycloalkyl-$C_1$-$C_4$-alkyl, are cycloheptylmethyl, cycloheptylethyl, cyclooctylmethyl and the like.

The term "$C_3$-$C_6$-cycloalkyl-methyl" refers to a $C_3$-$C_6$-cycloalkyl group which is bound to the remainder of the molecule via a methylene group ($CH_2$). Examples are cyclopropylmethyl, cyclobutylmethyl, cyclopentylmethyl and cyclohexylmethyl.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHC_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_6$-alkyl" as used herein, refers to a straight-chain or branched alkyl group having 1 to 6 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxymethyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_3$-alkylsulfonyl" is a $C_1$-$C_3$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3- dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [$S(O)_2$] group. The term "$C_1$-$C_3$-haloalkylsulfonyl" is a $C_1$-$C_3$-haloalkyl group, as defined above, attached via a sulfonyl [$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. The term "$C_1$-$C_{10}$-haloalkylsulfonyl" is a $C_1$-$C_{10}$-haloalkyl group, as defined above, attached via a sulfonyl [$S(O)_2$] group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl or 1-($CH_2Br$)-2-bromoethylsulfonyl. $C_1$-$C_4$-Haloalkylsulfonyl is additionally, for example, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a $CH_2$ group by a $C(=O)$ group.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl [$C(=O)$] group. Examples are acetyl (methylcarbonyl), propionyl (ethylcarbonyl), propylcarbonyl, isopropylcarbonyl, n-butylcarbonyl and the like.

The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl [$C(=O)$] group. Examples are trifluoromethylcarbonyl, 2,2,2-trifluoroethylcarbonyl and the like.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl [$C(=O)$] group. Examples are methoxycarbonyl, ethoxycarbonyl, propoxycarbonyl, isopropoxycarbonyl, n-butoxycarbonyl and the like.

The term "haloalkoxycarbonyl" is a $C_1$-$C_6$-haloalkoxy ("$C_1$-$C_6$-haloalkoxycarbonyl"), preferably a $C_1$-$C_4$-haloalkoxy ("$C_1$-$C_4$-haloalkoxycarbonyl") group, as defined above, attached via a carbonyl [$C(=O)$] group. Examples are trifluoromethoxycarbonyl, 2,2,2-trifluoroethoxycarbonyl and the like.

The term "$C_1$-$C_6$-alkylamino" is a group —$N(H)C_1$-$C_6$-alkyl. Examples are methylamino, ethylamino, propylamino, isopropylamino, butylamino and the like.

The term "di-($C_1$-$C_6$-alkyl)amino" is a group —$N(C_1$-$C_6$-alkyl)$_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

The term "aminocarbonyl" is a group —$C(=O)$—$NH_2$.

The term "$C_1$-$C_4$-alkylaminocarbonyl" is a group —$C(=O)$—$N(H)C_1$-$C_4$-alkyl. The term "$C_1$-$C_6$-alkylaminocarbonyl" is a group —$C(=O)$—$N(H)C_1$-$C_6$-alkyl. Examples are methylaminocarbonyl, ethylaminocarbonyl, propylaminocarbonyl, isopropylaminocarbonyl, butylaminocarbonyl and the like.

The term "di-($C_1$-$C_4$-alkyl)aminocarbonyl" is a group —$C(=O)$—$N(C_1$-$C_4$-alkyl)$_2$. The term "di-($C_1$-$C_6$-alkyl) aminocarbonyl" is a group —$C(=O)$—$N(C_1$-$C_6$-alkyl)$_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

The term "3-, 4-, 5-, 6-, 7-, 8-, 9- or 10-membered saturated, partially unsaturated or maximally unsaturated heterocyclic ring containing 1, 2 or 3 (or 4) heteroatoms or heteroatom groups selected from N, O, S, NO, SO and $SO_2$, as ring members" denotes a 3-, 4-, 5-, 6- or 7-membered saturated, partially unsaturated or maximum unsaturated heteromonocyclic ring or a 8-, 9- or 10-membered saturated, partially unsaturated or maximally unsaturated heterobicyclic ring containing 1, 2 or 3 (or 4) heteroatoms or heteroatom groups selected from N, O, S, NO, SO and $SO_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic" ] as used herein denotes monocyclic radicals, the monocyclic radicals being saturated, partially unsaturated or maximum unsaturated (including aromatic). The term "3-, 4-, 5-, 6-, 7- or 8-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic" ] as used herein further also encompasses 8-membered heteromonocyclic radicals containing 1, 2 or 3 (or 4) heteroatoms or heteroatom groups selected from N, O, S, NO, SO and $SO_2$, as ring members, the monocyclic radicals being saturated, partially unsaturated or maximum unsaturated (including aromatic). Unsaturated rings contain at least one C—C and/or C—N and/or N—N double bond(s). Maximum unsaturated rings contain as many conjugated C—C and/or C—N and/or N—N double bonds as allowed by the ring size. Maximum unsaturated 5- or 6-membered heterocyclic rings are aromatic. 7- and 8-membered rings cannot be aromatic. They are homoaromatic (7-membered ring, 3 double bonds) or have 4 double bonds (8-membered ring). The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 1,2,3,4-tetrazolidin-1-yl, 1,2,3,4-tetrazolidin-2-yl, 1,2,3,4-tetrazolidin-5-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2,3-dihydro-1,2,4-triazol-1-, -2-, -3- or -5-yl, 4,5-dihydro-1,3,4-triazol-1-, -2-, -4- or -5-yl, 2,5-dihydro-1,3,4-triazol-1-, -2- or -5-yl, 4,5-dihydro-1,2,3-triazol-1-, -4- or -5-yl, 2,5-dihydro-1,2,3-triazol-1-, -2- or -5-yl, 2,3-dihydro-1,2,3-triazol-1-, -2-, -3-, -4- or -5-yl, 2,3-dihydro-1,2,3,4-tetrazol-1-, -2-, -3- or -5-yl, 2,5-dihydro-1,2,3,4-tetrazol-1-, -2- or -5-yl, 4,5-dihydro-1,2,3,4-tetrazol-1-, -4- or -5-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7-tetrahydro [1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,2,3,4-1H-tetrazol-1-yl, 1,2,3,4-1H-tetrazol-5-yl, 1,2,3,4-2H-tetrazol-2-yl, 1,2,3,4-2H-tetrazol-5-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples for a 8-, 9- or 10-membered saturated heterobicyclic ring containing 1, 2 or 3 (or 4) heteroatoms or heteroatom groups selected from N, O, S, NO, SO and $SO_2$, as ring members are:

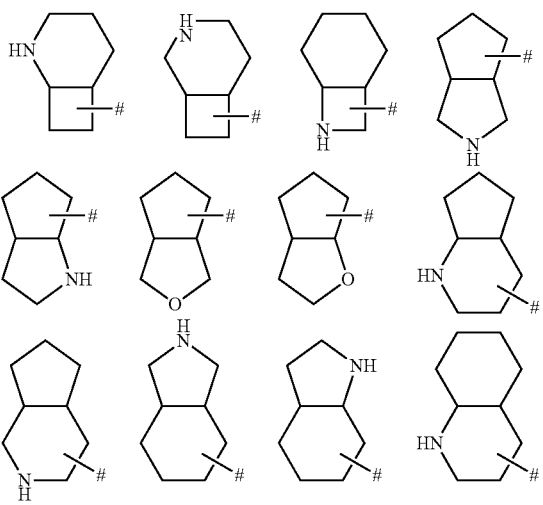

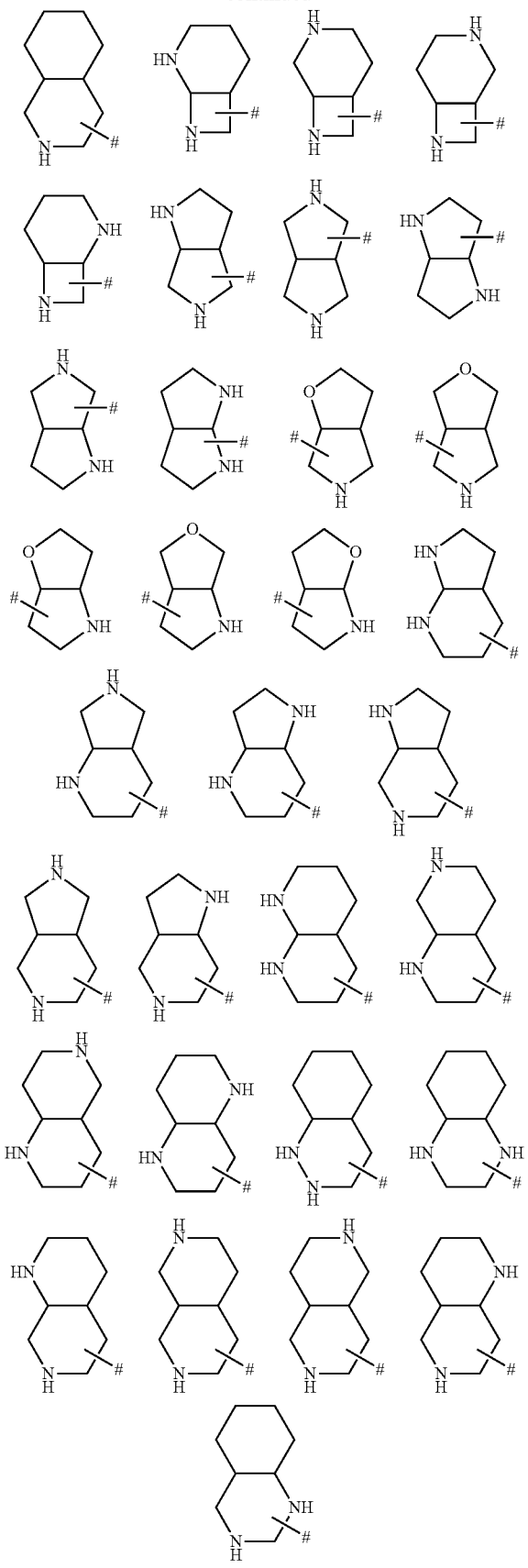
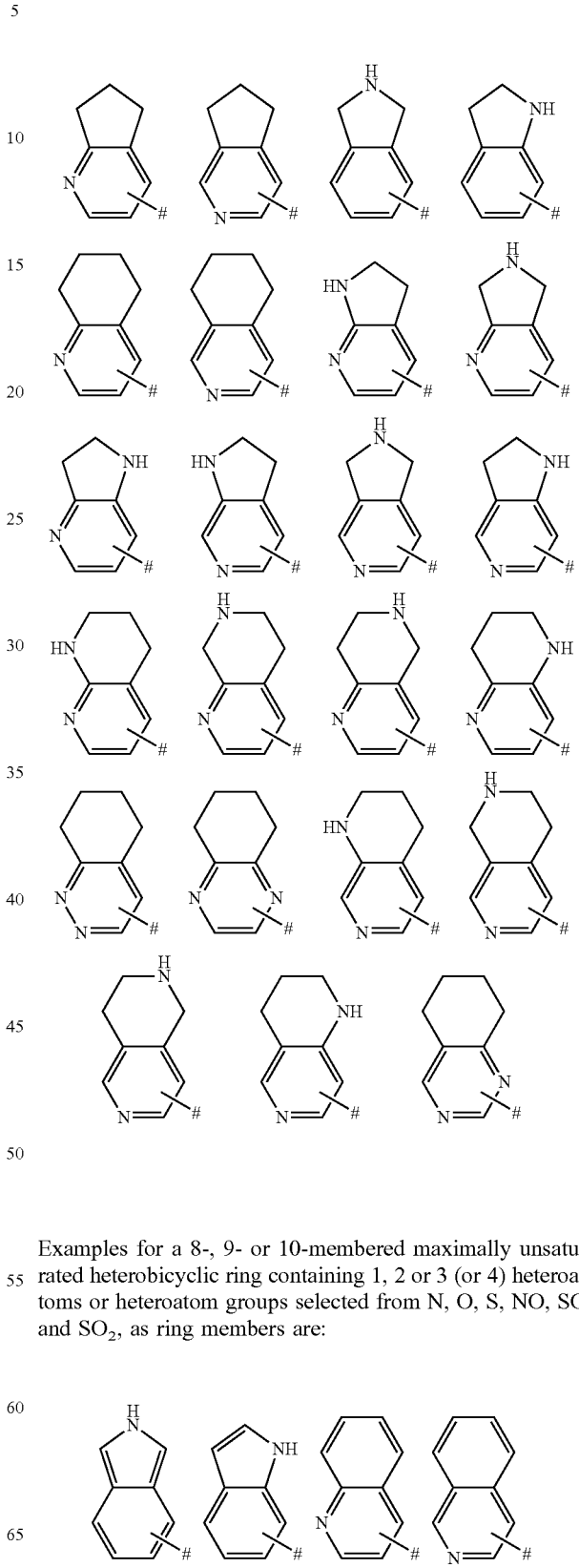
Examples for a 8-, 9- or 10-membered partially unsaturated heterobicyclic ring containing 1, 2 or 3 (or 4) heteroatoms or heteroatom groups selected from N, O, S, NO, SO and $SO_2$, as ring members are:
Examples for a 8-, 9- or 10-membered maximally unsaturated heterobicyclic ring containing 1, 2 or 3 (or 4) heteroatoms or heteroatom groups selected from N, O, S, NO, SO and $SO_2$, as ring members are:

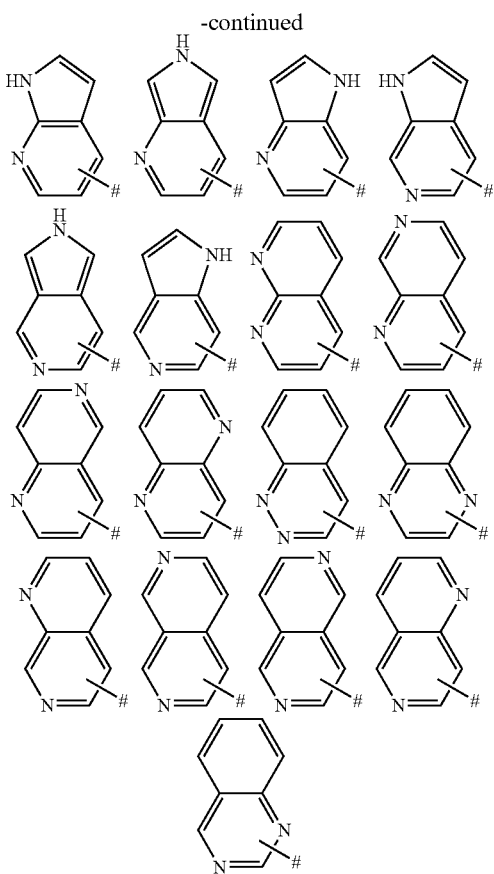

In the above structures # denotes the attachment point to the remainder of the molecule. The attachment point is not restricted to the ring on which is shown, but can be on either of the fused rings, and may be on a carbon or on a nitrogen ring atom. If the rings carry one or more substituents, these may be bound to carbon and/or to nitrogen ring atoms (if the latter are not part of a double bond).

A saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from C=O, C=S and C=$NR^{14}$ as ring members is either carbocyclic or heterocyclic. Examples are, in addition to the saturated heteromonocyclic rings mentioned above, carbocyclic rings, such as cyclopropyl, cyclopropanonyl, cyclobutyl, cyclobutanonyl, cyclopentyl, cyclopentanonyl, cyclohexyl, cyclohexanonyl, cyclohexadienonyl, cycloheptyl, cycloheptanonyl, cyclooctyl, cyclooctanonyl, furan-2-onyl, pyrrolidine-2-onyl, pyrrolidine-2,5-dionyl, piperidine-2-onyl, piperidine-2,6-dionyl and the like.

The remarks made below concerning preferred embodiments of the variables of the compounds of formula I, especially with respect to their substituents A, $X^1$, $B^1$, $B^2$, $B^3$, $G^1$, $G^2$, $R^{g1}$, $R^{g2}$, $R^1$, $R^2$, $R^{3a}$, $R^{3b}$, $R^{3c}$, $R^{3d}$, $R^4$, $R^5$, $R^6$, $R^8$, $R^9$, $R^{9a}$, $R^{9b}$, $R^{101a}$, $R^{101b}$, $R^{102a}$, $R^{102b}$, $R^{11}$, $R^{13}$, $R^{14a}$, $R^{14b}$, $R^{16}$, m and n, the features of the use and method according to the invention and of the composition of the invention are valid both on their own and, in particular, in every possible combination with each other.

In the heterocyclic rings, $R^{11}$ and $R^{16}$ may be bound to a carbon ring atom or to a secondary nitrogen ring atom (in the latter case thus replacing for example the hydrogen atom shown in the E-x or F-x rings). If $R^{11}$ or $R^{16}$ are bound to a nitrogen ring atom, $R^{11}$ and $R^{16}$ are preferably not halogen, cyano, nitro or a radical bound via O or S, such as —OH, —SH, alkoxy, haloalkoxy, alkylthio, haloalkylthio, alkylsulfinyl, haloalkylsulfinyl, alkylsulfonyl or haloalkylsulfonyl.

In one embodiment of the invention $X^1$ is O.
In another embodiment of the invention $X^1$ is $CH_2$.
W is preferably O.
In one embodiment of the invention (embodiment 1) Y is —$OR^9$, wherein $R^9$ has one of the above general, or, in particular, one of the below preferred meanings.

In a preferred embodiment of embodiment 1 (embodiment 1a), $R^9$ is selected from hydrogen, $C_1$-$C_6$-alkyl and $C_1$-$C_6$-haloalkyl.

Compounds I wherein Y is —$OR^9$ have biological activity, but are especially useful as intermediate compounds in the preparation of compounds I wherein Y is —$N(R^5)R^6$. Thus, the invention also relates to intermediate compounds I wherein Y is —$OR^9$, wherein $R^9$ has one of the above-defined general meanings or, preferably, one of the above-defined preferred meanings; and to the use of such compounds in the preparation of compounds I wherein Y is —$N(R^5)R^6$.

Compounds I wherein Y is H have biological activity, too, but are especially useful as intermediate compounds in the preparation of compounds I wherein Y is —$N(R^5)R^6$. Thus, the invention also relates to intermediate compounds I wherein Y is hydrogen; and to the use of such compounds in the preparation of compounds I wherein Y is —$N(R^5)R^6$.

In another embodiment of the invention (embodiment 2) Y is —$N(R^5)R^6$; wherein $R^5$ and $R^6$ have one of the above general, or, in particular, one of the below preferred meanings.

In a preferred embodiment of embodiment 2 (embodiment 2a)
$R^5$ is hydrogen or $C_1$-$C_3$-alkyl;
$R^6$ is selected from hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;
—$N(R^{101a})R^{101b}$, wherein $R^{101a}$ and $R^{101b}$ are as defined below;
—CH=$NOR^{9a}$, wherein $R^{9a}$ is selected from hydrogen, $C_1$-$C_6$-alkyl and $C_1$-$C_6$-haloalkyl;
phenyl which may be substituted with 1, 2, 3, 4, or 5 substituents $R^{11}$, wherein $R^{11}$ is as defined below; and a heteromonocyclic ring selected from rings of formulae F-1 to F-57

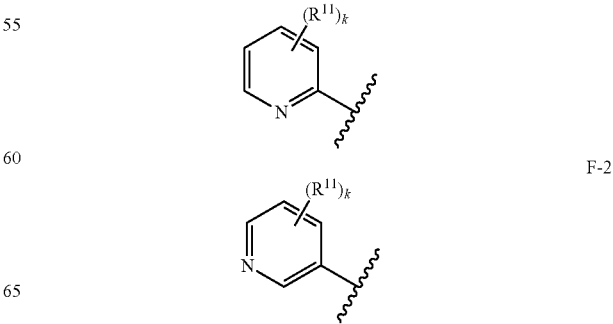

-continued
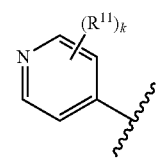 F-3
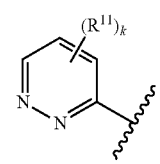 F-4
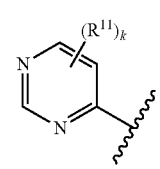 F-5
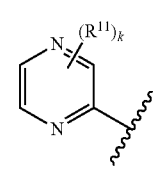 F-6
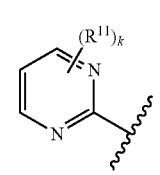 F-7
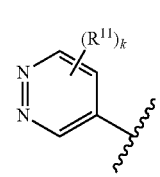 F-8
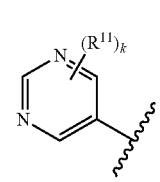 F-9
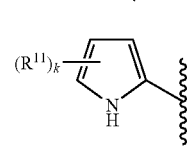 F-10
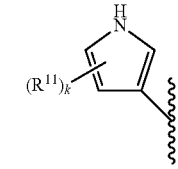 F-11
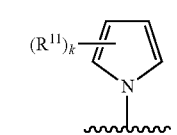 F-12
-continued
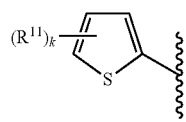 F-13
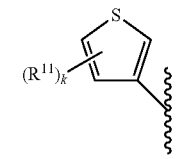 F-14
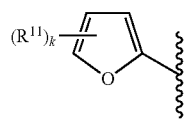 F-15
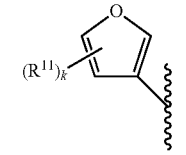 F-16
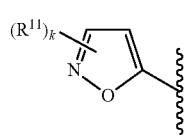 F-17
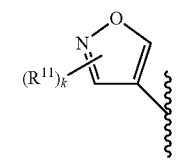 F-18
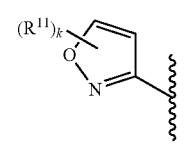 F-19
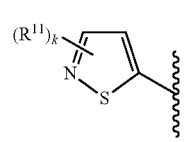 E-20
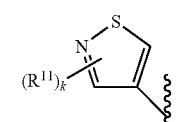 E-21
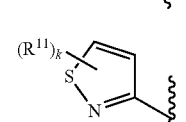 E-22
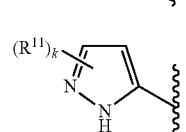 E-23

| | |
|---|---|
| E-24 | F-35 |
| E-25 | F-36 |
| E-26 | F-37 |
| E-27 | F-38 |
| E-28 | F-39 |
| E-29 | F-40 |
| F-30 | F-41 |
| F-31 | F-42 |
| F-32 | F-43 |
| F-33 | F-44 |
| F-34 | F-45 | where in F-1 to F-57
the zigzag line denotes the attachment point to the remainder of the molecule;
k is 0, 1, 2 or 3,
n is 0, 1 or 2, and
$R^{11}$ is as defined below;
$R^8$ is selected from OH, CN, $C_3$-$C_8$-cycloalkyl which optionally carries a CN or $CF_3$ substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a heterocyclic ring selected from rings of formulae E-1 to E-57 as defined above;
wherein
$R^{102a}$ in —C(=O)N($R^{102a}$)$R^{102b}$ as a meaning for $R^8$ is selected from the group consisting of hydrogen and $C_1$-$C_6$-alkyl; and
$R^{102b}$ in —C(=O)N($R^{102a}$)$R^{102b}$ as a meaning for $R^8$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_6$-alkoxy and $C_1$-$C_6$-haloalkoxy;
$R^{101a}$ in —N($R^{101a}$)$R^{101b}$ as a meaning for $R^6$ is selected from hydrogen and $C_1$-$C_6$-alkyl; and
$R^{101b}$ in —N($R^{101a}$)$R^{101b}$ as a meaning for $R^6$ is selected from hydrogen, —C(=O)N($R^{14a}$)$R^{14b}$, phenyl, optionally substituted with 1, 2, 3, 4 or 5 substituents $R^{16}$, wherein $R^{16}$ is as defined below; and a heteroaromatic ring selected from rings of formulae E-1 to E-42 as defined above;
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{11}$ present on the same carbon atom of a saturated heterocyclic ring may form together =O or =S; or two $R^{11}$ present on the same S or SO ring member of a heterocyclic ring may together form a group $=N(C_1\text{-}C_6\text{-alkyl})$, $=NO(C_1\text{-}C_6\text{-alkyl})$, $=NN(H)(C_1\text{-}C_6\text{-alkyl})$ or $=NN(C_1\text{-}C_6\text{-alkyl})_2$;

$R^{14a}$ in $-C(=O)N(R^{14a})R^{14b}$ as a meaning for $R^{102b}$ is selected from the group consisting of hydrogen and $C_1\text{-}C_6\text{-alkyl}$; and $R^{14b}$ in $-C(=O)N(R^{14a})R^{14b}$ as a meaning for $R^{102b}$ is selected from the group consisting of hydrogen, $C_1\text{-}C_6$-alkyl, $C_2\text{-}C_4$-alkynyl, $CH_2-CN$, $C_1\text{-}C_6$-haloalkyl, $C_3\text{-}C_6$-cycloalkyl, $C_3\text{-}C_6$-halocycloalkyl, $C_1\text{-}C_4$-alkoxy and $C_1\text{-}C_4$-haloalkoxy;

and each $R^{16}$ as a substituent on phenyl or heterocyclic rings of formulae E-1 to E-57 is independently selected from the group consisting of halogen, cyano, nitro, $C_1\text{-}C_4$-alkyl, $C_1\text{-}C_4$-haloalkyl, $C_1\text{-}C_4$-alkoxy, $C_1\text{-}C_4$-haloalkoxy, $C_1\text{-}C_4$-alkylthio, $C_1\text{-}C_4$-haloalkylthio, $C_1\text{-}C_4$-alkylsulfinyl, $C_1\text{-}C_4$-haloalkylsulfinyl, $C_1\text{-}C_4$-alkylsulfonyl, $C_1\text{-}C_4$-haloalkylsulfonyl, $C_3\text{-}C_6$-cycloalkyl, $C_3\text{-}C_6$-halocycloalkyl, $C_2\text{-}C_4$-alkenyl, $C_2\text{-}C_4$-haloalkenyl, $C_2\text{-}C_4$-alkynyl, $C_2\text{-}C_4$-haloalkynyl, $C_1\text{-}C_4$-alkylcarbonyl, $C_1\text{-}C_4$-haloalkylcarbonyl, aminocarbonyl, $C_1\text{-}C_4$-alkylaminocarbonyl and di-$(C_1\text{-}C_4$-alkyl$)$-aminocarbonyl; or two $R^{16}$ present on the same carbon atom of a saturated heterocyclic ring may form together $=O$ or $=S$; or two $R^{16}$ present on the same S or SO ring member of a heterocyclic ring may together form a group $=N(C_1\text{-}C_6\text{-alkyl})$, $=NO(C_1\text{-}C_6\text{-alkyl})$, $=NN(H)(C_1\text{-}C_6\text{-alkyl})$ or $=NN(C_1\text{-}C_6\text{-alkyl})_2$.

In a preferred embodiment of embodiment 2a, $R^{11}$, in addition to the above definitions, is also selected from $C_3\text{-}C_6$-cycloalkyl-$C_1\text{-}C_4$-alkyl.

In a particular embodiment of embodiment 2a (embodiment 2aa), $R^6$, in addition to the above definitions in embodiment 2a, is also selected from rings F-58 to F-60

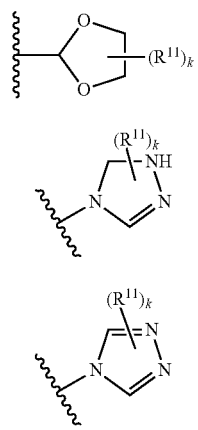

F-58

F-59

F-60 where k and $R^{11}$ are as defined for rings F-1 to F-57, where however additionally, two $R^{11}$ present on the same carbon atom of a partially unsaturated heterocyclic ring (like ring F-59) may form together $=O$ or $=S$;

and $R^8$, in addition to the above definitions in embodiment 2a, is also selected from $C_3\text{-}C_8$-cycloalkyl which optionally carries a $CHF_2$ substituent, and from 1,3-dioxolan-2-yl which may carry 1, 2 or 3 substituents $R^{16}$ as defined above.

In a preferred embodiment of embodiment 2aa, $R^{11}$, in addition to the above definitions, is also selected from $C_3\text{-}C_6$-cycloalkyl-$C_1\text{-}C_4$-alkyl.

In another preferred embodiment of embodiment 2 (embodiment 2b)

$R^5$ is hydrogen or $C_1\text{-}C_3$-alkyl;

$R^6$ is selected from hydrogen, $C_1\text{-}C_6$-alkyl, $C_1\text{-}C_6$-haloalkyl, $C_1\text{-}C_4$-alkyl which carries one radical $R^8$, wherein $R^8$ is as defined below; $C_2\text{-}C_6$-alkenyl, $C_2\text{-}C_6$-haloalkenyl, $C_2\text{-}C_6$-alkynyl, $C_3\text{-}C_6$-cycloalkyl which may be substituted by 1 or 2 substituents selected from F, CN and pyridyl;

—$N(R^{101a})R^{101b}$, wherein $R^{101a}$ and $R^{101b}$ are as defined below;

—$CH=NOR^{9a}$, wherein $R^{9a}$ is selected from hydrogen, $C_1\text{-}C_6$-alkyl and $C_1\text{-}C_6$-haloalkyl;

phenyl which may be substituted with 1, 2, 3, 4, or 5 substituents $R^{11}$, wherein $R^{11}$ is as defined below; and a heteromonocyclic ring selected from rings of formulae F-1 to F-57 as defined above;

where in F-1 to F-57 the zigzag line denotes the attachment point to the remainder of the molecule;

k is 0, 1, 2 or 3, n is 0, 1 or 2, and $R^{11}$ is as defined below;

$R^8$ is selected from OH, CN, $C_3\text{-}C_8$-cycloalkyl which optionally carries a CN or $CF_3$ substituent, $C_3\text{-}C_8$-halocycloalkyl, $C_1\text{-}C_6$-alkoxy, $C_1\text{-}C_6$-haloalkoxy, $C_1\text{-}C_6$-alkylthio, $C_1\text{-}C_6$-haloalkylthio, $C_1\text{-}C_6$-alkylsulfinyl, $C_1\text{-}C_6$-haloalkylsulfinyl, $C_1\text{-}C_6$-alkylsulfonyl, $C_1\text{-}C_6$-haloalkylsulfonyl, $-C(=O)N(R^{102a})R^{102b}$, phenyl, optionally substituted with 1, 2, 3, 4 or 5 substituents $R^{16}$, and a heterocyclic ring selected from rings of formulae E-1 to E-57 as defined above;

wherein $R^{102a}$ in $-C(=O)N(R^{102a})R^{102b}$ as a meaning for $R^8$ is selected from the group consisting of hydrogen and $C_1\text{-}C_6$-alkyl; and $R^{102b}$ in $-C(=O)N(R^{102a})R^{102b}$ as a meaning for $R^8$ is selected from the group consisting of hydrogen, $C_1\text{-}C_6$-alkyl, $C_1\text{-}C_6$-haloalkyl, $C_2\text{-}C_4$-alkenyl, $C_2\text{-}C_4$-alkynyl, $C_3\text{-}C_6$-cycloalkyl, $C_3\text{-}C_6$-halocycloalkyl, $C_3\text{-}C_6$-cycloalkyl-methyl, $CH_2-CN$, $C_1\text{-}C_6$-alkoxy and $C_1\text{-}C_6$-haloalkoxy;

$R^{101a}$ in $-N(R^{101a})R^{101b}$ as a meaning for $R^6$ is selected from hydrogen and $C_1\text{-}C_6$-alkyl; and $R^{101b}$ in $-N(R^{101a})R^{101b}$ as a meaning for $R^6$ is selected from hydrogen, —$C(=O)N(R^{14a})R^{14b}$, phenyl, optionally substituted with 1, 2, 3, 4 or 5 substituents $R^{16}$, wherein $R^{16}$ is as defined below; and a heteroaromatic ring selected from rings of formulae E-1 to E-42 as defined above;

each $R^{11}$ is independently selected from the group consisting of halogen, cyano, nitro, $C_1\text{-}C_4$-alkyl, $C_1\text{-}C_4$-haloalkyl, $C_1\text{-}C_4$-alkoxy, $C_1\text{-}C_4$-haloalkoxy, $C_1\text{-}C_4$-alkylthio, $C_1\text{-}C_4$-haloalkylthio, $C_3\text{-}C_6$-cycloalkyl, $C_3\text{-}C_6$-halocycloalkyl, $C_2\text{-}C_4$-alkenyl, $C_2\text{-}C_4$-haloalkenyl, $C_2\text{-}C_4$-alkynyl and $C_2\text{-}C_4$-haloalkynyl; or two $R^{11}$ present on the same carbon atom of a saturated heterocyclic ring may form together $=O$ or $=S$; or two $R^{11}$ present on the same S or SO ring member of a heterocyclic ring may together form a group $=N(C_1\text{-}C_6\text{-alkyl})$, $=NO(C_1\text{-}C_6\text{-alkyl})$, $=NN(H)(C_1\text{-}C_6\text{-alkyl})$ or $=NN(C_1\text{-}C_6\text{-alkyl})_2$;

$R^{14a}$ in —C(=O)N($R^{14a}$)$R^{14b}$ as a meaning for $R^{102b}$ is selected from the group consisting of hydrogen and $C_1$-$C_6$-alkyl; and $R^{14b}$ in —C(=O)N($R^{14a}$)$R^{14b}$ as a meaning for $R^{102b}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy;

and each $R^{16}$ as a substituent on phenyl or heterocyclic rings of formulae E-1 to E-57 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

In a preferred embodiment of embodiment 2b, $R^{11}$, in addition to the above definitions, is also selected from $C_3$-$C_6$-cycloalkyl-$C_1$-$C_4$-alkyl.

In a particular embodiment of embodiment 2b (embodiment 2bb), $R^6$, in addition to the above definitions in embodiment 2b, is also selected from rings F-58 to F-60

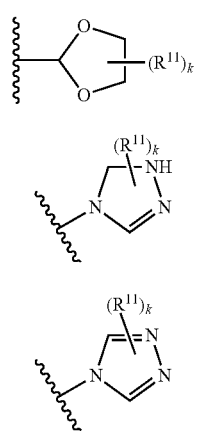

F-58

F-59

F-60 where k and $R^{11}$ are as defined for rings F-1 to F-57, where however additionally, two $R^{11}$ present on the same carbon atom of a partially unsaturated heterocyclic ring (like ring F-59) may form together =O or =S;

and $R^8$, in addition to the above definitions in embodiment 2b, is also selected from $C_3$-$C_8$-cycloalkyl which optionally carries a $CHF_2$ substituent, and from 1,3-dioxolan-2-yl which may carry 1, 2 or 3 substituents $R^{16}$ as defined above.

In a preferred embodiment of embodiment 2bb, $R^{11}$, in addition to the above definitions, is also selected from $C_3$-$C_6$-cycloalkyl-$C_1$-$C_4$-alkyl.

In a particular embodiment of embodiment 2 (embodiment 2c), $R^5$ is hydrogen or $C_1$-$C_3$-alkyl, and in particular hydrogen;

$R^6$ is selected from hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-alkynyl, $C_3$-$C_6$-cycloalkyl which may be substituted by 1 cyano group;

—N($R^{101a}$)$R^{101b}$, wherein $R^{101a}$ and $R^{101b}$ are as defined below;

and a heteromonocyclic ring selected from rings of formulae F-1 to F-57 as defined above;

where in F-1 to F-57 the zigzag line denotes the attachment point to the remainder of the molecule;

k is 0 or 1 preferably 0, n is 0, 1 or 2, and $R^{11}$ is as defined below;

$R^8$ is selected from CN, $C_3$-$C_8$-cycloalkyl which optionally carries a CN or $CF_3$ substituent, $C_3$-$C_{58}$-halocycloalkyl, —C(=O)N($R^{102a}$)$R^{102b}$, and a heterocyclic ring selected from rings of formulae E-1 to E-57 as defined above;

wherein $R^{102a}$ in —C(=O)N($R^{102a}$)$R^{102b}$ as a meaning for $R^8$ is selected from the group consisting of hydrogen and $C_1$-$C_6$-alkyl; and $R^{102b}$ in —C(=O)N($R^{102a}$)$R^{102b}$ as a meaning for $R^8$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_6$-alkoxy and $C_1$-$C_6$-haloalkoxy;

$R^{101a}$ in —N($R^{101a}$)$R^{101b}$ as a meaning for $R^6$ is selected from hydrogen and $C_1$-$C_6$-alkyl;

$R^{101b}$ in —N($R^{101a}$)$R^{101b}$ as a meaning for $R^6$ is selected from hydrogen, and a heteroaromatic ring selected from rings of formulae F-1 to F-42 as defined above;

each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated heterocyclic ring may form together =O or =S; or two $R^{11}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

and each $R^{16}$ as a substituent on phenyl or heterocyclic rings of formulae E-1 to E-57 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S; or two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$.

In a preferred embodiment of embodiment 2c, $R^{11}$, in addition to the above definitions, is also selected from $C_3$-$C_6$-cycloalkyl-$C_1$-$C_4$-alkyl.

In a particular embodiment of embodiment 2c (embodiment 2cc), $R^6$, in addition to the above definitions in embodiment 2c, is also selected from rings F-58 to F-60

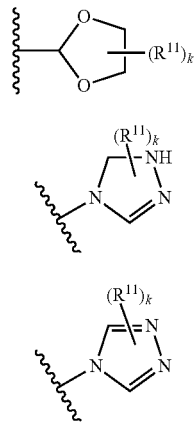

where k and $R^{11}$ are as defined for rings F-1 to F-57, where however additionally, two $R^{11}$ present on the same carbon atom of a partially unsaturated heterocyclic ring (like ring F-59) may form together =O or =S;

and $R^8$, in addition to the above definitions in embodiment 2a, is also selected from $C_3$-$C_8$-cycloalkyl which optionally carries a $CHF_2$ substituent, and from 1,3-dioxolan-2-yl which may carry 1, 2 or 3 substituents $R^{16}$ as defined above.

In a preferred embodiment of embodiment 2cc, $R^{11}$, in addition to the above definitions, is also selected from $C_3$-$C_6$-cycloalkyl-$C_1$-$C_4$-alkyl.

In another even more particular embodiment of embodiment 2 (embodiment 2d), $R^5$ is hydrogen or $C_1$-$C_3$-alkyl;

$R^6$ is selected from $C_1$-$C_4$-alkyl which carries one radical $R^8$, and a saturated heteromonocyclic ring selected from rings of formulae F-43 to F-57 as defined above; wherein $R^8$ is a saturated heterocyclic ring selected from rings of formulae E-43 to E-57 as defined above;

$R^{11}$ as a substituent on heterocyclic rings of formulae F-43 to F-57 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$—$O_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated heterocyclic ring may form together =O or =S;

each $R^{16}$ as a substituent on heterocyclic rings of formulae E-43 to E-57 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$—$O_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

In a preferred embodiment of embodiment 2d, $R^{11}$, in addition to the above definitions, is also selected from $C_3$-$C_6$-cycloalkyl-$C_1$-$C_4$-alkyl.

In embodiment 2c, and also 2cc and also 2d, the heteromonocyclic ring $R^6$ is preferably selected from rings of formulae F-44-1 and F-53-1 (see below), and the heterocyclic ring $R^8$ is preferably selected from rings of formulae E-1, E-2, E-3, E-5, E-7, E-44-1 and E-57-1 (see below), specifically from E-1, E-7, E-44-1 and E-57-1 and very specifically from E-44-1 and E-57-1.

In embodiments 2, 2a, 2aa, 2b, 2bb, 2c, 2cc and 2d, the heteromonocyclic ring $R^6$ is preferably selected from rings of formulae F-44-1 and F-53-1, and the heterocyclic ring $R^8$ is preferably selected from rings of formulae E-44-1 and E-57-1

F-44-1

F-53-1

E-44-1

E-57-1 wherein n is 0, 1 or 2; and $R^{17}$ is selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl and $CH_2$—$C_3$-$C_6$-cycloalkyl.

In an especially preferred embodiment of embodiment 2 (embodiment 2e)

$R^5$ is hydrogen or $C_1$-$C_3$-alkyl, in particular hydrogen; and $R^6$ is selected from $C_1$-$C_4$-alkyl (especially methyl) which carries one radical $R^8$; a ring of formula F-44-1, and a ring of formula F-53-1 as defined above; wherein $R^8$ is selected from a ring of formula E-44-1 and a ring of formula E-57-1 as defined above.

In another preferred embodiment of embodiment 2 (embodiment 2f), $R^5$ and $R^6$ together form a group =$S(R^{9b})_2$, where $R^{9b}$ is selected from $C_1$-$C_4$-alkyl and $C_1$-$C_2$-haloalkyl and in particular from $C_1$-$C_4$-alkyl.

In another preferred embodiment of embodiment 2 (embodiment 2g), $R^5$ and $R^6$, together with the nitrogen atom to which they are bound, form a 5-membered saturated heterocyclic ring, where the ring may further contain 1 or 2 heteroatoms or heteroatom-containing groups selected from NH and C=O as ring members, wherein the heterocyclic ring may be substituted with 1, 2 or 3 substituents independently selected from $C_1$-$C_6$-alkyl and $C_1$-$C_6$-haloalkyl. In a particular embodiment of embodiment 2g (embodiment 2gg), $R^5$ and $R^6$, together with the nitrogen atom to which they are bound, form an imidazolidinon-1-yl ring, especially an imidazolidin-4-on-1-yl ring which may be substituted with 1 or 2 substituents independently selected from $C_1$-$C_6$-alkyl and $C_1$-$C_6$-haloalkyl.

Preferably, $B^1$ is $CR^2$, where $R^2$ is not hydrogen, and $B^2$ and $B^3$ are $CR^2$, where $R^2$ has one of the above general, or, in particular, one of the below preferred meanings. In a particular embodiment (embodiment 3a), in compounds I, $B^1$ is $CR^2$, where $R^2$ is not hydrogen, and $B^2$ and $B^3$ are $CR^2$, where $R^2$ has one of the above general or, in particular, one of the below preferred meanings; W is O; and Y is as defined in any of the above embodiments 1a, 2a, 2aa, 2b, 2bb, 2c, 2cc, 2d, 2e, 2f, 2g or 2gg.

Preferably, $R^2$ is selected from hydrogen, F, Cl, Br, $OCF_3$ and $CF_3$; and is specifically F or Cl.

In a particular embodiment (embodiment 3b), in compounds I, $B^1$ is $CR^2$, where $R^2$ is not hydrogen, and $B^2$ and $B^3$ are $CR^2$, where $R^2$ is selected from hydrogen, F, Cl, Br, $OCF_3$ and $CF_3$; and is specifically F or $C_1$; W is O; and Y is as defined in any of the above embodiments 1a, 2a, 2aa, 2b, 2bb, 2c, 2cc, 2d, 2e, 2f, 2g or 2gg.

Preferably, $G^1$ and $G^2$ are $CR^4$, where $R^4$ has one of the above general or, in particular, one of the below preferred meanings.

$R^4$ is in particular hydrogen.

In a particular embodiment (embodiment 4a), in compounds I, $R^4$ has one of the above general or, in particular, one of the below preferred meanings, and is in particular hydrogen; $B^1$, $B^2$ and $B^3$ are as defined in embodiments 3a or 3b, W is O; and Y is as defined in any of the above embodiments 1a, 2a, 2aa, 2b, 2bb, 2c, 2cc, 2d, 2e, 2f, 2g or 2gg.

In one embodiment, $R^{g1}$ and $R^{g2}$ form together a bridging group —$CH_2$—$CH_2$—$CH_2$—.

In another embodiment, $R^{g1}$ and $R^{g2}$ form together a bridging group —$CH_2$—$CH_2$—$CH_2$—$CH_2$—.

Preferably, $R^{3a}$ and $R^{3b}$ are independently selected from hydrogen and halogen, more preferably from hydrogen and fluorine, and are in particular hydrogen.

In a particular embodiment (embodiment 5a), in compounds I, $R^{3a}$ and $R^{3b}$ are hydrogen, $R^4$ is as defined in embodiment 4a; $B^1$, $B^2$ and $B^3$ are as defined in embodiments 3a or 3b, W is O; and Y is as defined in any of the above embodiments 1a, 2a, 2aa, 2b, 2bb, 2c, 2cc, 2d, 2e, 2f, 2g or 2gg.

If not specified otherwise above, $R^{16}$ has following preferred meanings:

$R^{16}$ is independently of each occurrence and independently of each other preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl, and more preferably from halogen, CN, $C_1$-$C_4$-alkyl, $C_1$-$C_4$-haloalkyl, $C_1$-$C_4$-alkoxy and $C_1$-$C_4$-haloalkoxy. If bound to a nitrogen atom, $R^{16}$ is not halogen.

In a particular embodiment, the compound of formula I is a compound of formula IA or an N-oxide, a stereoisomer or an agriculturally or veterinarily acceptable salt thereof

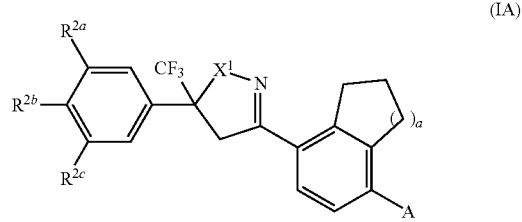

(IA)

wherein
$X^1$ is O of $CH_2$;
$R^{2a}$, $R^{2b}$ and $R^{2c}$ have one of the above general or, in particular, on of the above preferred meanings of $R^2$;
A has one of the above general or, in particular, on of the above preferred meanings; and
a is 1 or 2.

In particular, in compounds IA, in A, W is O and Y is as defined in any of embodiments 1a, 2a, 2aa, 2b, 2bb, 2c, 2cc, 2d, 2e, 2f, 2g or 2gg, and especially 2c, 2cc, 2d or 2e.

In a more particular embodiment, the compound of formula I is a compound of formula IB or a stereoisomer or an agriculturally or veterinarily acceptable salt thereof

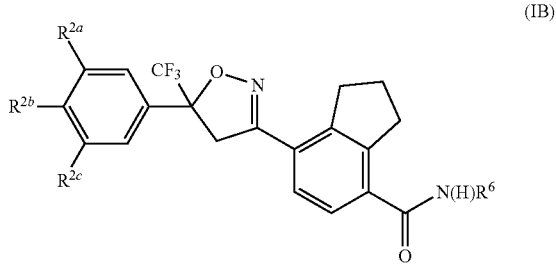

(IB)

wherein
$R^{2a}$ is Cl, $R^{2b}$ is F, $R^{2c}$ is Cl, and
$R^6$ is $CH_2$—C(O)—N(H)—$R^{102b}$, wherein
$R^{102b}$ is selected from the group consisting of $C_1$-$C_4$-alkyl, $C_2$-$C_4$-alkyl substituted with 1 or 2 fluorine atoms, $C_2$-$C_4$-alkenyl, $C_2$-$C_4$-alkynyl, $CH_2$—CN, $C_3$-$C_6$-cycloalkyl, $C_3$-$C_6$-halocycloalkyl and $C_3$-$C_6$-cycloalkylmethyl.

In another more particular embodiment, the compound of formula I is a compound of formula IB, as defined above, or a stereoisomer or an agriculturally or veterinarily acceptable salt thereof, where however
$R^{2a}$ is Cl, $R^{2b}$ is F, $R^{2c}$ is $C_1$, and
$R^6$ is —$CH_2$—$R^8$, wherein
$R^8$ is selected from rings E-5, E-6, E-7, E-19, E-25, E-27, E-44 and E-57 as defined above, where the rings E-5, E-6, E-7, E-19, E-27, E-44 and E-57 are unsubstituted (k is 0) or carry 1 or 2 substituents $R^{16}$ (k is 1 or 2); and is in particular selected from rings E-5, E-6, E-7, E-19, E-25, E-27, E-44-1 and E-57-1, where the rings E-5, E-6, E-7, E-19 and E-27 are unsubstituted (k is 0) or carry 1 or 2 substituents $R^{16}$ (k is 1 or 2),
wherein
each $R^{16}$ is independently selected from halogen, cyano, nitro, $C_1$-$C_2$-alkyl, $C_1$-$C_2$-haloalkyl, $C_1$-$C_2$- alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl, $C_2$-$C_3$-alkynyl; and where ring E-25 carries one substituent $R^{16}$ as defined above on the nitrogen atom in the 1-position (which is however not halogen, cyano, nitro, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl or $C_1$-$C_2$-haloalkylsulfonyl) and optionally carries 1 or 2 further substituents $R^{16}$ where $R^{16}$ is as defined above.

In yet another more particular embodiment, the compound of formula I is a compound of formula IB, as defined above, or a stereoisomer or an agriculturally or veterinarily acceptable salt thereof, where however $R^{2a}$ is Cl, $R^{2b}$ is F, $R^{2c}$ is Cl, and $R^6$ is selected from rings F-2, F-4, F-6, F-8, F-9, F-44, F-46, F-51 and F-53 as defined above, where the rings F-2, F-4, F-6, F-8, F-9, F-44, F-46 and F-53 are unsubstituted (k is 0) or carry 1 or 2 substituents $R^{11}$ (k is 1 or 2), wherein each $R^{11}$ is independently selected from halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl and $C_2$-$C_3$-alkynyl; and where ring F-51 is a ring of formula F-51-1

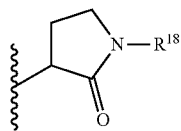

F-51-1 wherein $R^{18}$ is selected from the group consisting of hydrogen, $C_1$-$C_2$-alkyl, $C_1$-$C_2$-haloalkyl, $C_3$-$C_4$-cycloalkyl, $C_3$-$C_4$-halocycloalkyl, $C_2$-$C_3$-alkenyl and $C_2$-$C_3$-alkynyl;

and where rings F-44 and F-53 are preferably rings F-44-1 and F-53-1 as defined above.

In yet another more particular embodiment, the compound of formula I is a compound of formula IB, as defined above, or a stereoisomer or an agriculturally or veterinarily acceptable salt thereof, where however $R^{2a}$ is Cl, $R^{2b}$ is F, $R^{2c}$ is Cl, and $R^6$ is selected from $C_2$-$C_4$-alkyl which may be substituted with 1 or 2 fluorine atoms, cyclopropyl, $C_3$-$C_5$-halocycloalkyl, $CH_2$—($C_3$-$C_5$-halocycloalkyl), $CH_2$-(1-cyano-($C_3$-$C_5$-cycloalkyl)), $C_2$-$C_4$-alkenyl, $C_2$-$C_4$-alkynyl, $CH_2$—CN and —CH=$NOR^{9a}$, wherein $R^{9a}$ is selected from $C_1$-$C_3$-alkyl and $C_1$-$C_3$-haloalkyl.

In yet another more particular embodiment, the compound of formula I is a compound of formula IB, as defined above, or a stereoisomer or an agriculturally or veterinarily acceptable salt thereof, where however $R^{2a}$ is Cl, $R^{2b}$ is F, $R^{2c}$ is Cl, and $R^6$ is N(H)$R^{101b}$, wherein $R^{11b}$ is selected from —C(O)—N(H)$R^{14b}$ and rings E-1 and E-7 as defined above;

where $R^{14b}$ is selected from $C_1$-$C_3$-alkyl, $C_1$-$C_3$-haloalkyl and cyclopropyl; and where in rings E-1 and E-7 k is 0, 1 or 2; and each $R^{16}$ is independently selected from halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl, $C_2$-$C_3$-alkynyl.

In another more particular embodiment, the compound of formula I is a compound of formula IB, as defined above, or a stereoisomer or an agriculturally or veterinarily acceptable salt thereof, where however $R^{2a}$ is Cl, $R^{2b}$ is H, $R^{2c}$ is Cl, and $R^6$ is $CH_2$—C(O)—N(H)—$R^{102b}$, wherein $R^{102b}$ is selected from the group consisting of 2,2-difluoroethyl, 2,2,2-trifluoroethyl, cyclopropyl, cyclopropylmethyl, allyl and propargyl.

In another more particular embodiment, the compound of formula I is a compound of formula IB, as defined above, or a stereoisomer or an agriculturally or veterinarily acceptable salt thereof, where however $R^{2a}$ is Cl, $R^{2b}$ is H, $R^{2c}$ is Cl, and $R^6$ is —$CH_2$—$R^8$, wherein $R^8$ is selected from following rings: E-1, E-7, E-19, E-44, E-47 and E-57, where in rings E-1, E-7, E-19, E-44, E-47 and E-57 k is 0.

In another more particular embodiment, the compound of formula I is a compound of formula IB, as defined above, or a stereoisomer or an agriculturally or veterinarily acceptable salt thereof, where however $R^{2a}$ is Cl, $R^{2b}$ is H, $R^{2c}$ is Cl, and $R^6$ is selected from rings F-9, F-44, F-46 and F-53; where in rings F-9, F-44 and F-46 k is 0; and is in particular selected from rings F-9, F-44, F-46 and F-53-1 with $R^{17}$=H, methyl, ethyl or 2,2,2-trifluoroethyl; where in rings F-9, F-44 and F-46 k is 0.

In another more particular embodiment, the compound of formula I is a compound of formula IB, as defined above, or a stereoisomer or an agriculturally or veterinarily acceptable salt thereof, where however $R^{2a}$ is Cl, $R^{2b}$ is H, $R^{2c}$ is Cl, and $R^6$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=$NOCH_3$.

In another more particular embodiment, the compound of formula I is a compound of formula IB, as defined above, or a stereoisomer or an agriculturally or veterinarily acceptable salt thereof, where however $R^{2a}$ is Cl, $R^{2b}$ is H, $R^{2c}$ is Cl, and $R^6$ is N(H)$R^{101b}$, wherein $R^{11b}$ is selected from —C(O)—N(H)—$CH_2CF_3$ and rings E-1 and E-7, where in rings E-1 and E-7 k is 0.

In another more particular embodiment, the compound of formula I is a compound of formula IC or an N-oxide, a stereoisomer or an agriculturally or veterinarily acceptable salt thereof

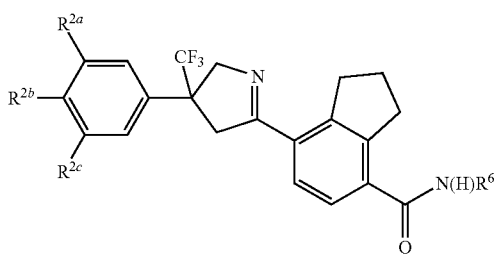

(IC)

wherein
$R^{2a}$ is Cl, $R^{2b}$ is F, $R^{2c}$ is Cl, and
$R^6$ is $CH_2$—$C(O)$—$N(H)$—$R^{102b}$, wherein
$R^{102b}$ is selected from the group consisting of 2,2-difluoroethyl, 2,2,2-trifluoroethyl, cyclopropyl, cyclopropylmethyl, allyl and propargyl.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is F, $R^{2c}$ is Cl, and
$R^6$ is —$CH_2$—$R^8$, wherein
$R^8$ is selected from following rings: E-1, E-7, E-19, E-44, E-47 and E-57, where in rings E-1, E-7, E-19, E-44, E-47 and E-57 k is 0.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is F, $R^{2c}$ is Cl, and
$R^6$ is selected from rings F-9, F-44, F-46 and F-53, where in rings F-9, F-44 and F-46 k is 0, and is in particular selected from rings F-9, F-44, F-46 and F-53-1 with $R^{17}$=H, methyl, ethyl or 2,2,2-trifluoroethyl; where in rings F-9, F-44 and F-46 k is 0.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is F, $R^{2c}$ is Cl, and
$R^6$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=NOCH$_3$.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is F, $R^{2c}$ is Cl, and
$R^6$ is N(H)$R^{101b}$, wherein
$R^{101b}$ is selected from —C(O)—N(H)—CH$_2$CF$_3$ and rings E-1 and E-7, where in rings E-1 and E-7 k is 0.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is H, $R^{2c}$ is Cl, and
$R^6$ is $CH_2$—$C(O)$—$N(H)$—$R^{102b}$, wherein
$R^{102b}$ is selected from the group consisting of 2,2-difluoroethyl, 2,2,2-trifluoroethyl, cyclopropyl, cyclopropylmethyl, allyl and propargyl.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is H, $R^{2c}$ is Cl, and
$R^6$ is —$CH_2$—$R^8$, wherein
$R^8$ is selected from following rings: E-1, E-7, E-19, E-44, E-47 and E-57, where in rings E-1, E-7, E-19, E-44, E-47 and E-57 k is 0.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is H, $R^{2c}$ is Cl, and
$R^6$ is selected from rings F-9, F-44, F-46 and F-53, where in rings F-9, F-44 and F-46 k is 0, and is in particular selected from rings F-9, F-44, F-46 and F-53-1 with $R^{17}$=H, methyl, ethyl or 2,2,2-trifluoroethyl; where in rings F-9, F-44 and F-46 k is 0.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is H, $R^{2c}$ is Cl, and
$R^6$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=NOCH$_3$.

In another more particular embodiment, the compound of formula I is a compound of formula IC, as defined above, or an N-oxide, a stereoisomer or an agriculturally or veterinarily acceptable salt thereof, where however
$R^{2a}$ is Cl, $R^{2b}$ is H, $R^{2c}$ is Cl, and
$R^6$ is N(H)$R^{101b}$, wherein
$R^{101b}$ is selected from —C(O)—N(H)—CH$_2$CF$_3$ and rings E-1 and E-7, where in rings E-1 and E-7 k is 0.

Examples of preferred compounds are compounds of the following formulae Ia.1 to Ia.4, where $R^{2a}$, $R^{2b}$ and $R^{2c}$ have one of the general or preferred meanings given above for $R^2$ and the other variables have one of the general or preferred meanings given above. Examples of preferred compounds are the individual compounds compiled in the tables 1 to 7292 below. Moreover, the meanings mentioned below for the individual variables in the tables are per se, independently of the combination in which they are mentioned, a particularly preferred embodiment of the substituents in question.

(Ia.1)

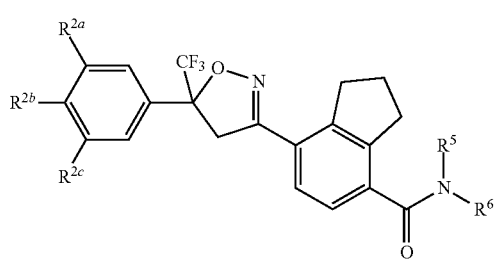

(Ia.2)

(Ia.3)

(Ia.4)

Table 1
Compounds of the formula Ia.1 in which $R^6$ is hydrogen, $R^5$ is hydrogen, and the combination of $R^{2a}$, $R^{2b}$ and $R^{2c}$ for a compound corresponds in each case to one row of Table A Table 2
Compounds of the formula Ia.1 in which $R^6$ is —CN, $R^5$ is hydrogen, and the combination of $R^{2a}$, $R^{2b}$ and $R^{2c}$ for a compound corresponds in each case to one row of Table A Table 3
Compounds of the formula Ia.1 in which $R^6$ is methyl, $R^5$ is hydrogen, and the combination of $R^{2a}$, $R^{2b}$ and $R^{2c}$ for a compound corresponds in each case to one row of Table A Table 4
Compounds of the formula Ia.1 in which $R^6$ is ethyl, $R^5$ is hydrogen, and the combination of $R^{2a}$, $R^{2b}$ and $R^{2c}$ for a compound corresponds in each case to one row of Table A Table 5
Compounds of the formula Ia.1 in which $R^6$ is n-propyl, $R^5$ is hydrogen, and the combination of $R^{2a}$, $R^{2b}$ and $R^{2c}$ for a compound corresponds in each case to one row of Table A Table 6
Compounds of the formula Ia.1 in which $R^6$ is isopropyl, $R^5$ is hydrogen, and the combination of $R^{2a}$, $R^{2b}$ and $R^{2c}$ for a compound corresponds in each case to one row of Table A Table 7
Compounds of the formula Ia.1 in which $R^6$ is n-butyl, $R^5$ is hydrogen, and the combination of $R^{2a}$, $R^{2b}$ and $R^{2c}$ for a compound corresponds in each case to one row of Table A Table 8
Compounds of the formula Ia.1 in which $R^6$ is sec-butyl, $R^5$ is hydrogen, and the combination of $R^{2a}$, $R^{2b}$ and $R^{2c}$ for a compound corresponds in each case to one row of Table A Table 9
Compounds of the formula Ia.1 in which $R^6$ is isobutyl, $R^5$ is hydrogen, and the combination of $R^{2a}$, $R^{2b}$ and $R^{2c}$ for a compound corresponds in each case to one row of Table A Table 10
Compounds of the formula Ia.1 in which $R^6$ is tert-butyl, $R^5$ is hydrogen, and the combination of $R^{2a}$, $R^{2b}$ and $R^{2c}$ for a compound corresponds in each case to one row of Table A Table 11
Compounds of the formula Ia.1 in which $R^6$ is $CH_2$—C$(CH_3)_3$, $R^5$ is hydrogen, and the combination of $R^{2a}$, $R^{2b}$ and $R^{2c}$ for a compound corresponds in each case to one row of Table A Table 12
Compounds of the formula Ia.1 in which $R^6$ is —$CH_2CN$, $R^5$ is hydrogen, and the combination of $R^{2a}$, $R^{2b}$ and $R^{2c}$ for a compound corresponds in each case to one row of Table A Table 13
Compounds of the formula Ia.1 in which $R^6$ is —CH=$CH_2$, $R^5$ is hydrogen, and the combination of $R^{2a}$, $R^{2b}$ and $R^{2c}$ for a compound corresponds in each case to one row of Table A Table 14
Compounds of the formula Ia.1 in which $R^6$ is —$CH_2$—CH=$CH_2$, $R^5$ is hydrogen, and the combination of $R^{2a}$, $R^{2b}$ and $R^{2c}$ for a compound corresponds in each case to one row of Table A Table 15
Compounds of the formula Ia.1 in which $R^6$ is —$CH_2$—$CH_2$—CH=$CH_2$, $R^5$ is hydrogen, and the combination of $R^{2a}$, $R^{2b}$ and $R^{2c}$ for a compound corresponds in each case to one row of Table A Table 16
Compounds of the formula Ia.1 in which $R^6$ is —$CH_2$—CH=CH—$CH_3$, $R^5$ is hydrogen, and the combination of $R^{2a}$, $R^{2b}$ and $R^{2c}$ for a compound corresponds in each case to one row of Table A Table 17
Compounds of the formula Ia.1 in which $R^6$ is —$CH_2$—CCl=$CCl_2$, $R^5$ is hydrogen, and the combination of $R^{2a}$, $R^{2b}$ and $R^{2c}$ for a compound corresponds in each case to one row of Table A Table 18
Compounds of the formula Ia.1 in which $R^6$ is —C≡CH, $R^5$ is hydrogen, and the combination of $R^{2a}$, $R^{2b}$ and $R^{2c}$ for a compound corresponds in each case to one row of Table A Table 19
Compounds of the formula Ia.1 in which $R^6$ is —$CH_2$C≡CH, $R^5$ is hydrogen, and the combination of $R^{2a}$, $R^{2b}$ and $R^{2c}$ for a compound corresponds in each case to one row of Table A Table 20
Compounds of the formula Ia.1 in which $R^6$ is —$CH_2CH_2$C≡CH, $R^5$ is hydrogen, and the combination of $R^{2a}$, $R^{2b}$ and $R^{2c}$ for a compound corresponds in each case to one row of Table A Table 21
Compounds of the formula Ia.1 in which $R^6$ is —$CH_2CH_2OH$, $R^5$ is hydrogen, and the combination of $R^{2a}$, $R^{2b}$ and $R^{2c}$ for a compound corresponds in each case to one row of Table A Table 22
Compounds of the formula Ia.1 in which $R^6$ is —$CH_2CH_2OCH_3$, $R^5$ is hydrogen, and the combination of $R^{2a}$, $R^{2b}$ and $R^{2c}$ for a compound corresponds in each case to one row of Table A Table 23
Compounds of the formula Ia.1 in which $R^6$ is —CH$_2$CH$_2$OCH$_2$CH$_3$, $R^5$ is hydrogen, and the combination of $R^{2a}$, $R^{2b}$ and $R^{2c}$ for a compound corresponds in each case to one row of Table A Table 24
Compounds of the formula Ia.1 in which $R^6$ is —CH$_2$CH$_2$OCH$_2$CH=CH$_2$, $R^5$ is hydrogen, and the combination of $R^{2a}$, $R^{2b}$ and $R^{2c}$ for a compound corresponds in each case to one row of Table A Table 25
Compounds of the formula Ia.1 in which $R^6$ is —CH$_2$CH$_2$OCH$_2$C≡CH, $R^5$ is hydrogen, and the combination of $R^{2a}$, $R^{2b}$ and $R^{2c}$ for a compound corresponds in each case to one row of Table A Table 26
Compounds of the formula Ia.1 in which $R^6$ is —CH$_2$CH$_2$OCH$_2$-cyclopropyl, $R^5$ is hydrogen, and the combination of $R^{2a}$, $R^{2b}$ and $R^{2c}$ for a compound corresponds in each case to one row of Table A Table 27
Compounds of the formula Ia.1 in which $R^6$ is —CH$_2$CH$_2$OCF$_3$, $R^5$ is hydrogen, and the combination of $R^{2a}$, $R^{2b}$ and $R^{2c}$ for a compound corresponds in each case to one row of Table A Table 28
Compounds of the formula Ia.1 in which $R^6$ is —CH$_2$CH$_2$OCH$_2$CF$_3$, $R^5$ is hydrogen, and the combination of $R^{2a}$, $R^{2b}$ and $R^{2c}$ for a compound corresponds in each case to one row of Table A Table 29
Compounds of the formula Ia.1 in which $R^6$ is —CH$_2$CH$_2$SCH$_3$, $R^5$ is hydrogen, and the combination of $R^{2a}$, $R^{2b}$ and $R^{2c}$ for a compound corresponds in each case to one row of Table A Table 30
Compounds of the formula Ia.1 in which $R^6$ is —CH$_2$CH$_2$S(O)CH$_3$, $R^5$ is hydrogen, and the combination of $R^{2a}$, $R^{2b}$ and $R^{2c}$ for a compound corresponds in each case to one row of Table A Table 31
Compounds of the formula Ia.1 in which $R^6$ is —CH$_2$CH$_2$S(O)$_2$CH$_3$, $R^5$ is hydrogen, and the combination of $R^{2a}$, $R^{2b}$ and $R^{2c}$ for a compound corresponds in each case to one row of Table A Table 32
Compounds of the formula Ia.1 in which $R^6$ is —CH$_2$CH$_2$SCH$_2$CH$_3$, $R^5$ is hydrogen, and the combination of $R^{2a}$, $R^{2b}$ and $R^{2c}$ for a compound corresponds in each case to one row of Table A Table 33
Compounds of the formula Ia.1 in which $R^6$ is —CH$_2$CH$_2$S(O)CH$_2$CH$_3$, $R^5$ is hydrogen, and the combination of $R^{2a}$, $R^{2b}$ and $R^{2c}$ for a compound corresponds in each case to one row of Table A Table 34
Compounds of the formula Ia.1 in which $R^6$ is —CH$_2$CH$_2$S(O)$_2$CH$_2$CH$_3$, $R^5$ is hydrogen, and the combination of $R^{2a}$, $R^{2b}$ and $R^{2c}$ for a compound corresponds in each case to one row of Table A Table 35
Compounds of the formula Ia.1 in which $R^6$ is —CH$_2$CH$_2$S(O)$_2$CH$_2$CH=CH$_2$, $R^5$ is hydrogen, and the combination of $R^{2a}$, $R^{2b}$ and $R^{2c}$ for a compound corresponds in each case to one row of Table A Table 36
Compounds of the formula Ia.1 in which $R^6$ is —CH$_2$CH$_2$S(O)$_2$CH$_2$C≡CH, $R^5$ is hydrogen, and the combination of $R^{2a}$, $R^{2b}$ and $R^{2c}$ for a compound corresponds in each case to one row of Table A Table 37
Compounds of the formula Ia.1 in which $R^6$ is —CH$_2$CH$_2$S(O)$_2$CH$_2$-cyclopropyl, $R^5$ is hydrogen, and the combination of $R^{2a}$, $R^{2b}$ and $R^{2c}$ for a compound corresponds in each case to one row of Table A Table 38
Compounds of the formula Ia.1 in which $R^6$ is —CH$_2$CH$_2$SCF$_3$, $R^5$ is hydrogen, and the combination of $R^{2a}$, $R^{2b}$ and $R^{2c}$ for a compound corresponds in each case to one row of Table A Table 39
Compounds of the formula Ia.1 in which $R^6$ is —CH$_2$CH$_2$S(O)CF$_3$, $R^5$ is hydrogen, and the combination of $R^{2a}$, $R^{2b}$ and $R^{2c}$ for a compound corresponds in each case to one row of Table A Table 40
Compounds of the formula Ia.1 in which $R^6$ is CH$_2$CH$_2$F, $R^5$ is hydrogen, and the combination of $R^{2a}$, $R^{2b}$ and $R^{2c}$ for a compound corresponds in each case to one row of Table A Table 41
Compounds of the formula Ia.1 in which $R^6$ is CH$_2$CHF$_2$, $R^5$ is hydrogen, and the combination of $R^{2a}$, $R^{2b}$ and $R^{2c}$ for a compound corresponds in each case to one row of Table A Table 42
Compounds of the formula Ia.1 in which $R^6$ is CH$_2$CF$_3$, $R^5$ is hydrogen, and the combination of $R^{2a}$, $R^{2b}$ and $R^{2c}$ for a compound corresponds in each case to one row of Table A Table 43
Compounds of the formula Ia.1 in which $R^6$ is CH$_2$CH$_2$CHF$_2$, $R^5$ is hydrogen, and the combination of $R^{2a}$, $R^{2b}$ and $R^{2c}$ for a compound corresponds in each case to one row of Table A Table 44
Compounds of the formula Ia.1 in which $R^6$ is CH$_2$CH$_2$CF$_3$, $R^5$ is hydrogen, and the combination of $R^{2a}$, $R^{2b}$ and $R^{2c}$ for a compound corresponds in each case to one row of Table A Table 45
Compounds of the formula Ia.1 in which $R^6$ is CH(CH$_3$)CF$_3$, $R^5$ is hydrogen, and the combination of $R^{2a}$, $R^{2b}$ and $R^{2c}$ for a compound corresponds in each case to one row of Table A Table 46
Compounds of the formula Ia.1 in which $R^6$ is CH(CF$_3$)$_2$, $R^5$ is hydrogen, and the combination of $R^{2a}$, $R^{2b}$ and $R^{2c}$ for a compound corresponds in each case to one row of Table A Table 47
Compounds of the formula Ia.1 in which $R^6$ is CH$_2$CH$_2$CH$_2$CF$_3$, $R^5$ is hydrogen, and the combination of $R^{2a}$, $R^{2b}$ and $R^{2c}$ for a compound corresponds in each case to one row of Table A Table 48
Compounds of the formula Ia.1 in which $R^6$ is cyclopropyl, $R^5$ is hydrogen, and the combination of $R^{2a}$, $R^{2b}$ and $R^{2c}$ for a compound corresponds in each case to one row of Table A Table 49
Compounds of the formula Ia.1 in which $R^6$ is 1-cyano-cyclopropyl, $R^5$ is hydrogen, and the combination of $R^{2a}$, $R^{2b}$ and $R^{2c}$ for a compound corresponds in each case to one row of Table A Table 50
Compounds of the formula Ia.1 in which $R^6$ is 1-(pyridin-2-yl)-cyclopropyl, $R^5$ is hydrogen, and the combination of $R^{2a}$, $R^{2b}$ and $R^{2c}$ for a compound corresponds in each case to one row of Table A Table 51
Compounds of the formula Ia.1 in which $R^6$ is 2,2-difluorocyclopropyl, $R^5$ is hydrogen, and the combination of $R^{2a}$, $R^{2b}$ and $R^{2c}$ for a compound corresponds in each case to one row of Table A Table 52
Compounds of the formula Ia.1 in which $R^6$ is cyclobutyl, $R^5$ is hydrogen, and the combination of $R^{2a}$, $R^{2b}$ and $R^{2c}$ for a compound corresponds in each case to one row of Table A Table 53
Compounds of the formula Ia.1 in which $R^6$ is 1-cyanocyclobutyl, $R^5$ is hydrogen, and the combination of $R^{2a}$, $R^{2b}$ and $R^{2c}$ for a compound corresponds in each case to one row of Table A Table 54
Compounds of the formula Ia.1 in which $R^6$ is 3,3-difluorocyclobutyl, $R^5$ is hydrogen, and the combination of $R^{2a}$, $R^{2b}$ and $R^{2c}$ for a compound corresponds in each case to one row of Table A Table 55
Compounds of the formula Ia.1 in which $R^6$ is cyclopentyl, $R^5$ is hydrogen, and the combination of $R^{2a}$, $R^{2b}$ and $R^{2c}$ for a compound corresponds in each case to one row of Table A Table 56
Compounds of the formula Ia.1 in which $R^6$ is 1-cyanocyclopentyl, $R^5$ is hydrogen, and the combination of $R^{2a}$, $R^{2b}$ and $R^{2c}$ for a compound corresponds in each case to one row of Table A Table 57
Compounds of the formula Ia.1 in which $R^6$ is cyclohexyl, $R^5$ is hydrogen, and the combination of $R^{2a}$, $R^{2b}$ and $R^{2c}$ for a compound corresponds in each case to one row of Table A Table 58
Compounds of the formula Ia.1 in which $R^6$ is 1-cyanocyclohexyl, $R^5$ is hydrogen, and the combination of $R^{2a}$, $R^{2b}$ and $R^{2c}$ for a compound corresponds in each case to one row of Table A Table 59
Compounds of the formula Ia.1 in which $R^6$ is —$CH_2$-cyclopropyl, $R^5$ is hydrogen, and the combination of $R^{2a}$, $R^{2b}$ and $R^{2c}$ for a compound corresponds in each case to one row of Table A Table 60
Compounds of the formula Ia.1 in which $R^6$ is —$CH_2$-(1-cyano-cyclopropyl), $R^5$ is hydrogen, and the combination of $R^{2a}$, $R^{2b}$ and $R^{2c}$ for a compound corresponds in each case to one row of Table A Table 61
Compounds of the formula Ia.1 in which $R^6$ is —$CH_2$-(1-fluoro-cyclopropyl), $R^5$ is hydrogen, and the combination of $R^{2a}$, $R^{2b}$ and $R^{2c}$ for a compound corresponds in each case to one row of Table A Table 62
Compounds of the formula Ia.1 in which $R^6$ is —$CH_2$-(1-chloro-cyclopropyl), $R^5$ is hydrogen, and the combination of $R^{2a}$, $R^{2b}$ and $R^{2c}$ for a compound corresponds in each case to one row of Table A Table 63
Compounds of the formula Ia.1 in which $R^6$ is —$CH_2$-(1-bromo-cyclopropyl), $R^5$ is hydrogen, and the combination of $R^{2a}$, $R^{2b}$ and $R^{2c}$ for a compound corresponds in each case to one row of Table A Table 64
Compounds of the formula Ia.1 in which $R^6$ is —$CH_2$-(2,2-difluorocyclopropyl), $R^5$ is hydrogen, and the combination of $R^{2a}$, $R^{2b}$ and $R^{2c}$ for a compound corresponds in each case to one row of Table A Table 65
Compounds of the formula Ia.1 in which $R^6$ is —$CH_2$-(2,2-dichlorocyclopropyl), $R^5$ is hydrogen, and the combination of $R^{2a}$, $R^{2b}$ and $R^{2c}$ for a compound corresponds in each case to one row of Table A Table 66
Compounds of the formula Ia.1 in which $R^6$ is —$CH_2$-(2,2-dibromocyclopropyl), $R^5$ is hydrogen, and the combination of $R^{2a}$, $R^{2b}$ and $R^{2c}$ for a compound corresponds in each case to one row of Table A Table 67
Compounds of the formula Ia.1 in which $R^6$ is —$CH_2$-(1-(difluoromethyl)-cyclopropyl), $R^5$ is hydrogen, and the combination of $R^{2a}$, $R^{2b}$ and $R^{2c}$ for a compound corresponds in each case to one row of Table A Table 68
Compounds of the formula Ia.1 in which $R^6$ is —$CH_2$-(1-(trifluoromethyl)-cyclopropyl), $R^5$ is hydrogen, and the combination of $R^{2a}$, $R^{2b}$ and $R^{2c}$ for a compound corresponds in each case to one row of Table A Table 69
Compounds of the formula Ia.1 in which $R^6$ is —$CH_2$-cyclobutyl, $R^5$ is hydrogen, and the combination of $R^{2a}$, $R^{2b}$ and $R^{2c}$ for a compound corresponds in each case to one row of Table A Table 70
Compounds of the formula Ia.1 in which $R^6$ is —$CH_2$-(1-cyano-cyclobutyl), $R^5$ is hydrogen, and the combination of $R^{2a}$, $R^{2b}$ and $R^{2c}$ for a compound corresponds in each case to one row of Table A Table 71
Compounds of the formula Ia.1 in which $R^6$ is —$CH_2$-(1-fluoro-cyclobutyl), $R^5$ is hydrogen, and the combination of $R^{2a}$, $R^{2b}$ and $R^{2c}$ for a compound corresponds in each case to one row of Table A Table 72
Compounds of the formula Ia.1 in which $R^6$ is —$CH_2$-(1-chloro-cyclobutyl), $R^5$ is hydrogen, and the combination of $R^{2a}$, $R^{2b}$ and $R^{2c}$ for a compound corresponds in each case to one row of Table A Table 73
Compounds of the formula Ia.1 in which $R^6$ is —$CH_2$-(2,2-difluorocyclobutyl), $R^5$ is hydrogen, and the combination of $R^{2a}$, $R^{2b}$ and $R^{2c}$ for a compound corresponds in each case to one row of Table A Table 74
Compounds of the formula Ia.1 in which $R^6$ is —$CH_2$-(3,3-difluorocyclobutyl), $R^5$ is hydrogen, and the combination of $R^{2a}$, $R^{2b}$ and $R^{2c}$ for a compound corresponds in each case to one row of Table A Table 75
Compounds of the formula Ia.1 in which $R^6$ is is —$CH_2$-(2,2,3,3-tetrafluorocyclobutyl), $R^5$ is hydrogen, and the combination of $R^{2a}$, $R^{2b}$ and $R^{2c}$ for a compound corresponds in each case to one row of Table A Table 76
Compounds of the formula Ia.1 in which $R^6$ is —$CH_2$-(2,2,3,3,4,4-hexafluorocyclobutyl), $R^5$ is hydrogen, and the combination of $R^{2a}$, $R^{2b}$ and $R^{2c}$ for a compound corresponds in each case to one row of Table A Table 77
Compounds of the formula Ia.1 in which $R^6$ is —$CH_2$-cyclopentyl, $R^5$ is hydrogen, and the combination of $R^{2a}$, $R^{2b}$ and $R^{2c}$ for a compound corresponds in each case to one row of Table A Table 78
Compounds of the formula Ia.1 in which $R^6$ is —CH$_2$-(-1-fluoro-cyclopentyl), $R^5$ is hydrogen, and the combination of $R^{2a}$, $R^{2b}$ and $R^{2c}$ for a compound corresponds in each case to one row of Table A Table 79
Compounds of the formula Ia.1 in which $R^6$ is —CH$_2$-(1-chloro-cyclopentyl), $R^5$ is hydrogen, and the combination of $R^{2a}$, $R^{2b}$ and $R^{2c}$ for a compound corresponds in each case to one row of Table A Table 80
Compounds of the formula Ia.1 in which $R^6$ is —CH$_2$-(1-cyano-cyclopentyl), $R^5$ is hydrogen, and the combination of $R^{2a}$, $R^{2b}$ and $R^{2c}$ for a compound corresponds in each case to one row of Table A Table 81
Compounds of the formula Ia.1 in which $R^6$ is —CH$_2$-(2,2-difluorocyclopentyl), $R^5$ is hydrogen, and the combination of $R^{2a}$, $R^{2b}$ and $R^{2c}$ for a compound corresponds in each case to one row of Table A Table 82
Compounds of the formula Ia.1 in which $R^6$ is —CH$_2$-(3,3-difluorocyclopentyl), $R^5$ is hydrogen, and the combination of $R^{2a}$, $R^{2b}$ and $R^{2c}$ for a compound corresponds in each case to one row of Table A Table 83
Compounds of the formula Ia.1 in which $R^6$ is —CH$_2$-cyclohexyl, $R^5$ is hydrogen, and the combination of $R^{2a}$, $R^{2b}$ and $R^{2c}$ for a compound corresponds in each case to one row of Table A Table 84
Compounds of the formula Ia.1 in which $R^6$ is —CH$_2$-(1-fluorocyclohexyl), $R^5$ is hydrogen, and the combination of $R^{2a}$, $R^{2b}$ and $R^{2c}$ for a compound corresponds in each case to one row of Table A Table 85
Compounds of the formula Ia.1 in which $R^6$ is —CH$_2$-(1-chlorocyclohexyl), $R^5$ is hydrogen, and the combination of $R^{2a}$, $R^{2b}$ and $R^{2c}$ for a compound corresponds in each case to one row of Table A Table 86
Compounds of the formula Ia.1 in which $R^6$ is —CH$_2$-(1-cyanocyclohexyl), $R^5$ is hydrogen, and the combination of $R^{2a}$, $R^{2b}$ and $R^{2c}$ for a compound corresponds in each case to one row of Table A Table 87
Compounds of the formula Ia.1 in which $R^6$ is thietan-3-yl, $R^5$ is hydrogen, and the combination of $R^{2a}$, $R^{2b}$ and $R^{2c}$ for a compound corresponds in each case to one row of Table A Table 88
Compounds of the formula Ia.1 in which $R^6$ is 1-oxo-thietan-3-yl, $R^5$ is hydrogen, and the combination of $R^{2a}$, $R^{2b}$ and $R^{2c}$ for a compound corresponds in each case to one row of Table A Table 89
Compounds of the formula Ia.1 in which $R^6$ is 1,1-dioxo-thietan-3-yl, $R^5$ is hydrogen, and the combination of $R^{2a}$, $R^{2b}$ and $R^{2c}$ for a compound corresponds in each case to one row of Table A Table 90
Compounds of the formula Ia.1 in which $R^6$ is 3-methyl-thietan-3-yl, $R^5$ is hydrogen, and the combination of $R^{2a}$, $R^{2b}$ and $R^{2c}$ for a compound corresponds in each case to one row of Table A Table 91
Compounds of the formula Ia.1 in which $R^6$ is 2,2-dimethyl-thietan-3-yl, $R^5$ is hydrogen, and the combination of $R^{2a}$, $R^{2b}$ and $R^{2c}$ for a compound corresponds in each case to one row of Table A Table 92
Compounds of the formula Ia.1 in which $R^6$ is 3-methyl-1-oxo-thietan-3-yl, $R^5$ is hydrogen, and the combination of $R^{2a}$, $R^{2b}$ and $R^{2c}$ for a compound corresponds in each case to one row of Table A Table 93
Compounds of the formula Ia.1 in which $R^6$ is 2,2-dimethyl-1-oxo-thietan-3-yl, $R^5$ is hydrogen, and the combination of $R^{2a}$, $R^{2b}$ and $R^{2c}$ for a compound corresponds in each case to one row of Table A Table 94
Compounds of the formula Ia.1 in which $R^6$ is 3-methyl-1,1-dioxo-thietan-3-yl, $R^5$ is hydrogen, and the combination of $R^{2a}$, $R^{2b}$ and $R^{2c}$ for a compound corresponds in each case to one row of Table A Table 95
Compounds of the formula Ia.1 in which $R^6$ is 2,2-dimethyl-1,1-dioxo-thietan-3-yl, $R^5$ is hydrogen, and the combination of $R^{2a}$, $R^{2b}$ and $R^{2c}$ for a compound corresponds in each case to one row of Table A Table 96
Compounds of the formula Ia.1 in which $R^6$ is —CH$_2$-thietan-3-yl, $R^5$ is hydrogen, and the combination of $R^{2a}$, $R^{2b}$ and $R^{2c}$ for a compound corresponds in each case to one row of Table A Table 97
Compounds of the formula Ia.1 in which $R^6$ is —CH$_2$-(1-oxo-thietan-3-yl), $R^5$ is hydrogen, and the combination of $R^{2a}$, $R^{2b}$ and $R^{2c}$ for a compound corresponds in each case to one row of Table A Table 98
Compounds of the formula Ia.1 in which $R^6$ is —CH$_2$-(1,1-dioxo-thietan-3-yl), $R^5$ is hydrogen, and the combination of $R^{2a}$, $R^{2b}$ and $R^{2c}$ for a compound corresponds in each case to one row of Table A Table 99
Compounds of the formula Ia.1 in which $R^6$ is —CH$_2$-thietan-2-yl, $R^5$ is hydrogen, and the combination of $R^{2a}$, $R^{2b}$ and $R^{2c}$ for a compound corresponds in each case to one row of Table A Table 100
Compounds of the formula Ia.1 in which $R^6$ is —CH$_2$-(1-oxo-thietan-2-yl), $R^5$ is hydrogen, and the combination of $R^{2a}$, $R^{2b}$ and $R^{2c}$ for a compound corresponds in each case to one row of Table A Table 101
Compounds of the formula Ia.1 in which $R^6$ is —CH$_2$-(1,1-dioxo-thietan-2-yl), $R^5$ is hydrogen, and the combination of $R^{2a}$, $R^{2b}$ and $R^{2c}$ for a compound corresponds in each case to one row of Table A Table 102
Compounds of the formula Ia.1 in which $R^6$ is tetrahydro-thiophen-3-yl, $R^5$ is hydrogen, and the combination of $R^{2a}$, $R^{2b}$ and $R^{2c}$ for a compound corresponds in each case to one row of Table A Table 103
Compounds of the formula Ia.1 in which $R^6$ is 1-oxo-tetrahydrothiophen-3-yl, $R^5$ is hydrogen, and the combination of $R^{2a}$, $R^{2b}$ and $R^{2c}$ for a compound corresponds in each case to one row of Table A Table 104
Compounds of the formula Ia.1 in which $R^6$ is 1,1-dioxo-tetrahydrothiophen-3-yl, $R^5$ is hydrogen, and the combination of $R^{2a}$, $R^{2b}$ and $R^{2c}$ for a compound corresponds in each case to one row of Table A Table 105
Compounds of the formula Ia.1 in which $R^6$ is phenyl, $R^5$ is hydrogen, and the combination of $R^{2a}$, $R^{2b}$ and $R^{2c}$ for a compound corresponds in each case to one row of Table A Table 106
Compounds of the formula Ia.1 in which $R^6$ is 2-fluorophenyl, $R^5$ is hydrogen, and the combination of $R^{2a}$, $R^{2b}$ and $R^{2c}$ for a compound corresponds in each case to one row of Table A Table 107
Compounds of the formula Ia.1 in which $R^6$ is pyridin-2-yl, $R^5$ is hydrogen, and the combination of $R^{2a}$, $R^{2b}$ and $R^{2c}$ for a compound corresponds in each case to one row of Table A Table 108
Compounds of the formula Ia.1 in which $R^6$ is pyridin-3-yl, $R^5$ is hydrogen, and the combination of $R^{2a}$, $R^{2b}$ and $R^{2c}$ for a compound corresponds in each case to one row of Table A Table 109
Compounds of the formula Ia.1 in which $R^6$ is pyridin-4-yl, $R^5$ is hydrogen, and the combination of $R^{2a}$, $R^{2b}$ and $R^{2c}$ for a compound corresponds in each case to one row of Table A Table 110
Compounds of the formula Ia.1 in which $R^6$ is pyrimidin-2-yl, $R^5$ is hydrogen, and the combination of $R^{2a}$, $R^{2b}$ and $R^{2c}$ for a compound corresponds in each case to one row of Table A Table 111
Compounds of the formula Ia.1 in which $R^6$ is pyrimidin-4-yl, $R^5$ is hydrogen, and the combination of $R^{2a}$, $R^{2b}$ and $R^{2c}$ for a compound corresponds in each case to one row of Table A Table 112
Compounds of the formula Ia.1 in which $R^6$ is pyrimidin-5-yl, $R^5$ is hydrogen, and the combination of $R^{2a}$, $R^{2b}$ and $R^{2c}$ for a compound corresponds in each case to one row of Table A Table 113
Compounds of the formula Ia.1 in which $R^6$ is pyrazin-2-yl, $R^5$ is hydrogen, and the combination of $R^{2a}$, $R^{2b}$ and $R^{2c}$ for a compound corresponds in each case to one row of Table A Table 114
Compounds of the formula Ia.1 in which $R^6$ is pyridazin-3-yl, $R^5$ is hydrogen, and the combination of $R^{2a}$, $R^{2b}$ and $R^{2c}$ for a compound corresponds in each case to one row of Table A Table 115
Compounds of the formula Ia.1 in which $R^6$ is pyridazin-4-yl, $R^5$ is hydrogen, and the combination of $R^{2a}$, $R^{2b}$ and $R^{2c}$ for a compound corresponds in each case to one row of Table A Table 116
Compounds of the formula Ia.1 in which $R^6$ is pyrazol-3-yl, $R^5$ is hydrogen, and the combination of $R^{2a}$, $R^{2b}$ and $R^{2c}$ for a compound corresponds in each case to one row of Table A Table 117
Compounds of the formula Ia.1 in which $R^6$ is 1-methylpyrazol-3-yl, $R^5$ is hydrogen, and the combination of $R^{2a}$, $R^{2b}$ and $R^{2c}$ for a compound corresponds in each case to one row of Table A Table 118
Compounds of the formula Ia.1 in which $R^6$ is thiazol-2-yl, $R^5$ is hydrogen, and the combination of $R^{2a}$, $R^{2b}$ and $R^{2c}$ for a compound corresponds in each case to one row of Table A Table 119
Compounds of the formula Ia.1 in which $R^6$ is 3-methylisothiazol-5-yl, $R^5$ is hydrogen, and the combination of $R^{2a}$, $R^{2b}$ and $R^{2c}$ for a compound corresponds in each case to one row of Table A Table 120
Compounds of the formula Ia.1 in which $R^6$ is oxetan-3-yl, $R^5$ is hydrogen, and the combination of $R^{2a}$, $R^{2b}$ and $R^{2c}$ for a compound corresponds in each case to one row of Table A Table 121
Compounds of the formula Ia.1 in which $R^6$ is tetrahydrofuran-2-yl, $R^5$ is hydrogen, and the combination of $R^{2a}$, $R^{2b}$ and $R^{2c}$ for a compound corresponds in each case to one row of Table A Table 122
Compounds of the formula Ia.1 in which $R^6$ is tetrahydrofuran-3-yl, $R^5$ is hydrogen, and the combination of $R^{2a}$, $R^{2b}$ and $R^{2c}$ for a compound corresponds in each case to one row of Table A Table 123
Compounds of the formula Ia.1 in which $R^6$ is 2-oxotetrahydrofuran-3-yl, $R^5$ is hydrogen, and the combination of $R^{2a}$, $R^{2b}$ and $R^{2c}$ for a compound corresponds in each case to one row of Table A Table 124
Compounds of the formula Ia.1 in which $R^6$ is 1-ethylpyrrolidin-3-yl, $R^5$ is hydrogen, and the combination of $R^{2a}$, $R^{2b}$ and $R^{2c}$ for a compound corresponds in each case to one row of Table A Table 125
Compounds of the formula Ia.1 in which $R^6$ is 2-oxopyrrolidin-3-yl, $R^5$ is hydrogen, and the combination of $R^{2a}$, $R^{2b}$ and $R^{2c}$ for a compound corresponds in each case to one row of Table A Table 126
Compounds of the formula Ia.1 in which $R^6$ is 1-methyl-2-oxopyrrolidin-3-yl, $R^5$ is hydrogen, and the combination of $R^{2a}$, $R^{2b}$ and $R^{2c}$ for a compound corresponds in each case to one row of Table A Table 127
Compounds of the formula Ia.1 in which $R^6$ is 1-ethyl-2-oxopyrrolidin-3-yl, $R^5$ is hydrogen, and the combination of $R^{2a}$, $R^{2b}$ and $R^{2c}$ for a compound corresponds in each case to one row of Table A Table 128
Compounds of the formula Ia.1 in which $R^6$ is 2-oxo-1-(2,2,2-trifluoroethyl)-pyrrolidin-3-yl, $R^5$ is hydrogen, and the combination of $R^{2a}$, $R^{2b}$ and $R^{2c}$ for a compound corresponds in each case to one row of Table A Table 129
Compounds of the formula Ia.1 in which $R^6$ is 3-oxo-isoxazolidin-4-yl, $R^5$ is hydrogen, and the combination of $R^{2a}$, $R^{2b}$ and $R^{2c}$ for a compound corresponds in each case to one row of Table A Table 130
Compounds of the formula Ia.1 in which $R^6$ is 2-methyl-3-oxo-isoxazolidin-4-yl, $R^5$ is hydrogen, and the combination of $R^{2a}$, $R^{2b}$ and $R^{2c}$ for a compound corresponds in each case to one row of Table A Table 131
Compounds of the formula Ia.1 in which $R^6$ is 2-ethyl-3-oxo-isoxazolidin-4-yl, $R^5$ is hydrogen, and the combination of $R^{2a}$, $R^{2b}$ and $R^{2c}$ for a compound corresponds in each case to one row of Table A Table 132
Compounds of the formula Ia.1 in which $R^6$ is 2-propyl-3-oxo-isoxazolidin-4-yl, $R^5$ is hydrogen, and the combination of $R^{2a}$, $R^{2b}$ and $R^{2c}$ for a compound corresponds in each case to one row of Table A Table 133
Compounds of the formula Ia.1 in which $R^6$ is 2-butyl-3-oxo-isoxazolidin-4-yl, $R^5$ is hydrogen, and the combination of $R^{2a}$, $R^{2b}$ and $R^{2c}$ for a compound corresponds in each case to one row of Table A Table 134
Compounds of the formula Ia.1 in which $R^6$ is 2-(but-2-yl)-3-oxo-isoxazolidin-4-yl, $R^5$ is hydrogen, and the combination of $R^{2a}$, $R^{2b}$ and $R^{2c}$ for a compound corresponds in each case to one row of Table A Table 135
Compounds of the formula Ia.1 in which $R^6$ is 2-(2-fluoroethyl)-3-oxo-isoxazolidin-4-yl, $R^5$ is hydrogen, and the combination of $R^{2a}$, $R^{2b}$ and $R^{2c}$ for a compound corresponds in each case to one row of Table A Table 136
Compounds of the formula Ia.1 in which $R^6$ is 2-(2,2-difluoroethyl)-3-oxo-isoxazolidin-4-yl, $R^5$ is hydrogen, and the combination of $R^{2a}$, $R^{2b}$ and $R^{2c}$ for a compound corresponds in each case to one row of Table A Table 137
Compounds of the formula Ia.1 in which $R^6$ is 2-(2,2,2-trifluoroethyl)-3-oxo-isoxazolidin-4-yl, $R^5$ is hydrogen, and the combination of $R^{2a}$, $R^{2b}$ and $R^{2c}$ for a compound corresponds in each case to one row of Table A Table 138
Compounds of the formula Ia.1 in which $R^6$ is 2-(3,3,3-trifluoropropyl)-3-oxo-isoxazolidin-4-yl, $R^5$ is hydrogen, and the combination of $R^{2a}$, $R^{2b}$ and $R^{2c}$ for a compound corresponds in each case to one row of Table A Table 139
Compounds of the formula Ia.1 in which $R^6$ is 1-methyl-5-oxo-1,2,4-triazol-4-yl, $R^5$ is hydrogen, and the combination of $R^{2a}$, $R^{2b}$ and $R^{2c}$ for a compound corresponds in each case to one row of Table A Table 140
Compounds of the formula Ia.1 in which $R^6$ is azetidin-3-yl, $R^5$ is hydrogen, and the combination of $R^{2a}$, $R^{2b}$ and $R^{2c}$ for a compound corresponds in each case to one row of Table A Table 141
Compounds of the formula Ia.1 in which $R^6$ is 1-acetyl-azetidin-3-yl, $R^5$ is hydrogen, and the combination of $R^{2a}$, $R^{2b}$ and $R^{2c}$ for a compound corresponds in each case to one row of Table A Table 142
Compounds of the formula Ia.1 in which $R^6$ is $NH_2$, $R^5$ is hydrogen, and the combination of $R^{2a}$, $R^{2b}$ and $R^{2c}$ for a compound corresponds in each case to one row of Table A Table 143
Compounds of the formula Ia.1 in which $R^6$ is —NH-phenyl, $R^5$ is hydrogen, and the combination of $R^{2a}$, $R^{2b}$ and $R^{2c}$ for a compound corresponds in each case to one row of Table A Table 144
Compounds of the formula Ia.1 in which $R^6$ is —NH-pyridin-2-yl, $R^5$ is hydrogen, and the combination of $R^{2a}$, $R^{2b}$ and $R^{2c}$ for a compound corresponds in each case to one row of Table A Table 145
Compounds of the formula Ia.1 in which $R^6$ is —NH-pyridin-3-yl, $R^5$ is hydrogen, and the combination of $R^{2a}$, $R^{2b}$ and $R^{2c}$ for a compound corresponds in each case to one row of Table A Table 146
Compounds of the formula Ia.1 in which $R^6$ is —NH-pyridin-4-yl, $R^5$ is hydrogen, and the combination of $R^{2a}$, $R^{2b}$ and $R^{2c}$ for a compound corresponds in each case to one row of Table A Table 147
Compounds of the formula Ia.1 in which $R^6$ is —NH-pyrimidin-2-yl, $R^5$ is hydrogen, and the combination of $R^{2a}$, $R^{2b}$ and $R^{2c}$ for a compound corresponds in each case to one row of Table A Table 148
Compounds of the formula Ia.1 in which $R^6$ is —NH-pyrimidin-4-yl, $R^5$ is hydrogen, and the combination of $R^{2a}$, $R^{2b}$ and $R^{2c}$ for a compound corresponds in each case to one row of Table A Table 149
Compounds of the formula Ia.1 in which $R^6$ is —NH-pyrimidin-5-yl, $R^5$ is hydrogen, and the combination of $R^{2a}$, $R^{2b}$ and $R^{2c}$ for a compound corresponds in each case to one row of Table A Table 150
Compounds of the formula Ia.1 in which $R^6$ is —N($CH_3$)-pyrimidin-2-yl, $R^5$ is hydrogen, and the combination of $R^{2a}$, $R^{2b}$ and $R^{2c}$ for a compound corresponds in each case to one row of Table A Table 151
Compounds of the formula Ia.1 in which $R^6$ is —$CH_2$—$COOCH_3$, $R^5$ is hydrogen, and the combination of $R^{2a}$, $R^{2b}$ and $R^{2c}$ for a compound corresponds in each case to one row of Table A Table 152
Compounds of the formula Ia.1 in which $R^6$ is —$CH_2$—COO—$CH_2CH_3$, $R^5$ is hydrogen, and the combination of $R^{2a}$, $R^{2b}$ and $R^{2c}$ for a compound corresponds in each case to one row of Table A Table 153
Compounds of the formula Ia.1 in which $R^6$ is —$CH_2$—$CONH_2$, $R^5$ is hydrogen, and the combination of $R^{2a}$, $R^{2b}$ and $R^{2c}$ for a compound corresponds in each case to one row of Table A Table 154
Compounds of the formula Ia.1 in which $R^6$ is —$CH_2$—CONH—$CH_3$, $R^5$ is hydrogen, and the combination of $R^{2a}$, $R^{2b}$ and $R^{2c}$ for a compound corresponds in each case to one row of Table A Table 155
Compounds of the formula Ia.1 in which $R^6$ is —$CH_2$—CONH—$CH_2CH_3$, $R^5$ is hydrogen, and the combination of $R^{2a}$, $R^{2b}$ and $R^{2c}$ for a compound corresponds in each case to one row of Table A Table 156
Compounds of the formula Ia.1 in which $R^6$ is —$CH_2$—CONH—$CH_2CH_2CH_3$, $R^5$ is hydrogen, and the combination of $R^{2a}$, $R^{2b}$ and $R^{2c}$ for a compound corresponds in each case to one row of Table A Table 157
Compounds of the formula Ia.1 in which $R^6$ is —$CH_2$—CONH-isopropyl, $R^5$ is hydrogen, and the combination of $R^{2a}$, $R^{2b}$ and $R^{2c}$ for a compound corresponds in each case to one row of Table A Table 158
Compounds of the formula Ia.1 in which $R^6$ is —$CH_2$—CONH—$CH_2CH_2F$, $R^5$ is hydrogen, and the combination of $R^{2a}$, $R^{2b}$ and $R^{2c}$ for a compound corresponds in each case to one row of Table A Table 159
Compounds of the formula Ia.1 in which $R^6$ is —$CH_2$—CONH—$CH_2CHF_2$, $R^5$ is hydrogen, and the combination of $R^{2a}$, $R^{2b}$ and $R^{2c}$ for a compound corresponds in each case to one row of Table A Table 160
Compounds of the formula Ia.1 in which $R^6$ is —$CH_2$—CONH—$CH_2CF_3$, $R^5$ is hydrogen, and the combination of $R^{2a}$, $R^{2b}$ and $R^{2c}$ for a compound corresponds in each case to one row of Table A Table 161
Compounds of the formula Ia.1 in which $R^6$ is —$CH_2$—CONH—$CH(CF_3)CH_3$, $R^5$ is hydrogen, and the combination of $R^{2a}$, $R^{2b}$ and $R^{2c}$ for a compound corresponds in each case to one row of Table A Table 162
Compounds of the formula Ia.1 in which $R^6$ is —$CH_2$—CONH—$CH(CF_3)_2$, $R^5$ is hydrogen, and the combination of $R^{2a}$, $R^{2b}$ and $R^{2c}$ for a compound corresponds in each case to one row of Table A Table 163
Compounds of the formula Ia.1 in which $R^6$ is —$CH_2$—CONH—$CH_2CH_2CHF_2$, $R^5$ is hydrogen, and the combination of $R^{2a}$, $R^{2b}$ and $R^{2c}$ for a compound corresponds in each case to one row of Table A Table 164
Compounds of the formula Ia.1 in which $R^6$ is —$CH_2$—CONH—$CH_2CH_2CF_3$, $R^5$ is hydrogen, and the combination of $R^{2a}$, $R^{2b}$ and $R^{2c}$ for a compound corresponds in each case to one row of Table A Table 165
Compounds of the formula Ia.1 in which $R^6$ is —CH($CH_3$)—CONH—$CH_2CF_3$, $R^5$ is hydrogen, and the combination of $R^{2a}$, $R^{2b}$ and $R^{2c}$ for a compound corresponds in each case to one row of Table A Table 166
Compounds of the formula Ia.1 in which $R^6$ is —$CH_2$—CONH-cyclopropyl, $R^5$ is hydrogen, and the combination of $R^{2a}$, $R^{2b}$ and $R^{2c}$ for a compound corresponds in each case to one row of Table A Table 167
Compounds of the formula Ia.1 in which $R^6$ is —$CH_2$—CONH—$CH_2CN$, $R^5$ is hydrogen, and the combination of $R^{2a}$, $R^{2b}$ and $R^{2c}$ for a compound corresponds in each case to one row of Table A Table 168
Compounds of the formula Ia.1 in which $R^6$ is —$CH_2$—CONH—$CH_2CH=CH_2$, $R^5$ is hydrogen, and the combination of $R^{2a}$, $R^{2b}$ and $R^{2c}$ for a compound corresponds in each case to one row of Table A Table 169
Compounds of the formula Ia.1 in which $R^6$ is —$CH_2$—CONH—$CH_2C\equiv CH$, $R^5$ is hydrogen, and the combination of $R^{2a}$, $R^{2b}$ and $R^{2c}$ for a compound corresponds in each case to one row of Table A Table 170
Compounds of the formula Ia.1 in which $R^6$ is —$CH_2$—CONH—$CH_2$-cyclopropyl, $R^5$ is hydrogen, and the combination of $R^{2a}$, $R^{2b}$ and $R^{2c}$ for a compound corresponds in each case to one row of Table A Table 171
Compounds of the formula Ia.1 in which $R^6$ is —$CH_2$—CONH—$CH_2$-(1-cyano-cyclopropyl), $R^5$ is hydrogen, and the combination of $R^{2a}$, $R^{2b}$ and $R^{2c}$ for a compound corresponds in each case to one row of Table A Table 172
Compounds of the formula Ia.1 in which $R^6$ is —$CH_2$—CONH-thietan-3-yl, $R^5$ is hydrogen, and the combination of $R^{2a}$, $R^{2b}$ and $R^{2c}$ for a compound corresponds in each case to one row of Table A Table 173
Compounds of the formula Ia.1 in which $R^6$ is —$CH_2$—CONH-1-oxo-thietan-3-yl, $R^5$ is hydrogen, and the combination of $R^{2a}$, $R^{2b}$ and $R^{2c}$ for a compound corresponds in each case to one row of Table A Table 174
Compounds of the formula Ia.1 in which $R^6$ is —$CH_2$—CONH-1,1-dioxo-thietan-3-yl, $R^5$ is hydrogen, and the combination of $R^{2a}$, $R^{2b}$ and $R^{2c}$ for a compound corresponds in each case to one row of Table A Table 175
Compounds of the formula Ia.1 in which $R^6$ is benzyl, $R^5$ is hydrogen, and the combination of $R^{2a}$, $R^{2b}$ and $R^{2c}$ for a compound corresponds in each case to one row of Table A Table 176
Compounds of the formula Ia.1 in which $R^6$ is pyridin-2-yl-methyl, $R^5$ is hydrogen, and the combination of $R^{2a}$, $R^{2b}$ and $R^{2c}$ for a compound corresponds in each case to one row of Table A Table 177
Compounds of the formula Ia.1 in which $R^6$ is pyridin-3-yl-methyl, $R^5$ is hydrogen, and the combination of $R^{2a}$, $R^{2b}$ and $R^{2c}$ for a compound corresponds in each case to one row of Table A Table 178
Compounds of the formula Ia.1 in which $R^6$ is pyridin-4-yl-methyl, $R^5$ is hydrogen, and the combination of $R^{2a}$, $R^{2b}$ and $R^{2c}$ for a compound corresponds in each case to one row of Table A Table 179
Compounds of the formula Ia.1 in which $R^6$ is 6-(trifluoromethyl)-pyridin-4-yl-methyl, $R^5$ is hydrogen, and the combination of $R^{2a}$, $R^{2b}$ and $R^{2c}$ for a compound corresponds in each case to one row of Table A Table 180
Compounds of the formula Ia.1 in which $R^6$ is pyrimidin-2-yl-methyl, $R^5$ is hydrogen, and the combination of $R^{2a}$, $R^{2b}$ and $R^{2c}$ for a compound corresponds in each case to one row of Table A Table 181
Compounds of the formula Ia.1 in which $R^6$ is pyrimidin-4-yl-methyl, $R^5$ is hydrogen, and the combination of $R^{2a}$, $R^{2b}$ and $R^{2c}$ for a compound corresponds in each case to one row of Table A Table 182
Compounds of the formula Ia.1 in which $R^6$ is pyrimidin-5-yl-methyl, $R^5$ is hydrogen, and the combination of $R^{2a}$, $R^{2b}$ and $R^{2c}$ for a compound corresponds in each case to one row of Table A Table 183
Compounds of the formula Ia.1 in which $R^6$ is (4-fluoropyrimidin-2-yl)-methyl, $R^5$ is hydrogen, and the combination of $R^{2a}$, $R^{2b}$ and $R^{2c}$ for a compound corresponds in each case to one row of Table A Table 184
Compounds of the formula Ia.1 in which $R^6$ is (5-fluoropyrimidin-2-yl)-methyl, $R^5$ is hydrogen, and the combination of $R^{2a}$, $R^{2b}$ and $R^{2c}$ for a compound corresponds in each case to one row of Table A Table 185
Compounds of the formula Ia.1 in which $R^6$ is (4-chloropyrimidin-2-yl)-methyl, $R^5$ is hydrogen, and the combination of $R^{2a}$, $R^{2b}$ and $R^{2c}$ for a compound corresponds in each case to one row of Table A Table 186
Compounds of the formula Ia.1 in which $R^6$ is (5-chloropyrimidin-2-yl)-methyl, $R^5$ is hydrogen, and the combination of $R^{2a}$, $R^{2b}$ and $R^{2c}$ for a compound corresponds in each case to one row of Table A Table 187
Compounds of the formula Ia.1 in which $R^6$ is (4-bromopyrimidin-2-yl)-methyl, $R^5$ is hydrogen, and the combination of $R^{2a}$, $R^{2b}$ and $R^{2c}$ for a compound corresponds in each case to one row of Table A Table 188
Compounds of the formula Ia.1 in which $R^6$ is (5-bromopyrimidin-2-yl)-methyl, $R^5$ is hydrogen, and the combination of $R^{2a}$, $R^{2b}$ and $R^{2c}$ for a compound corresponds in each case to one row of Table A Table 189
Compounds of the formula Ia.1 in which $R^6$ is (4-methylpyrimidin-2-yl)-methyl, $R^5$ is hydrogen, and the combination of $R^{2a}$, $R^{2b}$ and $R^{2c}$ for a compound corresponds in each case to one row of Table A Table 190
Compounds of the formula Ia.1 in which $R^6$ is (5-methylpyrimidin-2-yl)-methyl, $R^5$ is hydrogen, and the combination of $R^{2a}$, $R^{2b}$ and $R^{2c}$ for a compound corresponds in each case to one row of Table A Table 191
Compounds of the formula Ia.1 in which $R^6$ is (4,6-dimethylpyrimidin-2-yl)-methyl, $R^5$ is hydrogen, and the combination of $R^{2a}$, $R^{2b}$ and $R^{2c}$ for a compound corresponds in each case to one row of Table A Table 192
Compounds of the formula Ia.1 in which $R^6$ is (4-(trifluoromethyl)-pyrimidin-2-yl)-methyl, $R^5$ is hydrogen, and the combination of $R^{2a}$, $R^{2b}$ and $R^{2c}$ for a compound corresponds in each case to one row of Table A Table 193
Compounds of the formula Ia.1 in which $R^6$ is (5-(trifluoromethyl)-pyrimidin-2-yl)-methyl, $R^5$ is hydrogen, and the combination of $R^{2a}$, $R^{2b}$ and $R^{2c}$ for a compound corresponds in each case to one row of Table A Table 194
Compounds of the formula Ia.1 in which $R^6$ is (4,6-bis(trifluoromethyl)-pyrimidin-2-yl)-methyl, $R^5$ is hydrogen, and the combination of $R^{2a}$, $R^{2b}$ and $R^{2c}$ for a compound corresponds in each case to one row of Table A Table 195
Compounds of the formula Ia.1 in which $R^6$ is (4-methyl-6-(trifluoromethyl)-pyrimidin-2-yl)-methyl, $R^5$ is hydrogen, and the combination of $R^{2a}$, $R^{2b}$ and $R^{2c}$ for a compound corresponds in each case to one row of Table A Table 196
Compounds of the formula Ia.1 in which $R^6$ is pyridazin-3-yl-methyl, $R^5$ is hydrogen, and the combination of $R^{2a}$, $R^{2b}$ and $R^{2c}$ for a compound corresponds in each case to one row of Table A Table 197
Compounds of the formula Ia.1 in which $R^6$ is pyridazin-4-yl-methyl, $R^5$ is hydrogen, and the combination of $R^{2a}$, $R^{2b}$ and $R^{2c}$ for a compound corresponds in each case to one row of Table A Table 198
Compounds of the formula Ia.1 in which $R^6$ is pyrazin-2-yl-methyl, $R^5$ is hydrogen, and the combination of $R^{2a}$, $R^{2b}$ and $R^{2c}$ for a compound corresponds in each case to one row of Table A Table 199
Compounds of the formula Ia.1 in which $R^6$ is pyrazol-3-yl-methyl, $R^5$ is hydrogen, and the combination of $R^{2a}$, $R^{2b}$ and $R^{2c}$ for a compound corresponds in each case to one row of Table A Table 200
Compounds of the formula Ia.1 in which $R^6$ is 1-methyl-pyrazol-3-yl-methyl, $R^5$ is hydrogen, and the combination of $R^{2a}$, $R^{2b}$ and $R^{2c}$ for a compound corresponds in each case to one row of Table A Table 201
Compounds of the formula Ia.1 in which $R^6$ is 2-methyl-pyrazol-3-yl-methyl, $R^5$ is hydrogen, and the combination of $R^{2a}$, $R^{2b}$ and $R^{2c}$ for a compound corresponds in each case to one row of Table A Table 202
Compounds of the formula Ia.1 in which $R^6$ is thien-2-yl-methyl, $R^5$ is hydrogen, and the combination of $R^{2a}$, $R^{2b}$ and $R^{2c}$ for a compound corresponds in each case to one row of Table A Table 203
Compounds of the formula Ia.1 in which $R^6$ is thien-3-yl-methyl, $R^5$ is hydrogen, and the combination of $R^{2a}$, $R^{2b}$ and $R^{2c}$ for a compound corresponds in each case to one row of Table A Table 204
Compounds of the formula Ia.1 in which $R^6$ is thiazol-2-yl-methyl, $R^5$ is hydrogen, and the combination of $R^{2a}$, $R^{2b}$ and $R^{2c}$ for a compound corresponds in each case to one row of Table A Table 205
Compounds of the formula Ia.1 in which $R^6$ is thiazol-4-yl-methyl, $R^5$ is hydrogen, and the combination of $R^{2a}$, $R^{2b}$ and $R^{2c}$ for a compound corresponds in each case to one row of Table A Table 206
Compounds of the formula Ia.1 in which $R^6$ is thiazol-5-yl-methyl, $R^5$ is hydrogen, and the combination of $R^{2a}$, $R^{2b}$ and $R^{2c}$ for a compound corresponds in each case to one row of Table A Table 207
Compounds of the formula Ia.1 in which $R^6$ is isothiazol-3-yl-methyl, $R^5$ is hydrogen, and the combination of $R^{2a}$, $R^{2b}$ and $R^{2c}$ for a compound corresponds in each case to one row of Table A Table 208
Compounds of the formula Ia.1 in which $R^6$ is isothiazol-4-yl-methyl, $R^5$ is hydrogen, and the combination of $R^{2a}$, $R^{2b}$ and $R^{2c}$ for a compound corresponds in each case to one row of Table A Table 209
Compounds of the formula Ia.1 in which $R^6$ is isothiazol-5-yl-methyl, $R^5$ is hydrogen, and the combination of $R^{2a}$, $R^{2b}$ and $R^{2c}$ for a compound corresponds in each case to one row of Table A Table 210
Compounds of the formula Ia.1 in which $R^6$ is oxazol-2-yl-methyl, $R^5$ is hydrogen, and the combination of $R^{2a}$, $R^{2b}$ and $R^{2c}$ for a compound corresponds in each case to one row of Table A Table 211
Compounds of the formula Ia.1 in which $R^6$ is oxazol-4-yl-methyl, $R^5$ is hydrogen, and the combination of $R^{2a}$, $R^{2b}$ and $R^{2c}$ for a compound corresponds in each case to one row of Table A Table 212
Compounds of the formula Ia.1 in which $R^6$ is oxazol-5-yl-methyl, $R^5$ is hydrogen, and the combination of $R^{2a}$, $R^{2b}$ and $R^{2c}$ for a compound corresponds in each case to one row of Table A Table 213
Compounds of the formula Ia.1 in which $R^6$ is isoxazol-3-yl-methyl, $R^5$ is hydrogen, and the combination of $R^{2a}$, $R^{2b}$ and $R^{2c}$ for a compound corresponds in each case to one row of Table A Table 214
Compounds of the formula Ia.1 in which $R^6$ is isoxazol-4-yl-methyl, $R^5$ is hydrogen, and the combination of $R^{2a}$, $R^{2b}$ and $R^{2c}$ for a compound corresponds in each case to one row of Table A Table 215
Compounds of the formula Ia.1 in which $R^6$ is isoxazol-5-yl-methyl, $R^5$ is hydrogen, and the combination of $R^{2a}$, $R^{2b}$ and $R^{2c}$ for a compound corresponds in each case to one row of Table A Table 216
Compounds of the formula Ia.1 in which $R^6$ is 1,2,3-1H-triazol-4-yl-methyl, $R^5$ is hydrogen, and the combination of $R^{2a}$, $R^{2b}$ and $R^{2c}$ for a compound corresponds in each case to one row of Table A Table 217
Compounds of the formula Ia.1 in which $R^6$ is 1-methyl-1,2,3-triazol-4-yl-methyl, $R^5$ is hydrogen, and the combination of $R^{2a}$, $R^{2b}$ and $R^{2c}$ for a compound corresponds in each case to one row of Table A Table 218
Compounds of the formula Ia.1 in which $R^6$ is 1,2,4-1H-triazol-3-yl-methyl, $R^5$ is hydrogen, and the combination of $R^{2a}$, $R^{2b}$ and $R^{2c}$ for a compound corresponds in each case to one row of Table A Table 219
Compounds of the formula Ia.1 in which $R^6$ is 1-methyl-1,2,4-triazol-3-yl-methyl, $R^5$ is hydrogen, and the combination of $R^{2a}$, $R^{2b}$ and $R^{2c}$ for a compound corresponds in each case to one row of Table A Table 220
Compounds of the formula Ia.1 in which $R^6$ is 4-methyl-1,2,4-triazol-3-yl-methyl, $R^5$ is hydrogen, and the combination of $R^{2a}$, $R^{2b}$ and $R^{2c}$ for a compound corresponds in each case to one row of Table A Table 221
Compounds of the formula Ia.1 in which $R^6$ is 1,2,4-oxadiazol-3-yl-methyl, $R^5$ is hydrogen, and the combination of $R^{2a}$, $R^{2b}$ and $R^{2c}$ for a compound corresponds in each case to one row of Table A Table 222
Compounds of the formula Ia.1 in which $R^6$ is 1,3,4-thiadiazol-2-yl-methyl, $R^5$ is hydrogen, and the combination of $R^{2a}$, $R^{2b}$ and $R^{2c}$ for a compound corresponds in each case to one row of Table A Table 223
Compounds of the formula Ia.1 in which $R^6$ is 1,2,3,4-1H-tetrazol-5-yl-methyl, $R^5$ is hydrogen, and the combination of $R^{2a}$, $R^{2b}$ and $R^{2c}$ for a compound corresponds in each case to one row of Table A Table 224
Compounds of the formula Ia.1 in which $R^6$ is 1-methyl-1,2,3,4-tetrazol-5-yl-methyl, $R^5$ is hydrogen, and the combination of $R^{2a}$, $R^{2b}$ and $R^{2c}$ for a compound corresponds in each case to one row of Table A Table 225
Compounds of the formula Ia.1 in which $R^6$ is 1,2,3,4-2H-tetrazol-5-yl-methyl, $R^5$ is hydrogen, and the combination of $R^{2a}$, $R^{2b}$ and $R^{2c}$ for a compound corresponds in each case to one row of Table A Table 226
Compounds of the formula Ia.1 in which $R^6$ is 2-methyl-1,2,3,4-tetrazol-5-yl-methyl, $R^5$ is hydrogen, and the combination of $R^{2a}$, $R^{2b}$ and $R^{2c}$ for a compound corresponds in each case to one row of Table A Table 227
Compounds of the formula Ia.1 in which $R^6$ is tetrahydrofuran-2-yl-methyl, $R^5$ is hydrogen, and the combination of $R^{2a}$, $R^{2b}$ and $R^{2c}$ for a compound corresponds in each case to one row of Table A Table 228
Compounds of the formula Ia.1 in which $R^6$ is tetrahydrofuran-3-yl-methyl, $R^5$ is hydrogen, and the combination of $R^{2a}$, $R^{2b}$ and $R^{2c}$ for a compound corresponds in each case to one row of Table A Table 229
Compounds of the formula Ia.1 in which $R^6$ is 1,3-dioxolan-2-yl-methyl, $R^5$ is hydrogen, and the combination of $R^{2a}$, $R^{2b}$ and $R^{2c}$ for a compound corresponds in each case to one row of Table A Table 230
Compounds of the formula Ia.1 in which $R^6$ is 2-(1,3-dioxolan-2-yl)-ethyl, $R^5$ is hydrogen, and the combination of $R^{2a}$, $R^{2b}$ and $R^{2c}$ for a compound corresponds in each case to one row of Table A Table 231
Compounds of the formula Ia.1 in which $R^6$ is 2-pyridyl-eth-1-yl, $R^5$ is hydrogen, and the combination of $R^{2a}$, $R^{2b}$ and $R^{2c}$ for a compound corresponds in each case to one row of Table A Table 232
Compounds of the formula Ia.1 in which $R^6$ is (1R)-2-pyridyl-eth-1-yl, $R^5$ is hydrogen, and the combination of $R^{2a}$, $R^{2b}$ and $R^{2c}$ for a compound corresponds in each case to one row of Table A Table 233
Compounds of the formula Ia.1 in which $R^6$ is (1S)-2-pyridyl-eth-1-yl, $R^5$ is hydrogen, and the combination of $R^{2a}$, $R^{2b}$ and $R^{2c}$ for a compound corresponds in each case to one row of Table A Table 234
Compounds of the formula Ia.1 in which $R^6$ is 1,3-dioxan-2-yl-methyl, $R^5$ is hydrogen, and the combination of $R^{2a}$, $R^{2b}$ and $R^{2c}$ for a compound corresponds in each case to one row of Table A Table 235
Compounds of the formula Ia.1 in which $R^6$ is —$CONH_2$, $R^5$ is hydrogen, and the combination of $R^{2a}$, $R^{2b}$ and $R^{2c}$ for a compound corresponds in each case to one row of Table A Table 236
Compounds of the formula Ia.1 in which $R^6$ is —CONH—$CH_3$, $R^5$ is hydrogen, and the combination of $R^{2a}$, $R^{2b}$ and $R^{2c}$ for a compound corresponds in each case to one row of Table A Table 237
Compounds of the formula Ia.1 in which $R^6$ is —CONH—$CH_2CH_3$, $R^5$ is hydrogen, and the combination of $R^{2a}$, $R^{2b}$ and $R^{2c}$ for a compound corresponds in each case to one row of Table A Table 238
Compounds of the formula Ia.1 in which $R^6$ is —CONH-cyclopropyl, $R^5$ is hydrogen, and the combination of $R^{2a}$, $R^{2b}$ and $R^{2c}$ for a compound corresponds in each case to one row of Table A Table 239
Compounds of the formula Ia.1 in which $R^6$ is —NHCO—NH—$CH_3$, $R^5$ is hydrogen, and the combination of $R^{2a}$, $R^{2b}$ and $R^{2c}$ for a compound corresponds in each case to one row of Table A Table 240
Compounds of the formula Ia.1 in which $R^6$ is —NHCO—NH—$CH_2CH_3$, $R^5$ is hydrogen, and the combination of $R^{2a}$, $R^{2b}$ and $R^{2c}$ for a compound corresponds in each case to one row of Table A Table 241
Compounds of the formula Ia.1 in which $R^6$ is —NHCO—NH—$CH_2CH_2CH_3$, $R^5$ is hydrogen, and the combination of $R^{2a}$, $R^{2b}$ and $R^{2c}$ for a compound corresponds in each case to one row of Table A Table 242
Compounds of the formula Ia.1 in which $R^6$ is —NHCO—NH—$CH(CH_3)_2$, $R^5$ is hydrogen, and the combination of $R^{2a}$, $R^{2b}$ and $R^{2c}$ for a compound corresponds in each case to one row of Table A Table 243
Compounds of the formula Ia.1 in which $R^6$ is —NHCO—NH—$CH_2CF_3$, $R^5$ is hydrogen, and the combination of $R^{2a}$, $R^{2b}$ and $R^{2c}$ for a compound corresponds in each case to one row of Table A Table 244
Compounds of the formula Ia.1 in which $R^6$ is —NHCO—NH—$CH_2CHF_2$, $R^5$ is hydrogen, and the combination of $R^{2a}$, $R^{2b}$ and $R^{2c}$ for a compound corresponds in each case to one row of Table A Table 245
Compounds of the formula Ia.1 in which $R^6$ is —NHCO—NH—$CH(CH_3)CF_3$, $R^5$ is hydrogen, and the combination of $R^{2a}$, $R^{2b}$ and $R^{2c}$ for a compound corresponds in each case to one row of Table A Table 246
Compounds of the formula Ia.1 in which $R^6$ is —NHCO—NH—$CH(CF_3)_2$, $R^5$ is hydrogen, and the combination of $R^{2a}$, $R^{2b}$ and $R^{2c}$ for a compound corresponds in each case to one row of Table A Table 247
Compounds of the formula Ia.1 in which $R^6$ is —NHCO—NH—$CH_2CN$, $R^5$ is hydrogen, and the combination of $R^{2a}$, $R^{2b}$ and $R^{2c}$ for a compound corresponds in each case to one row of Table A Table 248
Compounds of the formula Ia.1 in which $R^6$ is —NHCO—NH—$CH_2$—CH=$CH_2$, $R^5$ is hydrogen, and the combination of $R^{2a}$, $R^{2b}$ and $R^{2c}$ for a compound corresponds in each case to one row of Table A Table 249
Compounds of the formula Ia.1 in which $R^6$ is —NHCO—NH—$CH_2$—CH≡CH, $R^5$ is hydrogen, and the combination of $R^{2a}$, $R^{2b}$ and $R^{2c}$ for a compound corresponds in each case to one row of Table A Table 250
Compounds of the formula Ia.1 in which $R^6$ is —NHCO—NH-cyclopropyl, $R^5$ is hydrogen, and the combination of $R^{2a}$, $R^{2b}$ and $R^{2c}$ for a compound corresponds in each case to one row of Table A Table 251
Compounds of the formula Ia.1 in which $R^6$ is —NHCO—NH-(1-cyanocyclopropyl), $R^5$ is hydrogen, and the combination of $R^{2a}$, $R^{2b}$ and $R^{2c}$ for a compound corresponds in each case to one row of Table A Table 252
Compounds of the formula Ia.1 in which $R^6$ is —NHCO—NH-cyclobutyl, $R^5$ is hydrogen, and the combination of $R^{2a}$, $R^{2b}$ and $R^{2c}$ for a compound corresponds in each case to one row of Table A Table 253
Compounds of the formula Ia.1 in which $R^6$ is —NHCO—NH-(1-cyanocyclobutyl), $R^5$ is hydrogen, and the combination of $R^{2a}$, $R^{2b}$ and $R^{2c}$ for a compound corresponds in each case to one row of Table A Table 254
Compounds of the formula Ia.1 in which $R^6$ is —NHCO—NH—$CH_2$-cyclopropyl, $R^5$ is hydrogen, and the combination of $R^{2a}$, $R^{2b}$ and $R^{2c}$ for a compound corresponds in each case to one row of Table A Table 255
Compounds of the formula Ia.1 in which $R^6$ is —NHCO—NH—$CH_2$-(1-cyanocyclopropyl), $R^5$ is hydrogen, and the combination of $R^{2a}$, $R^{2b}$ and $R^{2c}$ for a compound corresponds in each case to one row of Table A Table 256
Compounds of the formula Ia.1 in which $R^6$ is —CH=$NOCH_3$, $R^5$ is hydrogen, and the combination of $R^{2a}$, $R^{2b}$ and $R^{2c}$ for a compound corresponds in each case to one row of Table A Table 257
Compounds of the formula Ia.1 in which $R^6$ is —CH=$NOCH_2CH_3$, $R^5$ is hydrogen, and the combination of $R^{2a}$, $R^{2b}$ and $R^{2c}$ for a compound corresponds in each case to one row of Table A Table 258
Compounds of the formula Ia.1 in which $R^6$ is —CH=$NOCH_2CF_3$, $R^5$ is hydrogen, and the combination of $R^{2a}$, $R^{2b}$ and $R^{2c}$ for a compound corresponds in each case to one row of Table A Table 259
Compounds of the formula Ia.1 in which $R^6$ is —CH=$NOCH_2CH$=$CH_2$, $R^5$ is hydrogen, and the combination of $R^{2a}$, $R^{2b}$ and $R^{2c}$ for a compound corresponds in each case to one row of Table A Table 260
Compounds of the formula Ia.1 in which $R^6$ is —CH=$NOCH_2C$≡CH, $R^5$ is hydrogen, and the combination of $R^{2a}$, $R^{2b}$ and $R^{2c}$ for a compound corresponds in each case to one row of Table A Tables 261 to 520
Compounds of the formula Ia.1 in which $R^6$ is as defined in tables 1 to 260, $R^5$ is methyl, and the combination of $R^{2a}$, $R^{2b}$ and $R^{2c}$ for a compound corresponds in each case to one row of Table A Tables 521 to 780

Compounds of the formula Ia.1 in which $R^6$ is as defined in tables 1 to 260, $R^5$ is ethyl, and the combination of $R^{2a}$, $R^{2b}$ and $R^{2c}$ for a compound corresponds in each case to one row of Table A Tables 781 to 1040

Compounds of the formula Ia.1 in which $R^6$ is as defined in tables 1 to 260, $R^5$ is allyl, and the combination of $R^{2a}$, $R^{2b}$ and $R^{2c}$ for a compound corresponds in each case to one row of Table A Tables 1041 to 1300

Compounds of the formula Ia.1 in which $R^6$ is as defined in tables 1 to 260, $R^5$ is propargyl, and the combination of $R^{2a}$, $R^{2b}$ and $R^{2c}$ for a compound corresponds in each case to one row of Table A Tables 1301 to 1560

Compounds of the formula Ia.1 in which $R^6$ is as defined in tables 1 to 260, $R^5$ is —$CH_2$—CN, and the combination of $R^{2a}$, $R^{2b}$ and $R^{2c}$ for a compound corresponds in each case to one row of Table A Tables 1561 to 1820

Compounds of the formula Ia.1 in which $R^6$ is as defined in tables 1 to 260, $R^5$ is —$CH_2$—$OCH_3$, and the combination of $R^{2a}$, $R^{2b}$ and $R^{2c}$ for a compound corresponds in each case to one row of Table A Table 1821

Compounds of the formula Ia.1 in which $R^5$ and $R^6$ form together =$S(CH_2CH_3)_2$ and the combination of $R^{2a}$, $R^{2b}$ and $R^{2c}$ for a compound corresponds in each case to one row of Table A Table 1822

Compounds of the formula Ia.1 in which $R^5$, $R^6$ and the nitrogen atom to which they are bound form together 3-ethyl-4-oxo-imidazolidin-1-yl and the combination of $R^{2a}$, $R^{2b}$ and $R^{2c}$ for a compound corresponds in each case to one row of Table A Table 1823

Compounds of the formula Ia.1 in which $R^5$, $R^6$ and the nitrogen atom to which they are bound form together 4-oxo-3-(2,2,2-trifluoroethyl)-imidazolidin-1-yl and the combination of $R^{2a}$, $R^{2b}$ and $R^{2c}$ for a compound corresponds in each case to one row of Table A Tables 1824 to 3646

Compounds of the formula Ia.2 in $R^5$ and $R^6$ are as defined in tables 1 to 1823, and the combination of $R^{2a}$, $R^{2b}$ and $R^{2c}$ for a compound corresponds in each case to one row of Table A Tables 3647 to 5469

Compounds of the formula Ia.3 in $R^5$ and $R^6$ are as defined in tables 1 to 1823, and the combination of $R^{2a}$, $R^{2b}$ and $R^{2c}$ for a compound corresponds in each case to one row of Table A Tables 5470 to 7292

Compounds of the formula Ia.4 in $R^5$ and $R^6$ are as defined in tables 1 to 1823, and the combination of $R^{2a}$, $R^{2b}$ and $R^{2c}$ for a compound corresponds in each case to one row of Table A

TABLE A

| No. | $R^{2a}$ | $R^{2b}$ | $R^{2c}$ |
|---|---|---|---|
| A-1 | F | H | F |
| A-2 | F | F | F |
| A-3 | F | Cl | F |
| A-4 | F | Br | F |
| A-5 | F | H | Cl |
| A-6 | F | H | Br |
| A-7 | Cl | H | Cl |
| A-8 | Cl | Cl | Cl |
| A-9 | Cl | F | Cl |
| A-10 | Cl | Br | Cl |
| A-11 | Cl | H | Br |
| A-12 | Br | H | Br |
| A-13 | Br | F | Br |
| A-14 | Br | Cl | Br |
| A-15 | $CF_3$ | H | F |
| A-16 | $CF_3$ | H | Cl |
| A-17 | $CF_3$ | H | Br |
| A-18 | $CF_3$ | H | $CF_3$ |
| A-19 | $CF_3$ | F | F |
| A-20 | $CF_3$ | Cl | Cl |
| A-21 | $CF_3$ | Br | Br |
| A-22 | $OCF_3$ | H | F |
| A-23 | $OCF_3$ | H | Cl |
| A-24 | $OCF_3$ | H | Br |
| A-25 | $OCF_3$ | H | $CF_3$ |
| A-26 | $OCF_3$ | H | H |
| A-27 | $CF_3$ | H | H |
| A-28 | Br | H | H |
| A-29 | Cl | H | H |
| A-30 | F | H | H |
| A-31 | Cl | F | H |

Among the above compounds, preference is given to compounds Ia.1 and Ia.3.

In a specific embodiment, the compounds I are selected from the compounds specified in the examples, either as a free base or in form of an agriculturally or veterinarily acceptable salt, an N-oxide or a stereoisomer thereof.

The compounds of the formula (I) can be prepared by the methods as described in the below schemes or and in the synthesis descriptions of the working examples, or by standard methods of organic chemistry. The substituents, variables and indices are as defined above for formula (I), if not otherwise specified.

Compounds of formula I wherein $X^1$ is O and wherein $R^{3b}$ is hydrogen (termed below as compounds I.a) can be prepared by reacting a compound of formula 1 as shown in scheme 1 below in an imination/Michael addition reaction with hydroxylamine. A' is A or a precursor of A. Typical precursors of A are a halogen atom, CN, carboxy, $C(O)OR^{z1}$ (carboxy and $C(O)OR^{z1}$ are of course only "precursors" if in the desired compound I W is S and/or $R^{z1}$ is not the desired radical $R^9$ and/or if Y is to be —$NR^5R^6$) or —$OSO_2$—$R^{z1}$, where $R^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy. Compounds I' correspond to compounds I when A' is A. Compounds I.a' correspond to compounds I.a when A' is A. Suitable reaction conditions are described, for example, in WO 2012/158396. Suitably, hydroxylamine is used as the hydrochloride salt. The reaction is generally carried out in the presence of a base, such as NaOH, KOH, $Na_2CO_3$ and the like. Suitable solvents are aqueous, such as water or mixtures of water with polar solvents, such as tetrahydrofuran, dioxane and lower alkanols. If necessary (i.e. if A' is a precursor of A), A' is then converted into a group A.

Scheme 1

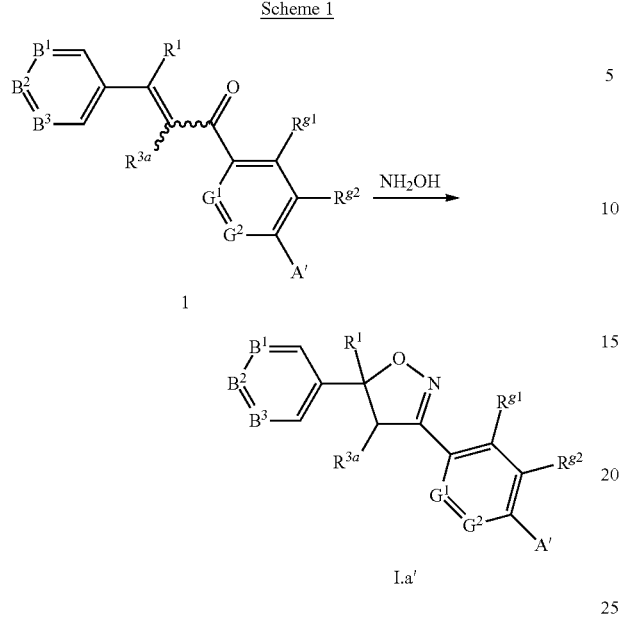

Compounds of formula I wherein $X^1$ is $CH_2$ and wherein $R^{3b}$ is hydrogen (termed below as compounds I.b) can be prepared by first subjecting a compound of formula 1 to a Michael addition with nitromethane to 2, then reducing the nitro group of 2 to an amino group. The resulting aminoketone reacts spontaneously to the pyrroline I.b', as shown in scheme 2 below. Compounds I.b' correspond to compounds I.b when A' is A. Suitable reaction conditions are described, for example, in US 2010/0298558. The Michael addition of nitromethane to 1 is carried out in the presence of a base. Suitable bases are for example alkali hydroxides and alcoholates, but preferably non-nucleophilic bases, such as DBN or DBU, are used. Suitable solvents depend i.a. on the base used. If an alkali hydroxide is used, suitably an aqueous medium, such as water of mixtures thereof with lower alkanols are used, while alkoxides are used in the respective alcohol. If non-nucleophilic bases are used, polar, non-protic solvents, such as acetonitrile, tetrahydrofuran, dioxane and the like are preferred. If necessary (i.e. if A' is a precursor of A), A' is then converted into a group A. Reduction of 2 is carried out with a suitable reduction agent, such as Zn, Sn, Sn(II) salts, Fe or hydrogen-producing agents, such as ammonium formate in the presence of Zn or Pd.

Scheme 2

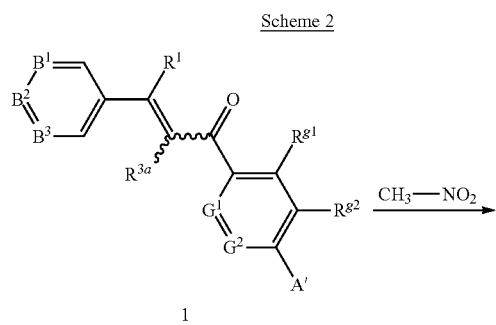

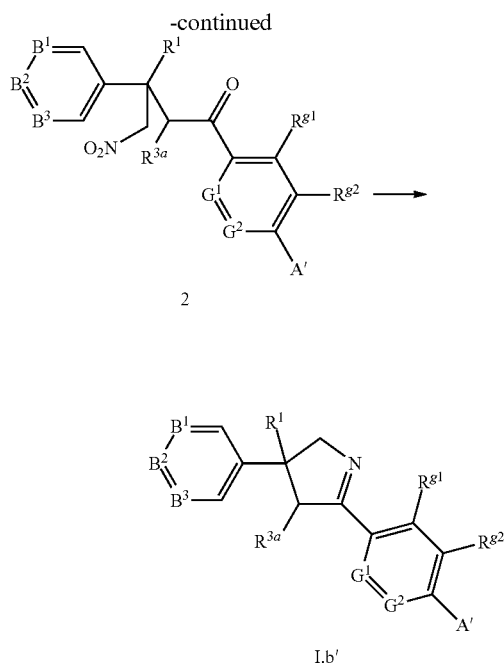

Compound 1 can be prepared in analogy to the method described in EP-A-2172462 and as shown in scheme 3 below by subjecting the ketones 3 and 4 to an aldol condensation.

Scheme 3

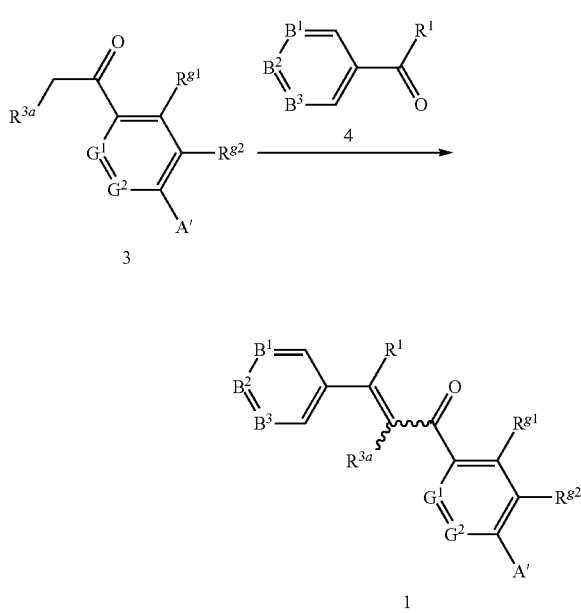

Ketone 3 can be obtained in analogy to the method described in US 2011/0152246. Compounds I wherein W is O can be prepared by reacting a compound I' wherein A' is Cl, Br, I or triflate with carbon monoxide in the presence of a palladium catalyst and an alcohol ROH, wherein R is $C_1$-$C_4$-alkyl, to a compound of formula 5. Suitable palladium catalysts are for example those described in WO 2011/161130.

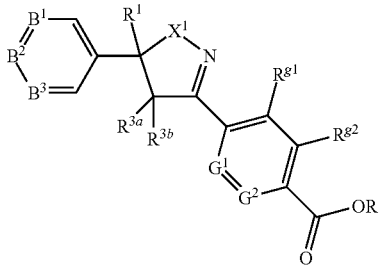

If desired, this ester is then hydrolyzed to the respective carboxylic acid, which is then reacted under standard amidation conditions with an amine $NHR^5R^6$. Hydrolyzation can be carried out under standard conditions, e.g. under acidic conditions using for example hydrochloric acid, sulfuric acid or trifluoroacetic acid, or under basic conditions using for example an alkali metal hydroxide, such as LiOH, NaOH or KOH. Amidation is preferably carried out by activation of the carboxylic acids with oxalylchloride [(COCl)$_2$] or thionylchloride (SOCl$_2$) to the respective acid chlorides, followed by reaction with an amine $NHR^5R^6$. Alternatively, amidation is carried out in the presence of a coupling reagent. Suitable coupling reagent (activators) are well known and are for instance selected from carbodiimides, such as DCC (dicyclohexylcarbodiimide) and DCI (diisopropylcarbodiimide), benzotriazol derivatives, such as HATU (O-(7-azabenzotriazol-1-yl)-N, N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino) methylene]-5-chloro tetrafluoroborate) and phosphonium-derived activators, such as BOP ((benzotriazol-1-yloxy)-tris (dimethyl-amino)phosphonium hexafluorophosphate), Py-BOP ((benzotriazol-1-yloxy)-tripyrrolidinphosphonium hexafluorophosphate) and Py-BrOP (bromotripyrroli-dinphosphonium hexafluorophosphate). Generally, the activator is used in excess. The benzotriazol and phosphonium coupling reagents are generally used in a basic medium.

Compounds I wherein W is S, can be prepared by reacting the corresponding oxo-compound (W is O) with Lawesson's reagent (CAS 19172-47-5), see for example Jesberger et al., Synthesis, 2003, 1929-1958 and references therein. Solvents such as HMPA or THF at an elevated temperature such as 60° C. to 100° C. can be used. Preferred reaction conditions are THF at 65° C.

Compounds I wherein Y is OH can be prepared from compounds I wherein Y is hydrogen via oxidation of this aldehyde group A. Suitable conditions are for example those of the Pinnick or Lindgren oxidation using a chlorite, such as sodium chlorite NaClO$_2$ as oxidation agent. As scavenger for the hypochlorite (HOCl) formed in the reaction, 2-methyl-2-butene or hydrogen peroxide can be used. The Pinnick or Lindgren oxidation is generally carried out in a water-containing solvent under slightly acidic, buffered conditions (pH ca. 3-5; use of a hydrogen phosphate, e.g. NaH$_2$PO$_4$). Other suitable oxidation conditions are described, for example, in WO 2011/022337. The resulting carboxylic acid can then be further esterified to give compounds I wherein Y is OR$^9$ wherein R$^9$ is not hydrogen, or subjected to an amidation as described above to afford compounds I wherein Y is $NR^5R^6$.

Compounds I wherein R$^{3b}$ is not hydrogen can be prepared from compounds I.a' or I.b' in analogy to the methods described in WO 2010/020521 by reacting these with a base, such as lithium diisopropylamine, followed by the addition of an electrophile, e.g. a halogenating agent, such as 4-iodotoluene difluoride, N-fluorobenzenesulfonimide ("NFSI"), N-chlorosuccinimide ("NCS"), N-bromosuccinimide ("NBS") or N-iodosuccinimide ("NIS"), an alkylating agent, such as an alkyl halide, e.g. methyl iodide, a sulfanylating agent, such as methanesulfenyl chloride (CH$_3$S—Cl), S-methyl methanethiosulfonate (CH$_3$SO$_2$—SCH$_3$) or dimethyldisulfide (CH$_3$S—SCH$_3$), or, for introducing OH, a hydroxylating agent, such as oxaziridines (for instance, N-sulfonyl oxaziridines) or oxodiperoxymolybdenum(pyridine)-(hexamethyl-phosphoric triamide) ("MoOPH").

As a rule, the compounds of formula I including their stereoisomers, salts, and N-oxides, and their precursors in the synthesis process, can be prepared by the methods described above. If individual compounds can not be prepared via the above-described routes, they can be prepared by derivatization of other compounds I or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:

insects from the order of the lepidopterans (*Lepidoptera*), for example *Acronicta major, Adoxophyes orana, Aedia leucomelas, Agrotis* spp. such as *Agrotis fucosa, Agrotis segetum, Agrotis ipsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis, Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xylostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura; Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis*, beetles (*Coleoptera*), for example *Acanthoscehdes obtectus, Adoretus* spp., *Agelastica alni, Agrilus sinuatus, Agriotes* spp. such as *Agriotes fuscicollis, Agriotes lineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria linearis; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus* spp. such as *Ceuthorrhynchus assimilis, Ceuthorrhynchus napi; Chaetocnema tibialis, Cleonus mendicus, Conoderus* spp. such as *Conoderus vespertinus; Cosmopolites* spp., *Costelytra zealandica, Crioceris asparagi, Cryptorhynchus lapathi, Ctenicera* ssp. such as *Ctenicera destructor; Curculio* spp., *Dectes texanus, Dermestes* spp., *Diabrotica* spp. such as *Diabrotica 12-punctata Diabrotica speciosa, Diabrotica longicornis, Diabrotica semipunctata, Diabrotica virgifera; Epilachna* spp. such as *Epilachna varivestis, Epilachna vigintioctomaculata; Epitrix* spp. such as *Epitrix hirtipennis; Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga* spp., *Phyllotreta* spp. such as *Phyllotreta chrysocephala, Phyllotreta nemorum, Phyllotreta striolata; Phyllophaga* spp., *Phyllopertha horticola, Popillia japonica, Premnotrypes* spp., *Psylliodes chrysocephala, Ptinus* spp., *Rhizobius ventralis, Rhizopertha dominica, Sitona lineatus, Sitophilus* spp. such as *Sitophilus granaria, Sitophilus zeamais; Sphenophorus* spp. such as *Sphenophorus levis; Sternechus* spp. such as *Sternechus subsignatus; Symphyletes* spp., *Tenebrio molitor, Tribolium* spp. such as *Tribolium castaneum; Trogoderma* spp., *Tychius* spp., *Xylotrechus* spp., and *Zabrus* spp. such as *Zabrus* tenebrioides, flies, mosquitoes (*Diptera*), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gam-* biae, *Anopheles leucosphyrus*, *Anopheles maculipennis*, *Anopheles minimus*, *Anopheles quadrimaculatus*, *Anopheles sinensis*; *Bibio hortulanus*, *Calliphora erythrocephala*, *Calliphora vicina*, *Cerafitis capitata*, *Ceratitis capitata*, *Chrysomyia* spp. such as *Chrysomya bezziana*, *Chrysomya hominivorax*, *Chrysomya macellaria*; *Chrysops atlanticus*, *Chrysops discalis*, *Chrysops silacea*, *Cochliomyia* spp. such as *Cochliomyia hominivorax*; *Contarinia* spp. such as *Contarinia sorghicola*; *Cordylobia anthropophaga*, *Culex* spp. such as *Culex nigripalpus*, *Culex pipiens*, *Culex quinquefasciatus*, *Culex tarsalis*, *Culex tritaeniorhynchus*; *Culicoides furens*, *Culiseta inornata*, *Culiseta melanura*, *Cuterebra* spp., *Dacus cucurbitae*, *Dacus oleae*, *Dasineura brassicae*, *Delia* spp. such as *Delia antique*, *Delia coarctata*, *Delia platura*, *Delia radicum*; *Dermatobia hominis*, *Drosophila* spp., *Fannia* spp. such as *Fannia canicularis*; *Gastraphilus* spp. such as *Gasterophilus intestinalis*; *Geomyza Tripunctata*, *Glossina fuscipes*, *Glossina morsitans*, *Glossina palpalis*, *Glossina tachinoides*, *Haematobia irritans*, *Haplodiplosis equestris*, *Hippelates* spp., *Hylemyia* spp. such as *Hylemyia platura*; *Hypoderma* spp. such as *Hypoderma lineata*; *Hyppobosca* spp., *Leptoconops torrens*, *Liriomyza* spp. such as *Liriomyza sativae*, *Liriomyza trifolii*; *Lucilia* spp. such as *Lucilia caprina*, *Lucilia cuprina*, *Lucilia sericata*; *Lycoria pectoralis*, *Mansonia titillanus*, *Mayetiola* spp. such as *Mayetiola destructor*; *Musca* spp. such as *Musca autumnalis*, *Musca domestica*; *Muscina stabulans*, *Oestrus* spp. such as *Oestrus ovis*; *Opomyza florum*, *Oscinella* spp. such as *Oscinella frit*; *Pegomya hysocyami*, *Phlebotomus argentipes*, *Phorbia* spp. such as *Phorbia antiqua*, *Phorbia brassicae*, *Phorbia coarctata*; *Prosimulium mixtum*, *Psila rosae*, *Psorophora columbiae*, *Psorophora discolor*, *Rhagoletis cerasi*, *Rhagoletis pomonella*, *Sarcophaga* spp. such as *Sarcophaga haemorrhoidalis*; *Simulium vittatum*, *Stomoxys* spp. such as *Stomoxys calcitrans*; *Tabanus* spp. such as *Tabanus atratus*, *Tabanus bovinus*, *Tabanus lineola*, *Tabanus similis*; *Tannia* spp., *Tipula oleracea*, *Tipula paludosa*, and *Wohlfahrtia* spp., thrips (*Thysanoptera*), e.g. *Baliothrips biformis*, *Dichromothrips corbetti*, *Dichromothrips ssp.*, *Enneothrips flavens*, *Frankliniella* spp. such as *Frankliniella fusca*, *Frankliniella occidentalis*, *Frankliniella tritici*; *Heliothrips* spp., *Hercinothrips femoralis*, *Kakothrips* spp., *Rhipiphorothrips cruentatus*, *Scirtothrips* spp. such as *Scirtothrips citri*; *Taeniothrips cardamoni*, *Thrips* spp. such as *Thrips oryzae*, *Thrips palmi*, *Thrips tabaci*; termites (*Isoptera*), e.g. *Calotermes flavicollis*, *Coptotermes formosanus*, *Heterotermes aureus*, *Heterotermes longiceps*, *Heterotermes tenuis*, *Leucotermes flavipes*, *Odontotermes* spp., *Reticulitermes* spp. such as *Reticulitermes speratus*, *Reticulitermes flavipes*, *Reticulitermes grassei*, *Reticulitermes lucifugus*, *Reticulitermes santonensis*, *Reticulitermes virginicus*; *Termes natalensis*, cockroaches (*Blattaria-Blattodea*), e.g. *Acheta domesticus*, *Blatta orientalis*, *Blattella asahinae*, *Blattella germanica*, *Gryllotalpa* spp., *Leucophaea maderae*, *Locusta* spp., *Melanoplus* spp., *Periplaneta americana*, *Periplaneta australasiae*, *Periplaneta brunnea*, *Periplaneta fuligginosa*, *Periplaneta japonica*, bugs, aphids, leafhoppers, whiteflies, scale insects, cicadas (*Hemiptera*), e.g. *Acrosternum* spp. such as *Acrosternum hilare*; *Acyrthosipon* spp. such as *Acyrthosiphon onobrychis*, *Acyrthosiphon pisum*; *Adelges laricis*, *Aeneolamia* spp., *Agonoscena* spp., *Aleurodes* spp., *Aleurolobus barodensis*, *Aleurothrixus* spp., *Amrasca* spp., *Anasa tristis*, *Antestiopsis* spp., *Anuraphis cardui*, *Aonidiella* spp., *Aphanostigma piri*, *Aphidula nasturtii*, *Aphis* spp. such as *Aphis fabae*, *Aphis forbesi*, *Aphis gossypii*, *Aphis grossulariae*, *Aphis pomi*, *Aphis sambuci*, *Aphis schneideri*, *Aphis spiraecola*; *Arboridia apicalis*, *Arilus critatus*, *Aspidiella* spp., *Aspidiotus* spp., *Atanus* spp., *Aulacorthum solani*, *Bemisia* spp. such as *Bemisia argentifolii*, *Bemisia tabaci*; *Blissus* spp. such as *Blissus leucopterus*; *Brachycaudus cardui*, *Brachycaudus helichrysi*, *Brachycaudus persicae*, *Brachycaudus prunicola*, *Brachycolus* spp., *Brevicoryne brassicae*, *Calligypona marginata*, *Calocoris* spp., *Campylomma livida*, *Capitophorus horni*, *Carneocephala fulgida*, *Cavelerius* spp., *Ceraplastes* spp., *Ceratovacuna lanigera*, *Cercopidae*, *Cerosipha gossypii*, *Chaetosiphon fragaefolii*, *Chionaspis tegalensis*, *Chlorita onukii*, *Chromaphis juglandicola*, *Chrysomphalus ficus*, *Cicadulina mbila*, *Cimex* spp. such as *Cimex hemipterus*, *Cimex lectularius*; *Coccomytilus halli*, *Coccus* spp., *Creontiades dilutus*, *Cryptomyzus ribis*, *Cryptomyzus ribis*, *Cyrtopeltis notatus*, *Dalbulus* spp., *Dasynus piperis*, *Dialeurades* spp., *Diaphorina* spp., *Diaspis* spp., *Dichelops furcatus*, *Diconocoris hewetti*, *Doralis* spp., *Dreyfusia nordmannianae*, *Dreyfusia piceae*, *Drosicha* spp., *Dysaphis* spp. such as *Dysaphis plantaginea*, *Dysaphis pyri*, *Dysaphis radicola*; *Dysaulacorthum pseudosolani*, *Dysdercus* spp. such as *Dysdercus cingulatus*, *Dysdercus intermedius*; *Dysmicoccus* spp., *Empoasca* spp. such as *Empoasca fabae*, *Empoasca solana*; *Eriosoma* spp., *Erythroneura* spp., *Eurygaster* spp. such as *Eurygaster integriceps*; *Euscelis bilobatus*, *Euschistus* spp. such as *Euschistuos heros*, *Euschistus impictiventris*, *Euschistus servus*; *Geococcus coffeae*, *Halyomorpha* spp. such as *Halyomorpha halys*; *Heliopeltis* spp., *Homalodisca coagulata*, *Horcias nobilellus*, *Hyalopterus pruni*, *Hyperomyzus lactucae*, *Icerya* spp., *Idiocerus* spp., *Idioscopus* spp., *Laodelphax striatellus*, *Lecanium* spp., *Lepidosaphes* spp., *Leptocorisa* spp., *Leptoglossus phyllopus*, *Lipaphis erysimi*, *Lygus* spp. such as *Lygus hesperus*, *Lygus lineolaris*, *Lygus pratensis*; *Macropes excavatus*, *Macrosiphum* spp. such as *Macrosiphum rosae*, *Macrosiphum avenae*, *Macrosiphum euphorbiae*; *Mahanarva fimbriolata*, *Megacopta cribraria*, *Megoura viciae*, *Melanaphis pyrarius*, *Melanaphis sacchari*, *Metcafiella* spp., *Metopolophium dirhodum*, *Miridae* spp., *Monellia costalis*, *Monelliopsis pecanis*, *Myzus* spp. such as *Myzus ascalonicus*, *Myzus cerasi*, *Myzus persicae*, *Myzus varians*; *Nasonovia ribis-nigri*, *Nephotettix* spp. such as *Nephotettix malayanus*, *Nephotettix nigropictus*, *Nephotettix parvus*, *Nephotettix virescens*; *Nezara* spp. such as *Nezara viridula*; *Nilaparvata lugens*, *Oebalus* spp., *Oncometopia* spp., *Orthezia praelonga*, *Parabemisia myricae*, *Paratrioza* spp., *Parlatoria* spp., *Pemphigus* spp. such as *Pemphigus bursarius*; *Pentomidae*, *Peregrinus maidis*, *Perkinsiella saccharicida*, *Phenacoccus* spp., *Phloeomyzus passerinii*, *Phorodon humuli*, *Phylloxera* spp., *Piesma quadrata*, *Piezodorus* spp. such as *Piezodorus guildinii*, *Pinnaspis aspidistrae*, *Planococcus* spp., *Protopulvinaria pyriformis*, *Psallus seriatus*, *Pseudacysta persea*, *Pseudaulacaspis pentagona*, *Pseudococcus* spp. such as *Pseudococcus comstocki*; *Psylla* spp. such as *Psylla mali*, *Psylla piri*; *Pteromalus* spp., *Pyrilla* spp., *Quadraspidiotus* spp., *Quesada gigas*, *Rastrococcus* spp., *Reduvius senilis*, *Rhodnius* spp., *Rhopalomyzus ascalonicus*, *Rhopalosiphum* spp. such as *Rhopalosiphum pseudobrassicas*, *Rhopalosiphum insertum*, *Rhopalosiphum maidis*, *Rhopalosiphum padi*; *Sagatodes* spp., *Sahlbergella singularis*, *Saissetia* spp., *Sappaphis mala*, *Sappaphis mali*, *Scaphoides titanus*, *Schizaphis graminum*, *Schizoneura lanuginosa*, *Scotinophora* spp., *Selenaspidus articulatus*, *Sitobion avenae*, *Sogata* spp., *Sogatella furcifera*, *Solubea insularis*, *Stephanitis nashi*, *Stictocephala festina*, *Tenalaphara malayensis*, *Thyanta* spp. such as *Thyanta perditor*; *Tibraca* spp., *Tinocallis caryaefoliae*,

*Tomaspis* spp., *Toxoptera* spp. such as *Toxoptera aurantii; Trialeurodes* spp. such as *Trialeurodes vaporariorum; Triatoma* spp., *Trioza* spp., *Typhlocyba* spp., *Unaspis* spp. such as *Unaspis yanonensis*; and *Viteus vitifolii*, ants, bees, wasps, sawflies (*Hymenoptera*), e.g. *Athalia rosae, Atta capiguara, Atta cephalotes, Atta cephalotes, Atta laevigata, Atta robusta, Atta sexdens, Atta texana, Bombus* spp., *Camponotus floridanus, Crematogaster* spp., *Dasymutilla occidentalis, Diprion* spp., *Dolichovespula maculata, Hoplocampa* spp. such as *Hoplocampa minuta, Hoplocampa testudinea; Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richteri, Solenopsis xyloni, Vespa* spp. such as *Vespa crabro*, and *Vespula squamosa*, crickets, grasshoppers, locusts (*Orthoptera*), e.g. *Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus*, and *Zonozerus variegatus*, arachnids (*Arachnida*), such as acari, e.g. of the families Argasidae, Ixodidae and Sarcoptidae, such as *Amblyomma* spp. (e.g. *Amblyomma americanum, Amblyomma variegatum, Amblyomma maculatum*), *Argas* spp. (e.g. *Argas persicus*), *Boophilus* spp. (e.g. *Boophilus annulatus, Boophilus decoloratus, Boophilus microplus*), *Dermacentor silvarum, Dermacentor andersoni, Dermacentor variabilis, Hyalomma* spp. (e.g. *Hyalomma truncatum*), *Ixodes* spp. (e.g. *Ixodes ricinus, Ixodes rubicundus, Ixodes scapularis, Ixodes holocyclus, Ixodes pacificus*), *Ornithodorus* spp. (e.g. *Ornithodorus moubata, Ornithodorus hermsi, Ornithodorus turicata*), *Ornithonyssus bacoti, Otobius megnini, Dermanyssus gallinae, Psoroptes* spp. (e.g. *Psoroptes ovis*), *Rhipicephalus* spp. (e.g. *Rhipicephalus sanguineus, Rhipicephalus appendiculatus, Rhipicephalus evertsi*), *Rhizoglyphus* spp., *Sarcoptes* spp. (e.g. *Sarcoptes scabiei*), and *Eriophyidae* spp. such as *Acaria sheldoni, Aculops* spp. (e.g. *Aculops pelekassi*) *Aculus* spp. (*e.g. Aculus schlechtendali*), *Epitrimerus pyri, Phyllocoptruta oleivora* and *Eriophyes* spp. (e.g. *Eriophyes sheldoni*); *Tarsonemidae* spp. such as *Hemitarsonemus* spp., *Phytonemus pallidus* and *Polyphagotarsonemus latus, Stenotarsonemus* spp.; *Tenuipalpidae* spp. such as *Brevipalpus* spp. (e.g. *Brevipalpus phoenicis*); *Tetranychidae* spp. such as *Eotetranychus* spp., *Eutetranychus* spp., *Oligonychus* spp., *Tetranychus cinnabarinus, Tetranychus kanzawai, Tetranychus pacificus, Tetranychus telarius* and *Tetranychus urticae; Bryobia praetiosa, Panonychus* spp. (e.g. *Panonychus ulmi, Panonychus citri*), *Metatetranychus* spp. and *Oligonychus* spp. (e.g. *Oligonychus pratensis*), *Vasates lycopersici; Araneida*, e.g. *Latrodectus mactans*, and *Loxosceles reclusa. And Acarus siro, Chorioptes* spp., *Scorpio maurus* fleas (*Siphonaptera*), e.g. *Ceratophyllus* spp., *Ctenocephalides felis, Ctenocephalides canis, Xenopsylla cheopis, Pulex irritans, Tunga penetrans*, and *Nosopsyllus fasciatus*, silverfish, firebrat (*Thysanura*), e.g. *Lepisma saccharina* and *Thermobia domestica*, centipedes (*Chilopoda*), e.g. *Geophilus* spp., *Scutigera* spp. such as *Scutigera coleoptrata;* millipedes (*Diplopoda*), e.g. *Blaniulus guttulatus, Narceus* spp.,

Earwigs (*Dermaptera*), e.g. *forficula auricularia*, lice (*Phthiraptera*), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., springtails (*Collembola*), e.g. *Onychiurus* ssp. such as *Onychiurus armatus*, They are also suitable for controlling nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus* Mamiya et Kiyohara, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semipenetrans*; Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, Arion spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides*

*stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata;*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. *such as Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis ssp, Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. *such as Orseolia oryzae; Oxycaraenus hyalinipennis, Plusia* spp., *Pomacea canaliculata, Procornitermes ssp, Procornitermes triacifer, Psylloides* spp., *Rachiplusia* spp., *Rhodopholus* spp., *Scaptocoris castanea, Scaptocoris* spp., *Scirpophaga* spp. *such as Scirpophaga incertulas, Scirpophaga innotata; Scotinophara* spp. *such as Scotinophara coarctata; Sesamia* spp. *such as Sesamia inferens, Sogaella frucifera, Solenapsis geminata, Spissistilus* spp., *Stalk borer, Stenchaetothrips biformis, Steneotarsonemus spinki, Sylepta derogata, Telehin licus, Trichostrongylus* spp.

The compounds of the present invention, including their salts, stereoisomers and tautomers, are particularly useful for controlling insects, preferably sucking or piercing and chewing and biting insects such as insects from the genera *Lepidoptera, Coleoptera* and *Hemiptera*, in particular *Lepidoptera, Coleoptera* and true bugs.

The compounds of the present invention, including their salts, stereoisomers and tautomers, are moreover useful for controlling insects of the orders *Thysanoptera, Diptera* (especially flies, mosquitoes), *Hymenoptera* (especially ants) and *Isoptera* (especially termites).

The compounds of the present invention, including their salts, stereoisomers and tautomers, are particularly useful for controlling insects of the orders *Lepidoptera* and *Coleoptera*.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines.

Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e. g. components comprising compounds I and/or active substances from the groups M.1 to M.UN.X or F.I to F.XIII, can be applied jointly (e.g. after tank mix) or consecutively.

The following list M of pesticides, grouped according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;

M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;

M.28.5k) 5-bromo-N-[2,4-dichloro-6-(methylcarbamoyl)phenyl]-2-(3,5-dichloro-2-pyridyl)pyrazole-3-carboxamide;

M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from M.28.6 N2-(1-cyano-1-methyl-ethyl)-N1-(2,4-dimethylphenyl)-3-iodo-phthalamide; or M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.UN.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound M.UN.X.3: 11-(4-chloro-2,6-dimethylphenyl)-12-hydroxy-1,4-dioxa-9-azadispiro[4.2.4.2]-tetradec-11-en-10-one, or the compound M.UN.X.4: 3-(4'-fluoro-2,4-dimethylbiphenyl-3-yl)-4-hydroxy-8-oxa-1-azaspiro[4.5]dec-3-en-2-one, or the compound M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, I-1582); or M.UN.X.6; a compound selected from the group of
M.UN.X.6a) (E/Z)—N-[1-[(6-chloro-3-pyridyl)methyl]-2-pyridylidene]-2,2,2-trifluoro-acetamide;
M.UN.X.6b) (E/Z)—N-[1-[(6-chloro-5-fluoro-3-pyridyl)methyl]-2-pyridylidene]-2,2,2-trifluoro-acetamide;
M.UN.X.6c) (E/Z)-2,2,2-trifluoro-N-[1-[(6-fluoro-3-pyridyl)methyl]-2-pyridylidene]acetamide;
M.UN.X.6d) (E/Z)—N-[1-[(6-bromo-3-pyridyl)methyl]-2-pyridylidene]-2,2,2-trifluoro-acetamide;
M.UN.X.6e) (E/Z)—N-[1-[1-(6-chloro-3-pyridyl)ethyl]-2-pyridylidene]-2,2,2-trifluoro-acetamide;
M.UN.X.6f) (E/Z)—N-[1-[(6-chloro-3-pyridyl)methyl]-2-pyridylidene]-2,2-difluoro-acetamide;
M.UN.X.6g) (E/Z)-2-chloro-N-[1-[(6-chloro-3-pyridyl)methyl]-2-pyridylidene]-2,2-difluoro-acetamide;
M.UN.X.6h) (E/Z)—N-[1-[(2-chloropyrimidin-5-yl)methyl]-2-pyridylidene]-2,2,2-trifluoro-acetamide and
M.UN.X.6i) (E/Z)—N-[1-[(6-chloro-3-pyridyl)methyl]-2-pyridylidene]-2,2,3,3,3-pentafluoro-propanamide); or of the compounds M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or M.UN.X.8: 1-[(2-chlorothiazol-5-yl)methyl]-3-(3,5-dichlorophenyl)-9-methyl-4-oxo-pyrido[1,2-a]pyrimidin-1-ium-2-olate; or M.UN.X.9: 8-chloro-N-[2-chloro-5-methoxyphenyl)sulfonyl]-6-trifluoromethyl)-imidazo[1,2-a]pyridine-2-carboxamide; or M.UN.X.10: 4-[5-(3,5-dichlorophenyl)-5-(trifluoromethyl)-4H-isoxazol-3-yl]-2-methyl-N-(1-oxothietan-3-yl)benzamide; or M.UN.X.11: 5-[3-[2,6-dichloro-4-(3,3-dichloroallyloxy)phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compounds have been described likewise M.UN.X.1 in WO2005/085216, M.UN.X2. in WO2009/002809 and in WO2011/149749 and the isoxazoline M.UN.X.10 in WO2013/050317. The pyripyropene derivative afidopyropen has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenyl-sulfide like M.UN.X.5 have been described in WO2006/043635 and biological control agents on basis of *bacillus firmus* in WO2009/124707. The neonicotinoids 4A.1 is known from WO20120/069266 and WO2011/06946, the M.4.A.2 from WO2013/003977, the M4.A.3. from WO2010/069266.

The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i) is described in WO2011/085575, the M.28.5j) in WO2008/134969, the M.28.5k) in US2011/046186 and the M.28.5l) in WO2012/034403. The diamide compounds M.28.6 and M.28.7 can be found in CN102613183.

The compounds M.UN.X.6a) to M.UN.X.6i) listed in M.UN.X.6 have been described in WO2012/029672. The mesoionic antagonist compound M.UN.X.7 was described in WO2012/092115, the mesoionic antagonist compound M.UN.X.8 was described in WO 2013/192035, the nematicide M.UN.X.9 in WO2013/055584 and the pyridalyl-type analogue M.UN.X.11 in WO2010/060379.

Preferred additional pesticidally active ingredients are those selected from the IRAC group 1, the Acetylcholinesterase (AChE) inhibitors, herein from the group 1A (Carbamtes) Thiodicarb, Methomyl and Carbaryl, and from the group 1B(Organophosphates), especially Acephate, Chlorpyriphos and Dimethoate, from the group 2B, the fiproles, here especially ethiprole and fipronil, from the group 3, the pyrethroids, here especially lambda-cyhalothrin, alpha-cypermethrin or deltametrin, and from the group 4A, the neonicotinoids, here especially acetamiprid, clothianidin, dinotefuran, imidacloprid, nitenpyram, thiacloprid or thiomethoxam.

Especially combinations of compounds of the invention with fiproles, neonictinoids or pyrethroids may possibly exhibit synergistic control of stinkbugs (according to the Colby formula), in particular *Euschistus*, e.g. *Euschistus heros*.

The following list F of active substances, in conjunction with which the compounds according to the invention can be used, is intended to illustrate the possible combinations but does not limit them:

F.) Respiration Inhibitors
- F.I 1) Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobine, metominostrobin, orysastrobin, picoxystrobin, pyraclostrobin, pyrametostrobin, pyraoxystrobin, trifloxystrobin and 2-(2-(3-(2,6-dichloro-phenyl)-1-methyl-allylideneaminooxymethyl)-phenyl)-2-methoxyimino-N-methyl-acetamide, pyribencarb, triclopyricarb/chlorodincarb, famoxadone, fenamidone;
- F.I 2) inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(hydroxy-4-methoxy-2-pyridinyl)carbonyl]amino]-6-methyl-4,9-dioxo-8-(phenylmethyl)-1,5-dioxonan-7-yl 2-methylpropanoate;
- F.I 3) inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide, N-[2-(2,4-difluorophenyl)phenyl]-3-(trifluoromethyl)pyrazine-2-carboxamide;
- F.I 4) other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

F.II) Sterol Biosynthesis Inhibitors (SBI Fungicides)
- F.II 1) $C_{14}$ demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thio-cyanato-1H-[1,2,4]triazole, 2-[rel-(2 S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;
- F.II 2) Delta14-reductase inhibitors: aldimorph, dodemorph, dodemorph-acetate, fenpropimorph, tridemorph, fenpropidin, piperalin, spiroxamine;
- F.II 3) Inhibitors of 3-keto reductase: fenhexamid;

F.III) Nucleic Acid Synthesis Inhibitors
- F.III 1) phenylamides or acyl amino acid fungicides: benalaxyl, benalaxyl-M, kiralaxyl, metalaxyl, metalaxyl-M (mefenoxam), ofurace, oxadixyl;
- F.III 2) others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

F.IV) Inhibitors of Cell Division and Cytoskeleton
- F.IV 1) tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluoro-phenyl)-[1,2,4]triazolo[1,5-a]pyrimidine;
- F.IV 2) other cell division inhibitors: diethofencarb, ethaboxam, pencycuron, fluopicolide, zoxamide, metrafenone, pyriofenone;

F.V) Inhibitors of Amino Acid and Protein Synthesis
- F.V 1) methionine synthesis inhibitors (anilino-pyrimidines): cyprodinil, mepanipyrim, pyrimethanil;
- F.V 2) protein synthesis inhibitors: blasticidin-S, kasugamycin, kasugamycin hydrochloride-hydrate, mildiomycin, streptomycin, oxytetracyclin, polyoxine, validamycin A;

F.VI) Signal Transduction Inhibitors
- F.VI 1) MAP/histidine kinase inhibitors: fluoroimid, iprodione, procymidone, vinclozolin, fenpiclonil, fludioxonil;
- F.VI 2) G protein inhibitors: quinoxyfen;

F.VII) Lipid and Membrane Synthesis Inhibitors
- F.VII 1) Phospholipid biosynthesis inhibitors: edifenphos, iprobenfos, pyrazophos, isoprothiolane;
- F.VII 2) lipid peroxidation: dicloran, quintozene, tecnazene, tolclofos-methyl, biphenyl, chloroneb, etridiazole;
- F.VII 3) phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
- F.VII 4) compounds affecting cell membrane permeability and fatty acides: propamocarb, propamocarb-hydrochlorid;
- F.VII 5) fatty acid amide hydrolase inhibitors: oxathiapiprolin;

F.VIII) Inhibitors with Multi Site Action
- F.VIII 1) inorganic active substances: Bordeaux mixture, copper acetate, copper hydroxide, copper oxychloride, basic copper sulfate, sulfur;
- F.VIII 2) thio- and dithiocarbamates: ferbam, mancozeb, maneb, metam, metiram, propineb, thiram, zineb, ziram;
- F.VIII 3) organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;
- F.VIII 4) guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

F.IX) Cell Wall Synthesis Inhibitors
- F.IX 1) inhibitors of glucan synthesis: validamycin, polyoxin B;
- F.IX 2) melanin synthesis inhibitors: pyroquilon, tricyclazole, carpropamid, dicyclomet, fenoxanil;

F.X) Plant Defence Inducers
- F.X 1) acibenzolar-S-methyl, probenazole, isotianil, tiadinil, prohexadione-calcium;
- F.X 2) phosphonates: fosetyl, fosetyl-aluminum, phosphorous acid and its salts, 4-cyclopropyl-N-(2,4-dimethoxyphenyl)thiadiazole-5-carboxamide;

F.XI) Unknown Mode of Action
bronopol, chinomethionat, cyflufenamid, cymoxanil, dazomet, debacarb, diclo-mezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propyl-chromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2, 5-dimethyl-phenyl)-N-ethyl-N-methyl formamidine, N'-(4-(4-fluoro-3-trifluoromethyl-phenoxy)-2, 5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

F.XII) Biopesticides
- F.XII 1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonec-*

*tria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum; T. stromaticum, T. virens* (also named *Gliocladium virens*), *T. viride, Typhula phacorrhiza, Ulocladium oudemansii, Verticillium dahlia*, zucchini yellow mosaic virus (avirulent strain);

F.XII 2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;

The fungicidal active compounds mentioned above of groups F.I to F.XI, their preparation and their action against harmful fungi are generally known (cf., for example, http://www.hclrss.demon.co.uk/index.html).

The fungicides of chemical nature described by common names, their preparation and their activity against pests are known (cf.: http://www.alanwood.net/pesticides/); these pesticides are often commercially available.

The fungicides described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 11/77514; WO13/047749, WO 10/069882, WO 13/047441, WO 03/16303, WO 09/90181, WO 13/007767, WO 13/010862, WO 13/024009 and WO 13/024010).

The biopesticides from group F.XII) of fungicides, their preparation and their pesticidal activity e.g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group F.XII. may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group F.XII may also have fungicidal, bactericidal, viricidal, plant defense activator, insecticidal, acaricidal, molluscidal, pheromone and/or nematicidal activity.

Many of these biopesticides are registered and/or are commercially available: aluminium silicate (Screen™ Duo from Certis LLC, USA), *Agrobacterium radio-bacter* K1026 (e.g. NoGall® from Becker Underwood Pty Ltd., Australia), *A. radiobacter* K84 (Nature 280, 697-699, 1979; e.g. Gall-Troll® from AG Biochem, Inc., C, USA), *Ampelomyces quisqualis* M-10 (e.g. AQ 10® from Intrachem Bio GmbH & Co. KG, Germany), Ascophyllum nodosum (Norwegian kelp, Brown kelp) extract or filtrate (e.g. ORKA GOLD from Becker Underwood, South Africa; or Goemar® from Laboratoires Goemar, France), *Aspergillus flavus* NRRL 21882 isolated from a peanut in Georgia in 1991 by the USDA, National Peanut Research Laboratory (e.g. in Afla-Guard® from Syngenta, CH), mixtures of *Aureobasidium pullulans* DSM14940 and DSM 14941 (e.g. blastospores in Blossom-Protect® from bio-ferm GmbH, Germany), Azospirillum brasilense XOH (e.g. AZOS from Xtreme Gardening, USA or RTI Reforestation Technologies International; USA), *Bacillus amyloliquefaciens* FZB42 (e.g. in RhizoVital® 42 from AbiTEP GmbH, Berlin, Germany), *B. amyloliquefaciens* IN937a (J. Microbiol. Biotechnol. 17(2), 280-286, 2007; e.g. in BioYield® from Gustafson LLC, TX, USA), *B. amyloliquefaciens* IT-45 (CNCM 1-3800) (e.g. Rhizocell C from ITHEC, France), *B. amyloliquefaciens* subsp. *plantarum* MBI600 (NRRL B-50595, deposited at United States Department of Agriculture) (e.g. Integral®, Subtilex® NG from Becker Underwood, USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *B. pumilus* GB34 (ATCC 700814; e.g. in YieldShield® from Gustafson LLC, TX, USA), and *Bacillus pumilus* KFP9F (NRRL B-50754) (e.g. in BAC-UP or FUSION-P from Becker Underwood South Africa), *B. pumilus* QST 2808 (NRRL B-30087) (e.g. Sonata® and Ballad® Plus from AgraQuest Inc., USA), *B. subtilis* GB03 (e.g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B-21661 in Rhapsody®, Serenade® MAX and Serenade® ASO from AgraQuest Inc., USA), *B. subtilis* var. *amylolique-faciens* FZB24 (e.g. Taegro® from Novozyme Biologicals, Inc., USA), *B. subtilis* var. *amyloliquefaciens* D747 (e.g. Double Nickel 55 from Certis LLC, USA), *B. thuringiensis* ssp. *aizawai* ABTS-1857 (e.g. in XenTari® from BioFa AG, Münsingen, Germany), B. t. ssp. *aizawai* SAN 401 I, ABG-6305 and ABG-6346, *Bacillus* t. ssp. *israelensis* AM65-52 (e.g. in VectoBac® from Valent Biosciences, IL, USA), *Bacillus thuringiensis* ssp. *kurstaki* SB4 (NRRL B-50753; e.g. Beta Pro® from Becker Underwood, South Africa), B. t. ssp. *kurstaki* ABTS-351 identical to HD-1 (ATCC SD-1275; e.g. in Dipel® DF from Valent BioSciences, IL, USA), B. t. ssp. *kurstaki* EG 2348 (e.g. in Lepinox® or Rapax® from CBC (Europe) S.r.l., Italy), B. t. ssp. *tenebrionis* DSM 2803 (EP 0 585 215 B1; identical to NRRL B-15939; Mycogen Corp.), B. t. ssp. *tenebrionis* NB-125 (DSM 5526; EP 0 585 215 B1; also referred to as SAN 418 I or ABG-6479; former production strain of Novo-Nordisk), B. t. ssp. *tenebrionis* NB-176 (or NB-176-1) a gamma-irradiated, induced high-yielding mutant of strain NB-125 (DSM 5480; EP 585 215 B1; Novodor® from Valent BioSciences, Switzerland), *Beauveria bassiana* ATCC 74040 (e.g. in Naturalis® from CBC (Europe) S.r.l., Italy), *B. bassiana* DSM 12256 (US 200020031495; e.g. BioExpert® SC from Live Systems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e.g. BroadBand® from Becker Underwood, South Africa), *B. brongniartii* (e.g. in Melocont® from Agrifutur, Agrianello, Italy, for control of cockchafer; J. Appl. Microbiol. 100(5), 1063-72, 2006), *Bradyrhizobium* sp. (e.g. Vault® from Becker Underwood, USA), *B. japonicum* (e.g. VAULT® from Becker Underwood, USA), *Candida oleophila* 1-182 (NRRL Y-18846; e.g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e.g. Biocure® (in mixture with lysozyme) and BioCoat® from Micro Flo Company, USA (BASF SE) and Arysta), Chitosan (e.g. Armour-Zen® from BotriZen Ltd., NZ), *Clonostachys rosea* f. *catenulata*, also named *Gliocladium catenulatum* (e.g. isolate J 1446: Prestop® from Verdera Oy, Finland), Chromobacterium subtsugae PRAA4-1 isolated from soil under an eastern hemlock (*Tsuga canadensis*) in the Catoctin Mountain region of central Maryland (e.g. in GRANDEVO from Marrone Bio Innovations, USA), *Coniothyrium minitans* CON/M/91-08 (e.g. Contans® WG from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Cryptophlebia leucotreta* granulovirus (CrleGV) (e.g. in CRYPTEX from Adermatt Biocontrol, Switzerland), *Cydia pomonella* granulovirus (CpGV) V03 (DSM GV-0006; e.g. in MADEX Max from Andermatt Biocontrol, Switzerland), CpGV V22 (DSM GV-0014; e.g. in MADEX Twin from Adermatt Biocontrol, Switzerland), *Delftia acidovorans* RAY209 (ATCC PTA-4249; WO 2003/57861; e.g. in BIOBOOST from Brett Young, Winnipeg, Canada), *Dilophosphora alopecuri* (Twist Fungus from Becker Underwood, Australia), *Ecklonia maxima* (kelp) extract (e.g. KELPAK SL from Kelp Products Ltd, South Africa), formononetin (e.g. in MYCONATE from Plant Health Care plc, U.K.), *Fusarium oxysporum* (e.g. BIO-FOX® from S.I.A.P.A., Italy, FUSACLEAN® from Natural Plant Protection, France), *Glomus intraradices* (e.g. MYC 4000 from ITHEC, France), *Glomus intraradices* RTI-801 (e.g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e.g. MESSENGER or HARP-N-Tek from Plant Health Care plc, U.K.; Science 257, 1-132, 1992), Heterorhabditis bacteriophaga (e.g. Nemasys® G from Becker Underwood Ltd., UK), Isaria fumosorosea Apopka-97 (ATCC 20874) (PFR-97™ from Certis LLC, USA), cis-jasmone (U.S. Pat. No. 8,221,736), laminarin (e.g. in VACCIPLANT from Laboratoires Goemar, St. Malo, France or Stähler SA, Switzerland), *Lecanicillium longisporum* KV42 and KV71 (e.g. VERTALEC® from Koppert BV, Netherlands), *L. muscarium* KV01 (formerly *Verticillium lecanii*) (e.g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in Niger; also NRRL 50758) (e.g. GREEN MUSCLE® from Becker Underwood, South Africa), M. a. var. *acridum* FI-985 (e.g. GREEN GUARD® SC from Becker Underwood Pty Ltd, Australia), *M. anisopliae* FI-1045 (e.g. BIOCANE® from Becker Underwood Pty Ltd, Australia), *M. anisopliae* $F_{52}$ (DSM 3884, ATCC 90448; e.g. MET52® Novozymes Biologicals BioAg Group, Canada), *M. anisopliae* ICIPE 69 (e.g. METATHRIPOL from ICIPE, Nairobe, Kenya), *Metschnikowia fructicola* (NRRL Y-30752; e.g. SHEMER® from Agrogreen, Israel, now distributed by Bayer CropSciences, Germany; U.S. Pat. No. 6,994,849), *Microdochium dimerum* (e.g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e.g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e.g. NO FLY™ from Natural Industries, Inc., USA), *P. lilacinus* 251 (e.g. in BioAct®/MeloCon® from Prophyta, Germany; Crop Protection 27, 352-361, 2008; originally isolated from infected nematode eggs in the Philippines), *P. lilacinus* DSM 15169 (e.g. NEMATA® SC from Live Systems Technology S.A., Colombia), *P. lilacinus* BCP2 (NRRL 50756; e.g. PL GOLD from Becker Underwood BioAg SA Ltd, South Africa), mixture of *Paenibacillus alvei* NAS6G6 (NRRL B-50755), *Pantoea vagans* (formerly *agglomerans*) $C_9$-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* spp. ATCC PTA-9643 (WO 2010/085795), *Pasteuria* spp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e.g. Jump Start® from Novozymes Biologicals BioAg Group, Canada, originally isolated from soil in southern Alberta; Fertilizer Res. 39, 97-103, 1994), *Phlebiopsis gigantea* (e.g. RotStop® from Verdera Oy, Finland), *Pichia anomala* WRL-076 (NRRL Y-30842; U.S. Pat. No. 8,206,972), potassium bicarbonate (e.g. Amicarb® from Stähler SA, Switzerland), potassium silicate (e.g. Sil-MATRIX™ from Certis LLC, USA), *Pseudozyma flocculosa* PF-A22 UL (e.g. Sporodex® from Plant Products Co. Ltd., Canada), *Pseudomonas* sp. DSM 13134 (WO 2001/40441, e.g. in PRORADIX from Sourcon Padena GmbH & Co. KG, Hechinger Str. 262, 72072 Tübingen, Germany), *P. chloraphis* MA 342 (e.g. in CERALL or CEDEMON from BioAgri AB, Uppsala, Sweden), *P. fluorescens* CL 145A (e.g. in ZEQUANOX from Marrone BioInnovations, Davis, Calif., USA; J. Invertebr. Pathol. 113(1):104-14, 2013), *Pythium oligandrum* DV 74 (ATCC 38472; e.g. POLYVERSUM® from Remeslo SSRO, Biopreparaty, Czech Rep. and GOWAN, USA; US 2013/0035230), *Reynoutria sachlinensis* extract (e.g. REGALIA® SC from Marrone BioInnovations, Davis, Calif., USA), *Rhizobium leguminosarum* bv. *phaseolii* (e.g. RHIZO-STICK from Becker Underwood, USA), R. l. *trifolii* RP113-7 (e.g. DORMAL from Becker Underwood, USA; Appl. Environ. Microbiol. 44(5), 1096-1101), R. l. bv. *viciae* P1NP3Cst (also referred to as 1435; New Phytol 179(1), 224-235, 2008; e.g. in NODULATOR PL Peat Granule from Becker Underwood, USA; or in NODULATOR XL PL from Becker Underwood, Canada), R. l. bv. *viciae* SU303 (e.g. NODULAID Group E from Becker Underwood, Australia), R. I. bv. *viciae* WSM1455 (e.g. NODULAID Group F from Becker Underwood, Australia), *R. tropici* SEMIA 4080 (identical to PRF 81; Soil Biology & Biochemistry 39, 867-876, 2007), *Sinorhizobium meliloti* MSDJ0848 (INRA, France) also referred to as strain 2011 or RCR$^{2011}$ (Mol Gen Genomics (2004) 272: 1-17; e.g. DORMAL ALFALFA from Becker Underwood, USA; NITRAGIN® Gold from Novozymes Biologicals BioAg Group, Canada), *Sphaerodes mycoparasitica* IDAC 301008-01 (WO 2011/022809), *Steinernema carpocapsae* (e.g. MILLENIUM® from Becker Underwood Ltd., UK), *S. feltiae* (NEM-ASHIELD® from BioWorks, Inc., USA; NEMASYS® from Becker Underwood Ltd., UK), *S. kraussei* L137 (NEMA-SYS® L from Becker Underwood Ltd., UK), *Streptomyces griseoviridis* K61 (e.g. MYCOSTOP® from Verdera Oy, Espoo, Finland; Crop Protection 25, 468-475, 2006), *S. lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968,503), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. asperellum* ICC 012 (e.g. in TENET WP, REMDIER WP, BIOTEN WP from Isagro NC, USA, BIO-TAM from AgraQuest, USA), *T. atroviride* LC$_{52}$ (e.g. SENTINEL® from Agrimm Technologies Ltd, NZ), *T. atroviride* CNCM 1-1237 (e.g. in Esquive WG from Agrauxine S.A., France, e.g. against pruning wound diseases on vine and plant root pathogens), *T. fertile* JM41R (NRRL 50759; e.g. RICHPLUS™ from Becker Underwood Bio Ag SA Ltd, South Africa), *T. gamsii* ICC 080 (e.g. in TENET WP, REMDIER WP, BIOTEN WP from Isagro NC, USA, BIO-TAM from AgraQuest, USA), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (also named *Gliocladium virens*) (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy) and *Ulocladium oudemansii* HRU3 (e.g. in BOTRY-ZEN® from Botry-Zen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-lnstitut DSMZ-Deutsche Sammlung von Mikroorganismen und Zellkulturen GmbH, Inhoffenstraβe 7 B, 38124 Braunschweig, Germany (strains with prefix DSM); International Depositary Authority of Canada Collection, Canada (strains with prefix IDAC); International Collection of Micro-orgniasms from Plants, Landcare Research, Private Bag 92170, Auckland Mail Centre, Auckland 1142, New Zealand (strans with prefix ICMP); IITA, PMB 5320, Ibadan, Nigeria (strains with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuãria, Rua Gonçalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Room 19-9, Beltsville, Md. 20705, USA (strains with prefix USDA: Beltsville *Rhizobium* Culture Collection Catalog March 1987 USDA-ARS ARS-30: http://pdf.usaid.gov/pdf_docs/PNAAW891.pdf); and Murdoch University, Perth, Western Australia (strains with prefix WSM). Further strains may be found at the Global catalogue of Microorganisms: http://gcm.wfcc.info/ and http://www.landcareresearch.co.nz/resources/collections/icmp and further references to strain collections and their prefixes at http://refs.wdcm.org/collections.htm. *Bacillus amyloliquefaciens* subsp. *plantarum* MB1600 (NRRL B-50595) is deposited under accession number NRRL B-50595 with the strain designation *Bacillus subtilis* 1430 (and identical to NCIMB 1237). Recently, MBI 600 has been re-classified as *Bacillus amyloliquefaciens* subsp. *plantarum* based on polyphasic testing which combines classical microbiological methods relying on a mixture of tradditional tools (such as culture-based methods) and molecular tools (such as genotyping and fatty acids analysis). Thus, *Bacillus subtilis* MBI600 (or MBI 600 or MBI-600) is identical to *Bacillus amyloliquefaciens* subsp. *plantarum* MB1600, formerly *Bacillus subtilis* MB1600. *Bacillus amyloliquefaciens* MBI600 is known as plant growth-promoting rice seed treatment from Int. J. Microbiol. Res. 3(2) (2011), 120-130 and further described e.g. in US 2012/0149571 A1. This strain MB1600 is e.g. commercially available as liquid formulation product INTEGRAL® (Becker-Underwood Inc., USA). *Bacillus subtilis* strain FB17 was originally isolated from red beet roots in North America (System Appl. Microbiol 27 (2004) 372-379). This *B. subtilis* strain promotes plant health (US 2010/0260735 A1; WO 2011/109395 A2). *B. subtilis* FB17 has also been deposited at ATCC under number PTA-11857 on Apr. 26, 2011. *Bacillus subtilis* strain FB17 may be referred elsewhere to as UD1022 or UD10-22. *Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. japonicum* SEMIA 5079 (e.g. Gelfix 5 or Adhere 60 from Nitral Urbana Laboratories, Brazil, a BASF Company), *B. japonicum* SEMIA 5080 (e.g. GELFIX 5 or ADHERE 60 from Nitral Urbana Laboratories, Brazil, a BASF Company), *B. mojavensis* AP-209 (NRRL B-50616), *B. solisalsi* AP-217 (NRRL B-50617), *B. pumilus* strain INR-7 (otherwise referred to as BU-F22 (NRRL B-50153) and BU-F33 (NRRL B-50185)), *B. simplex* ABU 288 (NRRL B-50340)

and *B. amyloliquefaciens* subsp. *plantarum* MBI600 (NRRL B-50595) have been mentioned i.a. in US patent appl. 20120149571, U.S. Pat. No. 8,445,255, WO 2012/079073. *Bradyrhizobium japonicum* USDA 3 is known from U.S. Pat. No. 7,262,151.

Jasmonic acid or salts (jasmonates) or derivatives include without limitation potassium jasmonate, sodium jasmonate, lithium jasmonate, ammonium jasmonate, dimethyl-ammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl-pentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitoes, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics. The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art. For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing Bacillus thuringiensis toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by tradditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants. Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides the use of a compound of the present invention, including its stereoisomers, veterinarily acceptable salts or N-oxides, for treating or protecting an animal from infestation or infection by invertebrate pests.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development. The compounds of the present invention are especially useful for combating parasites of the following orders and species, respectively:

fleas (*Siphonaptera*), e.g. *Ctenocephalides felis, Ctenocephalides canis, Xenopsylla cheopis, Pulex irritans, Tunga penetrans*, and *Nosopsyllus fasciatus,* cockroaches (*Blattaria-Blattodea*), e.g. *Blattella germanica, Blattella asahinae, Periplaneta americana, Periplaneta japonica, Periplaneta brunnea, Periplaneta fuliginosa, Periplaneta australasiae*, and *Blatta orientalis,* flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucos-*

*phyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (*Phthiraptera*), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (*Parasitiformes*): ticks (*Ixodida*), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp., Bugs (*Heteropterida*): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi, Camallanida*, e.g. *Dracunculus medinensis* (guinea worm)

Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp., Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp., Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them. The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

The compounds of the invention are better bio-degradable than those of the prior art and in addition retain a high level of pest control. This makes them superior in terms of environmental safety. In light of the structural similarities of the compounds of formula I, this significant difference in bio-degradability in favour of the compounds of the invention is unexpected and cannot be derived from what is known from the prior art.

EXAMPLES

The present invention is now illustrated in further details by the following examples, without imposing any limitation thereto.

I. Preparation Examples

Compounds can be characterized e.g. by coupled High Performance Liquid Chromatography/mass spectrometry (HPLC/MS), by $^1$H-NMR and/or by their melting points.
Analytical HPLC Column:

Method A: Analytical UPLC column: Phenomenex Kinetex 1.7 μm XB-C18 100A; 50×2.1 mm from Phenomenex, Germany. Elution: acetonitrile+0.1% trifluoroacetic acid (TFA)/water+0.1% trifluoroacetic acid (TFA) in a ratio from 5:95 to 100:0 in 1.5 min at 60° C. Flow: 0.8 mL/min to 1 mL/min in 1.5 min. MS-method: ESI positive.

$^1$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: d for day(s), h for hour(s), min for minute(s), r.t./room temperature for 20-25° C., THF for tetrahydrofuran, DCE for dichloroethane, PyBroP for bromotripyrrolidinophosphonium hexafluorophosphate.

C.1 Compound Examples 1

Compound examples 1-1 to 1-138 correspond to compounds of formula C.1:

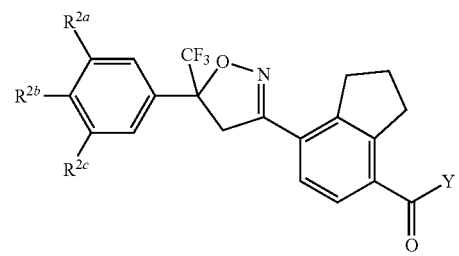

C.1 wherein $R^{2a}$, $R^{2b}$, $R^{2c}$ and Y of each synthesized compound is defined in one row of table C.1 below.

The compounds were synthesized in analogy to Synthesis Example S.1.

TABLE C.1

| Ex. | $R^{2a}$, $R^{2b}$, $R^{2c}$ | —Y | HPLC-MS: Method, $R_t$ (min) & $[M + H]^+$ or $^1$H-NMR | | |
|---|---|---|---|---|---|
| 1-1 | Cl, F, Cl | —OCH$_3$ | A | 1.559 | 477.5 |
| 1-2 | Cl, F, Cl | —OH | A | 1.446 | 461.4 |
| 1-3 | Cl, F, Cl | —NHCH$_2$-cyclopropyl | $^1$H NMR (400 MHz, CDCl$_3$): δ 7.6 (m, 2H), 7.5 (m, 1H), 7.2 (m, 1H), 6.0 (s, 1H), 4.2 (d, 1H), 3.8 (d, 1H), 3.4-3.3 (m, 2H), 3.3-3.1 (m, 4H), 2.2-2.1 (m, 2H), 1.1-1.0 (m, 1H), 0.6-0.5 (m, 2H), 0.3-0.2 (m, 2H). | | |
| 1-4 | Cl, F, Cl | —NHCH$_2$C(═O)NHCH$_2$CF$_3$ | A | 1.355 | 599.8 |
| 1-5 | Cl, F, Cl | —NH-(1,1-dioxo-thietan-3-yl) | A | 1.402 | 564.3 |
| 1-6 | Cl, F, Cl | —NHCH$_2$-(2-pyridyl) | A | 1.248 | 551.4 |
| 1-7 | Cl, F, Cl | —NHCH$_2$-(2-pyrimidinyl) | A | 1.432 | 552.4 |
| 1-8 | Cl, F, Cl | —NHCH$_2$-(thietan-3-yl) | A | 1.464 | 546.8 |
| 1-9 | Cl, F, Cl | —NH-(thietan-3-yl) | A | 1.460 | 532.8 |
| 1-10 | Cl, F, Cl | —NH-(1-oxo-thietan-3-yl) | A | 1.305 | 548.8 |
| 1-11 | Cl, F, Cl | —NHCH$_2$CH═CH$_2$ | A | 1.440 | 500.8 |
| 1-12 | Cl, F, Cl | —NHCH$_2$CF$_3$ | A | 1.467 | 542.8 |
| 1-13 | Cl, F, Cl | —NH-(1-cyano-cyclopropyl) | A | 1.410 | 525.9 |
| 1-14 | Cl, F, Cl | —NHCH$_2$C≡CH | A | 1.409 | 498.8 |
| 1-15 | Cl, F, Cl | —NH$_2$ | A | 1.460 | 460.4 |
| 1-16 | Cl, F, Cl | —NHNH-(2-pyrimidinyl) | A | 1.446 | 553.4 |
| 1-17 | Cl, F, Cl | —NHCH$_2$CN | A | 1.515 | 499.4 |
| 1-18 | Cl, F, Cl | —NH—CH$_2$-(1,1-dioxo-thietan-3-yl) | A | 1.342 | 578.9 |
| 1-19 | Cl, F, Cl | —NH-(2,2-dimethyl-1,1-dioxo-thietan-3-yl) | A | 1.430 | 592.9 |
| 1-20 | Cl, F, Cl | —NH-(2,2-dimethylthietan-3-yl) | A | 1.538 | 561.3 |
| 1-21 | Cl, F, Cl | —NHCH$_2$-(1,1-dioxothietan-2-yl) | A | 1.372 | 579.3 |
| 1-22 | Cl, F, Cl | —NHCH$_2$—CH═CH—CH$_3$ (trans) | A | 1.479 | 514.9 |
| 1-23 | Cl, F, Cl | —NHCH═NOCH$_3$ | A | 1.513 | 518.0 |
| 1-24 | Cl, H, Cl | —NH$_2$ | A | 1.319 | 442.9 |
| 1-25 | Cl, H, Cl | —NHNH-(2-pyrimidinyl) | A | 1.317 | 535.9 |
| 1-26 | Cl, H, Cl | —NHCH═NOCH$_3$ | A | 1.488 | 500.0 |
| 1-27 | Cl, H, Cl | —NHCH$_2$-(2-pyridyl) | A | 1.259 | 534.0 |
| 1-28 | Cl, H, Cl | —NHCH$_2$C(═O)NHCH$_2$CF$_3$ | A | 1.369 | 582.0 |
| 1-29 | Cl, H, Cl | —NHCH$_2$CF$_3$ | A | 1.463 | 524.9 |
| 1-30 | Cl, H, Cl | —NHCH$_2$-(2-pyrimidinyl) | A | 1.357 | 535.0 |
| 1-31 | Cl, H, Cl | —NH-cyclopropyl | A | 1.404 | 483.0 |

TABLE C.1-continued

| Ex. | $R^{2a}, R^{2b}, R^{2c}$ | —Y | HPLC-MS: Method, $R_t$ (min) & $[M + H]^+$ or $^1$H-NMR | | |
|---|---|---|---|---|---|
| 1-32 | Cl, H, Cl | —NHCH$_2$-(thiazol-4-yl) | A | 1.380 | 539.9 |
| 1-33 | Cl, H, Cl | —NH-(1,1-dioxo-thietan-3-yl) | A | 1.347 | 547.0 |
| 1-34 | Cl, H, Cl | —NH-(thietan-3-yl) | A | 1.450 | 514.9 |
| 1-35 | Cl, H, Cl | —NHCH$_2$-cyclopropyl | A | 1.456 | 496.9 |
| 1-36 | Cl, H, Cl | —NHCH$_2$-(1,1-dioxo-thietan-3-yl) | A | 1.353 | 561.0 |
| 1-37 | Cl, H, Cl | —NH—CH(CH$_3$)—C(=O)NHCH$_2$CF$_3$ | A | 1.403 | 596.0 |
| 1-38 | Cl, H, Cl | —NH-[(4R)-2-ethyl-3-oxo-isoxazolidin-4-yl] | A | 1.377 | 556.0 |
| 1-39 | Cl, H, Cl | —NH-[(4R)-3-oxo-2-(2,2,2-trifluoroethyl)isoxazolidin-4-yl] | A | 1.425 | 609.9 |
| 1-40 | Cl, H, Cl | —N(CH$_3$)—CH$_2$-(2-pyridyl) | A | 1.284 | 548.5 |
| 1-41 | Cl, H, Cl | —N(CH$_2$CH$_3$)—CH$_2$-(2-pyridyl) | A | 1.313 | 562.1 |
| 1-42 | Cl, H, Cl | —NH-(1-oxo-thietan-3-yl) | A | 1.304 | 531.0 |
| 1-43 | Cl, H, Cl | —NH-[(4S)-2-ethyl-3-oxo-isoxazolidin-4-yl] | A | 1.396 | 556.0 |
| 1-44 | Cl, F, Cl | —NH—CH$_2$CH$_3$ | A | 1.428 | 489.0 |
| 1-45 | Cl, F, Cl | —NHCH$_2$C(=O)NHCH$_2$CH$_3$ | A | 1.350 | 548.0 |
| 1-46 | Cl, F, Cl | —NH-cyclopropyl | A | 1.430 | 503.0 |
| 1-47 | Cl, F, Cl | —NHCH$_2$C(=O)NH-cyclopropyl | A | 1.358 | 558.0 |
| 1-48 | Cl, F, Cl | —NHCH$_2$C(=O)NHCH$_2$CH$_2$F | A | 1.334 | 564.0 |
| 1-49 | Cl, F, Cl | —NHCH$_2$C(=O)NHCH$_2$CHF$_2$ | A | 1.359 | 582.0 |
| 1-50 | Cl, F, Cl | —NHCH$_2$-(2,2-difluorocyclopropyl) | A | 1.466 | 551.0 |
| 1-51 | Cl, F, Cl | —NHCH$_2$C(=O)NHCH$_2$C≡CH | A | 1.347 | 556.0 |
| 1-52 | Cl, F, Cl | —NHCH$_2$C(=O)—NHCH$_2$CH=CH$_2$ | A | 1.368 | 558.0 |
| 1-53 | Cl, F, Cl | —NHCH$_2$C(=O)—NHCH$_3$ | A | 1.315 | 532.0 |
| 1-54 | Cl, F, Cl | —NHCH$_2$-(4-thiazolyl) | A | 1.402 | 558.0 |
| 1-55 | Cl, F, Cl | —NH-(3-tetrahydrofuranyl) | A | 1.395 | 531.0 |
| 1-56 | Cl, H, Cl | —OH | $^1$H NMR (400 MHz, CDCl$_3$): δ 7.96 (d, 1H), 7.51 (s, 2H), 7.43 (s, 1H), 7.26 (d, 1H), 4.15 (d, 1H), 3.76 (d, 1H), 3.40-3.33 (m, 2H), 3.24-3.20 (m, 2H), 2.20-2.10 (m, 2H) | | |
| 1-57 | Cl, H, Cl | —NHCH$_2$-(thietan-3-yl) | A | 1.446 | 529.0 |
| 1-58 | Cl, F, Cl | —NHCH$_2$-cyclobutyl | A | 1.524 | 529.1 |
| 1-59 | Cl, F, Cl | —NH-(3,3-difluorocyclobutyl) | A | 1.471 | 551.0 |
| 1-60 | Cl, F, Cl | —NHCH$_2$-(3,3-difluorocyclobutyl) | A | 1.477 | 565.0 |
| 1-61 | Cl, F, Cl | —NH-[(4R)-3-oxo-2-(2,2,2-trifluoroethyl)isoxazolidin-4-yl] | A | 1.426 | 627.9 |
| 1-62 | Cl, F, Cl | —NH-[(4S)-2-ethyl-3-oxo-isoxazolidin-4-yl] | A | 1.385 | 574.0 |
| 1-63 | Cl, F, Cl | —NHCH$_2$-(3-pyridazinyl) | A | 1.303 | 552.9 |
| 1-64 | Cl, F, Cl | —NHCH$_2$-(5-bromopyrimidin-2-yl) | A | 1.454 | 632.8 |
| 1-65 | Cl, F, Cl | —NHCH$_2$-[(1-difluoromethyl)cyclopropyl] | A | 1.464 | 564.9 |
| 1-66 | Cl, F, Cl | —NHCH$_2$C(=O)—NHCH$_2$-cyclopropyl | A | 1.394 | 572.0 |
| 1-67 | Cl, F, Cl | —NH-cyclobutyl | A | 1.466 | 514.9 |
| 1-68 | Cl, F, Cl | —NHCH$_2$-[4,6-bis(trifluoromethyl)pyrimidin-2-yl] | A | 1.546 | 689.0 |
| 1-69 | Cl, F, Cl | —NHCH$_2$-(2,2-dichlorocyclopropyl) | A | 1.526 | 584.9 |
| 1-70 | Cl, F, Cl | —NHCH$_2$CCl=CCl$_2$ | A | 1.560 | 604.9 |
| 1-71 | Cl, F, Cl | —NHCH$_2$-[4-(trifluoromethyl)pyrimidin-2-yl] | A | 1.480 | 621.0 |
| 1-72 | Cl, F, Cl | —NHCH$_2$-(5-chloropyrimidin-2-yl) | A | 1.463 | 588.9 |
| 1-73 | Cl, F, Cl | —NHCH$_2$-(4-methyl-pyrimidin-2-yl) | A | 1.396 | 566.9 |
| 1-74 | Cl, F, Cl | —NHCH$_2$-(4,6-dimethyl-pyrimidin-2-yl) | A | 1.411 | 581.0 |
| 1-75 | Cl, F, Cl | —NHCH$_2$-[4-methyl-6-(trifluoromethyl)pyrimidin-2-yl | A | 1.496 | 635.0 |
| 1-76 | Cl, F, H | —NHCH$_2$-(2-pyrimidinyl) | A | 1.290 | 519.0 |
| 1-77 | Cl, F, H | —NHCH$_2$-(2-pyridyl) | A | 1.148 | 518.1 |
| 1-78 | Cl, F, H | —NHCH$_2$C(=O)NHCH$_2$CF$_3$ | A | 1.300 | 566.0 |
| 1-79 | Cl, F, H | —NH-(1,1-dioxo-thietan-3-yl) | A | 1.281 | 531.0 |
| 1-80 | Cl, F, Cl | —H | A | 1.525 | 445.9 |
| 1-81 | Cl, F, H | —OH | A | 1.346 | 428.0 |
| 1-82 | Cl, F, Cl | —NHCH$_2$-(2-methyl-tetrazol-5-yl) | A | 1.373 | 557.0 |
| 1-83 | Cl, F, Cl | —NHCH$_2$-(5-fluoro-pyrimidin-2-yl) | A | 1.418 | 571.0 |
| 1-84 | Cl, F, Cl | —NH-(3-pyridyl) | A | 1.241 | 538.0 |
| 1-85 | Cl, F, Cl | —NHNHC(=O)NHCH$_2$CF$_3$ | A | 1.338 | 600.9 |
| 1-86 | Cl, F, Cl | —NHCH$_2$-(1,2,4-oxadiazol-3-yl) | A | 1.375 | 542.9 |
| 1-87 | Cl, F, Cl | —NHCH$_2$-(1,3,4-thiadiazol-2-yl) | A | 1.363 | 558.9 |

TABLE C.1-continued

| Ex. | $R^{2a}, R^{2b}, R^{2c}$ | —Y | HPLC-MS: Method, $R_t$ (min) & $[M + H]^+$ or $^1$H-NMR | | |
|---|---|---|---|---|---|
| 1-88 | Cl, F, Cl | —NHCH$_2$-(4-chloro-pyrimidin-2-yl) | A | 1.440 | 588.8 |
| 1-89 | Cl, F, Cl | —NHCH$_2$-(5-methyl-pyrimidin-2-yl) | A | 1.404 | 567.0 |
| 1-90 | Cl, F, Cl | —NH-[(4R)-2-ethyl-3-oxo-isoxazolidin-4-yl] | A | 1.393 | 574.1 |
| 1-91 | Cl, F, Cl | —NHCH$_2$CH$_2$SO$_2$CH$_3$ | A | 1.336 | 567.0 |
| 1-92 | Cl, F, Cl | —NHCH$_2$-(1-methyl-1,2,3-triazol-4-yl) | A | 1.332 | 556.0 |
| 1-93 | Cl, F, Cl | —NHCH$_2$-(1-methyl-1,2,4-triazol-3-yl) | A | 1.307 | 556.0 |
| 1-94 | Cl, F, Cl | 3-ethyl-4-oxo-imidazolidin-1-yl | A | 1.375 | 558.0 |
| 1-95 | Cl, F, Cl | 4-oxo-3-(2,2,2-trifluoroethyl)imidazolidin-1-yl | A | 1.426 | 612.0 |
| 1-96 | Cl, F, Cl | —NHCH$_2$-(1-methyl-tetrazol-5-yl) | A | 1.351 | 557.0 |
| 1-97 | Cl, F, Cl | —NHNHC(═O)NHCH$_2$CF$_2$H | $^1$H NMR (400 MHz, d$_6$-DMSO): δ 10.0 (s, 1H), 8.2 (s, 1H), 7.8 (m, 2H), 7.6 (d, 1H), 7.5 (d, 1H), 6.8 (s, 1H), 6.2-5.8 (m, 1H), 4.5-4.3 (m, 2H), 3.6-3.4 (m, 2H), 3.2-3.0 (m, 4H), 2.1-1.9 (m, 2H) | | |
| 1-98 | Cl, F, Cl | —NHNHC(═O)NHCH$_2$CH$_3$ | A | 1.309 | 547.0 |
| 1-99 | Cl, F, Cl | —NH-(5-pyrimidinyl) | A | 1.404 | 539.0 |
| 1-100 | Cl, F, Cl | —NHNHC(═O)NHCH$_3$ | A | 1.275 | 533.0 |
| 1-101 | Cl, F, Cl | —NHCH$_2$-(oxazol-2-yl) | A | 1.387 | 554.1 |
| 1-102 | Cl, F, Cl | —NHN(CH$_3$)-(2-pyrimidinyl) | A | 1.407 | 568.1 |
| 1-103 | Cl, F, Cl | —NHCH$_2$CH$_2$SCH$_3$ | A | 1.466 | 535.0 |
| 1-104 | Cl, F, Cl | —NH-[2-oxo-1-(2,2,2-trifluoroethyl)pyrrolidin-3-yl] | A | 1.413 | 626.1 |
| 1-105 | Cl, F, Cl | —NH-(2-pyrazinyl) | A | 1.467 | 539.0 |
| 1-106 | Cl, F, Cl | —NH-(1-methyl-pyrazol-3-yl) | A | 1.422 | 541.1 |
| 1-107 | Cl, F, Cl | —NHCH$_2$-(1-(trifluoromethyl)cyclopropyl) | A | 1.525 | 583.1 |
| 1-108 | Cl, F, Cl | —NH-(3-methyl-isothiazol-5-yl) | A | 1.460 | 558.0 |
| 1-109 | Cl, F, Cl | —NHNH-(2-pyridyl) | A | 1.164 | 553.0 |
| 1-110 | Cl, F, Cl | —NH-(3-pyridazinyl) | A | 1.419 | 539.0 |
| 1-111 | Cl, F, Cl | —NHCH$_2$-(1,3-dioxolan-2-yl) | A | 1.399 | 547.1 |
| 1-112 | Cl, F, Cl | —NH-(1-methyl-2-oxo-pyrrolidin-3-yl) | A | 1.336 | 558.0 |
| 1-113 | Cl, F, Cl | —NHCH$_2$-(4-pyrimidinyl) | A | 1.355 | 553.1 |
| 1-114 | Cl, F, Cl | —NHCH$_2$-(1-methyl-pyrazol-3-yl) | A | 1.376 | 555.1 |
| 1-115 | Cl, F, Cl | —NHCH$_2$CH$_2$CF$_2$H | A | 1.444 | 539.1 |
| 1-116 | Cl, F, Cl | —NHCH$_2$CH$_2$-(1,3-dioxolan-2-yl) | A | 1.421 | 561.1 |
| 1-117 | Cl, F, Cl | —NH-(1-ethyl-2-oxo-pyrrolidin-3-yl) | A | 1.369 | 572.1 |
| 1-118 | Cl, F, Cl | —NHCH$_2$-(4-oxazolyl) | A | 1.374 | 542.0 |
| 1-119 | Cl, F, Cl | —NHCH$_2$-(4-methyl-1,2,4-triazol-3-yl) | A | 1.207 | 556.1 |
| 1-120 | Cl, F, Cl | —NHCH$_2$-(3-isoxazolyl) | A | 1.403 | 542.1 |
| 1-121 | Cl, F, Cl | —NHCH$_2$-(2-methyl-pyrazol-3-yl) | A | 1.369 | 555.1 |
| 1-122 | Cl, F, Cl | —NH-(1-methyl-5-oxo-1,2,4-triazol-4-yl) | A | 1.324 | 558.1 |
| 1-123 | F, H, OCF$_3$ | —NHCH$_2$-(2-pyrimidinyl) | A | 1.342 | 569.1 |
| 1-124 | F, H, OCF$_3$ | —NHCH$_2$-(2-pyridyl) | A | 1.177 | 568.1 |
| 1-125 | Cl, F, Cl | —NH-[(4R)-2-methyl-3-oxo-isoxazolidin-4-yl] | A | 1.358 | 560.1 |
| 1-126 | Cl, F, Cl | —NHCH$_2$-cyclopentyl | A | 1.558 | 543.0 |
| 1-127 | Cl, F, Cl | —NHCH$_2$-(2-tetrahydrofuranyl) | A | 1.439 | 545.1 |
| 1-128 | Cl, F, Cl | —NHCH$_2$CF$_2$H | A | 1.438 | 524.9 |
| 1-129 | Cl, F, Cl | —NHCH$_2$CFH$_2$ | A | 1.406 | 507.1 |
| 1-130 | Cl, F, Cl | —NHCH$_2$-(1-cyano-cyclopropyl) | A | 1.412 | 540.1 |
| 1-131 | Cl, F, Cl | —NH-(2,2-difluorocyclopropyl) | A | 1.450 | 537.0 |
| 1-132 | Cl, F, Cl | —NHCH$_2$-(1-oxo-thietan-3-yl) | A | 1.302 | 563.1 |
| 1-133 | Cl, F, Cl | —NH-(4-pyridazinyl) | A | 1.277 | 539.0 |
| 1-134 | F, H, OCF$_3$ | —NH-(1,1-dioxo-thietan-3-yl) | A | 1.330 | 581.0 |
| 1-135 | F, H, OCF$_3$ | —NHCH$_2$C(═O)NHCH$_2$CF$_3$ | A | 1.356 | 616.1 |
| 1-136 | Cl, F, Cl | —N═S(CH$_2$CH$_3$)$_2$ | A | 1.349 | 549.0 |
| 1-137 | Cl, F, Cl | —NH-(1-cyano-cyclobutyl) | A | 1.454 | 540.1 |
| 1-138 | F, H, OCF$_3$ | —NH-[(4R)-2-ethyl-3-oxo-isoxazolidin-4-yl] | A | 1.363 | 590.1 |

Synthesis Example S.1

N-(Cyclopropylmethyl)-7-[5-(3,5-dichloro-4-fluoro-phenyl)-5-(trifluoromethyl)-4H-isoxazol-3-yl]indane-4-carboxamide (Compound example 1-3; compound of formula C.1, wherein $R^{2a}$ and $R^{2c}$ are Cl, $R^{2b}$ is F, and —Y is —NHCH$_2$-cyclopropyl)

(7-Acetylindan-4-yl) trifluoromethanesulfonate (CAS 1312609-69-0) was synthesized as described in US 2011/0152246 (p. 118, compound I-IIIf).

Step 1: Methyl 7-acetylindane-4-carboxylate

To a solution of (7-acetylindan-4-yl) trifluoromethanesulfonate (40 g) in methanol (357 mL) were added Na$_2$CO$_3$ (27.5 g) and [1,1'-bis(diphenylphosphino)ferrocene]dichloro-palladium(II) (Pd(dppf)Cl$_2$, 9.5 g). The solution was pressurized with carbon monoxide (50 Psi) and heated at 50° C. for 5 h. Then, the mixture was filtered and the filtrate was concentrated. The residue was dissolved in CH$_2$Cl$_2$ and washed with brine, dried (Na$_2$SO$_4$), filtered and concentrated to give a residue, which was purified by flash chromatography on silica gel (petroleum ether/ethyl acetate) to afford the product (18.3 g, 64%).

$^1$H NMR (400 MHz, CDCl$_3$): δ 7.9 (d, 1H), 7.7 (d, 1H), 4.0 (s, 3H), 3.3-3.2 (m, 4H), 2.6 (s, 3H), 2.1 (m, 2H).

Step 2: Methyl 7-[(3-(3,5-dichloro-4-fluoro-phenyl)-4,4,4-trifluoro-but-2-enoyl]indane-4-carboxylate To a solution of the product of step 1 (12 g) and 1-(3,5-dichloro-4-fluoro-phenyl)-2,2,2-trifluoro-ethanone (28.7 g, CAS 1190865-44-1) in DCE (100 mL) was added K$_2$CO$_3$ (7.6 g) and triethylamine (7.6 mL). The reaction was stirred at reflux overnight. Then, the mixture was cooled to r.t., filtered and concentrated to give a residue, which was purified by flash chromatography on silica gel (petroleum ether/ethyl acetate) to afford the product (18.75 g, 74%).

$^1$H NMR (400 MHz, CDCl$_3$): δ 7.8 (m, 1H), 7.5 (m, 1H), 7.3 (m, 1H), 7.2 (m, 2H), 3.9 (s, 3H), 3.2 (m, 2H), 3.1 (m, 2H), 2.0 (m, 2H).

Step 3: Methyl 7-[5-(3,5-dichloro-4-fluoro-phenyl)-5-(trifluoromethyl)-4H-isoxazol-3-yl]indane-4-carboxylate (Compound Example 1-1)

To a solution of the product of step 2 (10 g) in THF (167 mL) was added hydroxylamine hydrochloride (3 g), followed by a drop wise addition of a solution of NaOH (3.5 g) in water (83 mL). The reaction was stirred at r.t. overnight, and concentrated. The residue was taken up in ethyl acetate, and the organic layer was washed with water (3×), dried (Na$_2$SO$_4$), filtered and concentrated to give a residue, which was purified by flash chromatography on silica gel (petroleum ether/ethyl acetate) to afford the product (6 g, 58%).

$^1$H NMR (400 MHz, MeOH-d$_4$): δ 7.9 (d, 1H), 7.8 (m, 2H), 7.4 (d, 1H), 4.3 (d, 1H), 4.1 (d, 1H), 3.9 (s, 3H), 3.3 (m, 2H), 3.2 (m, 2H), 2.1 (m, 2H).

Step 5: 7-[5-(3,5-Dichloro-4-fluoro-phenyl)-5-(trifluoromethyl)-4H-isoxazol-3-yl]indane-4-carboxylic acid (Compound Example 1-2)

At 0° C., the product of step 4 (4.5 g) in THF (45 mL) was treated with a solution of LiOH (0.45 g) in water (5 mL), and the mixture stirred at r.t. for 5 h. Then, more LiOH (0.2 g) was added, and the reaction was stirred at r.t. overnight. Subsequently, 10% aqueous HCl was added to adjust the pH of the reaction to pH 3-4. The organic layer was diluted with CH$_2$Cl$_2$, washed with water (2×), dried (Na$_2$SO$_4$), filtered, and concentrated. The obtained residue was purified by trituration (hexanes) to afford the product (3.35 g, 77%).

$^1$H NMR (400 MHz, d$_6$-DMSO): δ 13.0 (s, 1H), 7.9-7.8 (m, 3H), 7.6-7.5 (m, 1H), 4.4-4.3 (m, 2H), 3.3-3.2 (m, 2H), 3.2-3.0 (m, 2H), 2.1-1.9 (m, 2H).

Step 6: N-(Cyclopropylmethyl)-7-[5-(3,5-dichloro-4-fluoro-phenyl)-5-(trifluoromethyl)-4H-isoxazol-3-yl]indane-4-carboxamide (Compound Example 1-3)

To a solution of the product of step 5 (0.23 g), cyclopropylmethylamine (0.04 g) and PyBroP (0.28 g) in CH$_2$Cl$_2$ (15 mL) at r.t. was added N,N-diisopropylethylamine (0.26 g). The reaction was stirred at r.t. overnight. Then, the reaction was diluted with CH$_2$Cl$_2$, washed with water (2×), dried (Na$_2$SO$_4$), filtered and concentrated to give a residue, which was purified by flash chromatography on silica gel to afford the product (0.21 g, 82%).

$^1$H NMR (400 MHz, CDCl$_3$): δ 7.6 (m, 2H), 7.5 (m, 1H), 7.2 (m, 1H), 6.0 (s, 1H), 4.2 (d, 1H), 3.8 (d, 1H), 3.4-3.3 (m, 2H), 3.3-3.1 (m, 4H), 2.2-2.1 (m, 1H), 1.1-1.0 (m, 1H), 0.6-0.5 (m, 2H), 0.3-0.2 (m, 2H).

C.2 Compound Examples 2

Compound examples 2-1 to 2-24 correspond to compounds of formula C.2:

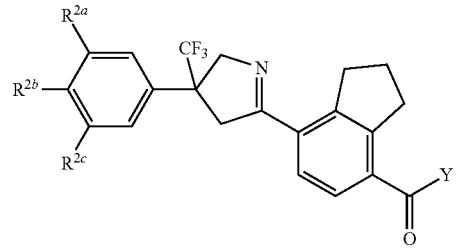

C.2 wherein $R^{2a}$, $R^{2b}$, $R^{2c}$ and Y of each synthesized compound is defined in one row of table C.2 below.

The compounds were synthesized in analogy to Synthesis Example S.2.

TABLE C.2

| Ex. | $R^{2a}$, $R^{2b}$, $R^{2c}$ | —Y | HPLC-MS: Method, $R_t$ (min) & [M + H]$^+$ or $^1$H-NMR | | |
|---|---|---|---|---|---|
| 2-1 | Cl, F, Cl | —OH | A | 1.500 | 459.4 |
| 2-2 | Cl, F, Cl | —OCH$_3$ | A | 1.661 | 473.4 |

TABLE C.2-continued

| Ex. | $R^{2a}, R^{2b}, R^{2c}$ | —Y | HPLC-MS: Method, $R_t$ (min) & $[M + H]^+$ or $^1$H-NMR | | |
|---|---|---|---|---|---|
| 2-3 | Cl, F, Cl | —NH-(1,1-dioxo-thietan-3-yl) | $^1$H NMR (400 MHz, CDCl$_3$): δ 7.5 (m, 2H), 7.35 (m, 2H), 7.2 (m, 1H), 6.7 (d, 1H), 5.0-4.85 (m, 2H), 4.7-4.6 (m, 2H), 4.45 (d, 1H), 4.1-4.0 (m, 2H), 3.8 (d, 1H), 3.4 (d, 1H), 3.3-3.1 (m, 4H), 2.2-2.1 (m, 2H). | | |
| 2-4 | Cl, F, Cl | —NH-(thietan-3-yl) | A | 1.526 | 532.2 |
| 2-5 | Cl, F, Cl | —NHCH$_2$-(thietan-3-yl) | A | 1.527 | 544.8 |
| 2-6 | Cl, F, Cl | —NHCH$_2$-cyclopropyl | A | 1.393 | 514.6 |
| 2-7 | Cl, F, Cl | —NHCH$_2$C(=O)NHCH$_2$CF$_3$ | A | 1.311 | 599.6 |
| 2-8 | Cl, F, Cl | —NH-(1-oxo-thietan-3-yl) | A | 1.395 | 546.7 |
| 2-9 | Cl, F, Cl | —NHCH$_2$-(2-pyridyl) | A | 1.125 | 549.9 |
| 2-10 | Cl, F, Cl | —NHCH$_2$-(2-pyrimidinyl) | A | 1.284 | 550.9 |
| 2-11 | Cl, F, Cl | —NH—CH$_2$-(1,1-dioxo-thietan-3-yl) | A | 1.265 | 576.9 |
| 2-12 | Cl, H, Cl | —NHNH-(2-pyrimidinyl) | A | 1.241 | 534.0 |
| 2-13 | Cl, H, Cl | —NHCH$_2$-(2-pyridyl) | A | 1.158 | 532.0 |
| 2-14 | Cl, H, Cl | —NHCH$_2$C(=O)NHCH$_2$CF$_3$ | A | 1.302 | 580.0 |
| 2-15 | Cl, H, Cl | —OH | A | 1.351 | 441.9 |
| 2-16 | Cl, H, Cl | —OCH$_3$ | A | 1.529 | 455.9 |
| 2-17 | Cl, H, Cl | —NHCH$_2$-(2-pyrimidinyl) | A | 1.291 | 533.0 |
| 2-18 | Cl, H, Cl | —NH-cyclopropyl | A | 1.347 | 481.0 |
| 2-19 | Cl, H, Cl | —NH-(1,1-dioxo-thietan-3-yl) | A | 1.289 | 545.0 |
| 2-20 | Cl, H, Cl | —NHCH$_2$-(4-thiazol) | A | 1.319 | 538.0 |
| 2-21 | Cl, H, Cl | —NH-[(4R)-2-ethyl-3-oxo-isoxazolidin-4-yl] | A | 1.325 | 554.0 |
| 2-22 | Cl, H, Cl | —NHCH(CH$_3$)-C(=O)NHCH$_2$CF$_3$ | A | 1.357 | 594.0 |
| 2-23 | Cl, H, Cl | —NH-(thietan-3-yl) | A | 1.404 | 513.0 |
| 2-24 | Cl, H, Cl | —NH-(1-oxo-thietan-3-yl) | A | 1.232 | 529.0 |

Synthesis Example S.2

7-[3-(3,5-Dichloro-4-fluoro-phenyl)-3-(trifluoromethyl)-2,4-dihydropyrrol-5-yl]-N-(1,1-dioxothietan-3-yl)indane-4-carboxamide (Compound example 2-3; compound of formula C.2, wherein $R^{2a}$ and $R^{2c}$ are Cl, $R^{2b}$ is F and —Y is —NH-(1,1,-dioxo-thietan-3-yl))

Step 1: Methyl 7-[3-(3,5-dichloro-4-fluoro-phenyl)-4,4,4-trifluoro-3-(nitromethyl)butanoyl]indane-4-carboxylate To a solution of methyl 7-[(3-(3,5-dichloro-4-fluoro-phenyl)-4,4,4-trifluoro-but-2-enoyl]indane-4-carboxylate (i.e. the product of Synthesis Example S.1, step 2, 10 g) in CH$_3$CN (400 mL) was added 1,8-diazabicyclo[5.4.0]undec-7-ene ("DBU", 16.6 g) and CH$_3$NO$_2$ (6 g) at r.t. The mixture was stirred for 20 min, and then adjusted to pH 6 with aqueous 1 M HCl solution. The aqueous phase was extracted with ethyl acetate (3×150 mL). The organic layers were combined, concentrated and the obtained residue was purified by flash chromatography on silica gel (petroleum ether/ethyl acetate) to afford the product (6 g, 52%).

$^1$H NMR (400 MHz, CDCl$_3$): δ 7.89 (d, 1H), 7.66 (d, 1H), 7.21-7.19 (m, 2H), 5.52 (d, 1H), 5.39 (d, 1H), 4.04 (d, 1H), 3.91-3.87 (m, 4H), 3.25-3.15 (m, 2H), 3.06-2.99 (m, 2H), 2.1-1.9 (m, 2H).

Step 2: Methyl 7-[3-(3,5-dichloro-4-fluoro-phenyl)-3-(trifluoromethyl)-2,4-dihydropyrrol-5-yl]indane-4-carboxylate (Compound 2-2)

To a solution of the product of step 2 (6 g) in CH$_3$OH (100 mL) was added acetic acid (100 mL) and iron powder (1.9 g). The mixture was stirred at 70° C. overnight, and then concentrated. Water (20 mL) was added and the aqueous layer was extracted with ethyl acetate (3×100 mL). The combined organic layers were concentrated and the obtained residue was purified by flash chromatography on silica gel (petroleum ether/ethyl acetate) to afford the product (3.1 g, 56%).

$^1$H NMR (400 MHz, CDCl$_3$): δ 7.90 (d, 1H), 7.47 (d, 1H), 7.35-7.30 (m, 2H), 4.94 (d, 1H), 4.47 (d, 1H), 3.93 (s, 3H), 3.81 (d, 1H), 3.49 (d, 1H), 3.35-3.25 (m, 2H), 3.25-3.20 (m, 2H), 2.15-1.06 (m, 2H).

Step 3: 7-[3-(3,5-Dichloro-4-fluoro-phenyl)-3-(trifluoromethyl)-2,4-dihydropyrrol-5-yl]indane-4-carboxylic acid (Compound 2-1)

At 0° C., the product of step 2 (1.66 g) in THF (25 mL) was treated with a solution of LiOH (0.17 g) in water (10 mL), and the mixture stirred at r.t. overnight. Then, more LiOH (0.1 g) was added, and the reaction was stirred at 30° C. for 4 h. 10% aqueous HCl was added to adjust the pH of the reaction to pH 3-4. More water was added, and the aqueous layer was extracted with CH$_2$Cl$_2$ (3×). The combined organic layers were dried (Na$_2$SO$_4$), filtered, and concentrated. The obtained residue was purified by trituration (hexanes) to afford the product (1.0 g, 62%).

$^1$H NMR (400 MHz, d$_6$-DMSO): δ 13.0 (s, 1H), 7.9-7.75 (m, 3H), 7.75-7.6 (m, 1H), 4.9 (d, 1H), 4.45 (d, 1H), 3.9-3.7 (m, 2H), 3.3-3.1 (m, 2H), 2.1-1.9 (m, 2H).

Step 4: 7-[3-(3,5-Dichloro-4-fluoro-phenyl)-3-(trifluoromethyl)-2,4-dihydropyrrol-5-yl]-N-(1,1-dioxothietan-3-yl)indane-4-carboxamide (Compound 2-3)

To a solution of the product of step 3 (0.2 g), 1,1-dioxothietan-3-amine hydrochloride (0.08 g) and PyBroP (0.24 g) in CH$_2$Cl$_2$ (20 mL) at r.t. was added N,N-diisopropylethylamine (0.22 g). The reaction was stirred at r.t. overnight. Then, the reaction was diluted with CH$_2$Cl$_2$, washed with water (2×), dried (Na$_2$SO$_4$), filtered and concentrated to give a residue, which was purified by flash chromatography on silica gel to afford the product (0.15 g, 55%).

$^1$H NMR (400 MHz, CDCl$_3$): δ 7.5 (m, 2H), 7.35 (m, 2H), 7.2 (m, 1H), 6.7 (d, 1H), 5.0-4.85 (m, 2H), 4.7-4.6 (m, 2H), 4.45 (d, 1H), 4.1-4.0 (m, 2H), 3.8 (d, 1H), 3.4 (d, 1H), 3.3-3.1 (m, 4H), 2.2-2.1 (m, 2H).

C.3 Compound Examples 3

Compound examples 3-1 to 3-13 correspond to compounds of formula C.3:

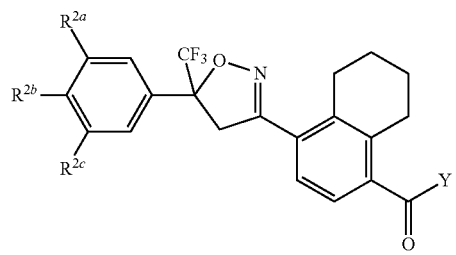

C.3 wherein R$^{2a}$, R$^{2b}$, R$^{2c}$ and Y of each synthesized compound is defined in one row of table C.3 below.

The compounds were synthesized in analogy to Synthesis Example S.3.

Synthesis Example S.3

8-[5-(3,5-dichlorophenyl)-5-(trifluoromethyl)-4H-isoxazol-3-yl]-N-(2,2,2-trifluoroethyl)tetralin-5-carboxamide (Compound example 3-5; compound of formula C.3, wherein R$^{2a}$ and R$^{2c}$ are Cl, R$^{2b}$ is H, and —Y is NHCH$_2$CF$_3$)

Step 1: 5-Methoxytetralin

To a mixture of tetralin-5-ol (32 g) and K$_2$CO$_3$ (64 g) in acetone (600 mL) was added (CH$_3$)$_2$SO$_4$ (60 g), and the mixture was stirred at reflux for 15 h. Then, the mixture was filtered and concentrated. The crude product was purified by flash chromatography on silica gel (petroleum ether/ethyl acetate) to afford the product (34 g, 88%).

$^1$H NMR (400 MHz, CDCl$_3$): δ 7.12 (m, 1H), 6.81-6.70 (m, 2H), 3.86 (s, 3H), 2.81 (m, 2H), 2.71 (m, 2H), 1.91-1.77 (m, 4H).

Step 2: 1-(8-Methoxytetralin-5-yl)ethanone

At 0° C., acetyl chloride ("AcCl", 16 g) was added dropwise to a mixture of the product of step 1 (25 g) and AlCl$_3$ (28 g) in DCE (300 mL). The reaction was stirred at 25° C. for 10 h, and then poured into ice water (200 mL). The aqueous layer was extracted with CH$_2$Cl$_2$ (3×300 mL), and the combined organic layers were dried (Na$_2$SO$_4$), filtered and concentrated to give the crude product (27 g) which was used in the next step without any further purification.

TABLE C.3

| Ex. | R$^{2a}$, R$^{2b}$, R$^{2c}$ | —Y | HPLC-MS: Method, R$_t$ (min) & [M + H]$^+$ or $^1$H-NMR (400 MHz, CDCl$_3$) | | |
|---|---|---|---|---|---|
| 3-1 | Cl, H, Cl | —OCH$_3$ | δ 7.64 (d, 1H), 7.51 (s, 2H), 7.45 (s, 1H), 7.18 (d, 1H), 4.09 (d, 2H), 3.90 (s, 3H), 3.73 (d, 1H), 3.08 (m, 2H), 2.94 (m, 2H), 1.86-1.72 (m, 4H) | | |
| 3-2 | Cl, H, Cl | —OH | $^1$H NMR (400 MHz, CDCl$_3$): δ 7.87 (d, 1H), 7.65 (s, 2H), 7.50 (s, 1H), 7.23 (d, 1H), 4.11 (d, 1H), 3.74 (d, 1H), 3.19 (m, 2H), 2.97 (m, 2H), 1.82-1.81 (m, 4H). | | |
| 3-3 | Cl, H, Cl | —NH-(1,1-dioxo-thietan-3-yl) | A | 1.361 | 561.0 |
| 3-4 | Cl, H, Cl | —NHCH$_2$C(=O)NHCH$_2$CF$_3$ | A | 1.391 | 596.0 |
| 3-5 | Cl, H, Cl | —NHCH$_2$CF$_3$ | A | 1.466 | 539.0 |
| 3-6 | Cl, H, Cl | —NH-cyclopropyl | A | 1.424 | 497.0 |
| 3-7 | Cl, H, Cl | —NH-(thietan-3-yl) | A | 1.446 | 529.0 |
| 3-8 | Cl, H, Cl | —NHCH(CH$_3$)-C(=O)NHCH$_2$CF$_3$ | A | 1.400 | 610.0 |
| 3-9 | Cl, H, Cl | —NH-[(4R)-2-ethyl-3-oxo-isoxazolidin-4-yl] | A | 1.379 | 570.0 |
| 3-10 | Cl, H, Cl | —NHCH$_2$-(thiazol-4-yl) | A | 1.389 | 554.0 |
| 3-11 | Cl, H, Cl | —NHCH$_2$-(2-pyrimidinyl) | A | 1.371 | 549.0 |
| 3-12 | Cl, H, Cl | —NHCH$_2$-(2-pyridyl) | A | 1.243 | 548.0 |
| 3-13 | Cl, H, Cl | —NH-(1-oxo-thietan-3-yl) | A | 1.293 | 545.0 |

$^1$H NMR (400 MHz, CDCl$_3$): δ 7.64 (d, 1H), 6.71 (d, 1H), 3.89 (s, 3H), 3.10-3.00 (m, 2H), 2.68 (m, 2H), 2.56 (s, 3H), 1.83-1.68 (m, 4H).

Step 3: 1-(8-Hydroxytetralin-5-yl)ethanone

The crude product of step 2 (30 g) in DCE (1.5 L) was treated with AlCl$_3$ (30 g) and the mixture was stirred at 100° C. overnight. Then, the solution was poured into ice water (500 mL) and extracted with CH$_2$Cl$_2$. The combined organic layers were dried (Na$_2$SO$_4$), filtered and concentrated to give a residue, which was purified by flash chromatography on silica gel (petroleum ether/ethyl acetate) to afford the product (15 g, 50%).

$^1$H NMR (400 MHz, CDCl$_3$): δ 7.56 (d, 1H), 6.69 (d, 1H), 3.06 (m, 2H), 2.68 (m, 2H), 2.56 (s, 3H), 1.87-1.80 (m, 2H), 1.80-1.72 (m, 2H).

Step 4: (8-Acetyltetralin-5-yl) trifluoromethanesulfonate

To the product of step 3 (15 g) and Et$_3$N (20 g) in CH$_2$Cl$_2$ (500 mL) at 0° C. was added triflic anhydride ("Tf$_2$O", 33 g). The mixture was stirred at 0° C. for 30 min. Then, the solution was poured onto ice water (500 mL) and extracted with CH$_2$Cl$_2$. The combined organic layers were dried (Na$_2$SO$_4$), filtered and concentrated to give a residue, which was purified by flash chromatography on silica gel (petroleum ether/ethyl acetate) to afford the product (25 g, 95%).

$^1$H NMR (400 MHz, CDCl$_3$): δ 7.55-7.46 (m, 1H), 7.18 (m, 1H), 3.03-2.95 (m, 2H), 2.84 (m, 2H), 2.58 (s, 3H), 1.91-1.79 (m, 4H).

Step 5: Methyl 8-acetyltetralin-5-carboxylate

To a solution of the product of step 4 (25 g) in methanol (500 mL) were added Na$_2$CO$_3$ (30 g) and [1,1'-bis(diphenylphosphino)ferrocene]dichloropalladium(II) (Pd(dppf)C$_{12}$, 3 g). The solution was pressurized with carbon monoxide (50 Psi) and heated at 50° C. overnight. Then, the mixture was filtered and the filtrate was concentrated. The residue was dissolved in CH$_2$Cl$_2$ and washed with water, dried (Na$_2$SO$_4$), filtered and concentrated to give a residue, which was purified by flash chromatography on silica gel (petroleum ether/ethyl acetate) to afford the product (15 g, 65%).

$^1$H NMR (400 MHz, CDCl$_3$): δ 7.63 (d, 1H), 7.34 (d, 1H), 3.89 (s, 3H), 3.04 (m, 2H), 2.92 (m, 2H), 2.57 (s, 3H), 1.77 (m, 4H).

Step 6: Methyl 8-[3-(3,5-dichlorophenyl)-4,4,4-trifluoro-but-2-enoyl]tetralin-5-carboxylate To a solution of the product of step 5 (10 g) and 1-(3,5-dichlorophenyl)-2,2,2-trifluoro-ethanone (15.7 g, CAS 130336-16-2) in DCE (100 mL) was added K$_2$CO$_3$ (5.9 g) and Et$_3$N (10 mL). The reaction was stirred for 16 h at 100° C. Then, the mixture was filtered and concentrated to give a residue, which was purified by flash chromatography on silica gel (petroleum ether/ethyl acetate) to afford the product (17 g, 86%).

$^1$H NMR (400 MHz, CDCl$_3$): δ 7.66 (d, 1H), 7.38 (s, 2H), 7.34 (d, 1H), 7.11 (m, 2H), 4.01 (s, 3H), 3.11-3.03 (m, 2H), 2.88 (m, 2H), 1.87-1.77 (m, 4H).

Step 7: Methyl 8-[5-(3,5-dichlorophenyl)-5-(trifluoromethyl)-4H-isoxazol-3-yl]tetralin-5-carboxylate (Compound Examples 3-1)

To a solution of the product of step 2 (17 g) in DCE (500 mL) was added hydroxylamine hydrochloride (5.3 g) and tetrabutylammoniumbromid ("TBAB", 6.2 g), followed by drop wise addition of a solution of NaOH (6.1 g) in water (70 mL). The reaction was stirred for 12 h at 25° C. The organic layer was washed with water (3×100 mL), dried (Na$_2$SO$_4$), filtered and concentrated to give a residue, which was purified by flash chromatography on silica gel (petroleum ether/ethyl acetate) to afford the product (12 g, 67%).

$^1$H NMR (400 MHz, CDCl$_3$): δ 7.64 (d, 1H), 7.51 (s, 2H), 7.45 (s, 1H), 7.18 (d, 1H), 4.09 (d, 2H), 3.90 (s, 3H), 3.73 (d, 1H), 3.08 (m, 2H), 2.94 (m, 2H), 1.86-1.72 (m, 4H).

Step 8: 8-[5-(3,5-dichlorophenyl)-5-(trifluoromethyl)-4H-isoxazol-3-yl]tetralin-5-carboxylic acid (Compound Examples 3-2)

The product of step 7 (12 g) in THF (100 mL) was treated with a solution of LiOH (3 g) in water (30 mL), and the mixture stirred at r.t. for 12 h and at 80° C. for 5 h. Then, the pH of the reaction adjusted to pH 3 using 1 M aqueous HCl solution. The aqueous layer was extracted with methyl-tert-butylether ("MTBE", 3×100 mL). The organic layers were combined, dried (Na$_2$SO$_4$), filtered, and concentrated to afford the product (10 g, 88%).

$^1$H NMR (400 MHz, CDCl$_3$): δ 7.87 (d, 1H), 7.65 (s, 2H), 7.50 (s, 1H), 7.23 (d, 1H), 4.11 (d, 1H), 3.74 (d, 1H), 3.19 (m, 2H), 2.97 (m, 2H), 1.82-1.81 (m, 4H).

Step 9: 8-[5-(3,5-dichlorophenyl)-5-(trifluoromethyl)-4H-isoxazol-3-yl]-N-(2,2,2-trifluoroethyl) tetralin-5-carboxamide To a solution of the product of step 8 (0.3 g), 2,2,2-trifluoroethylamine (0.08 g) and PyBroP (0.37 g) in CH$_2$Cl$_2$ (10 mL) at r.t. was added N,N-diisopropylethylamine (0.27 g). The reaction was stirred at r.t. overnight. Then, the reaction was concentrated to give a residue, which was purified by flash chromatography on silica gel to afford the product (0.19 g, 52%).

$^1$H NMR (400 MHz, CDCl$_3$): δ 7.55 (s, 2H), 7.45 (s, 1H), 7.2 (d, 1H), 7.1 (d, 1H), 6.0 (m, 1H), 4.2-4.0 (m, 3H), 3.7 (d, 1H), 2.9 (m, 2H), 2.85 (m, 2H), 1.8-1.7 (m, 4H).

C.4 Compound Examples 4

Compound examples 4-1 to 4-2 correspond to compounds of formula C.4:

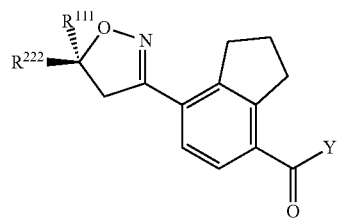

C.4 wherein R$^{111}$, R$^{222}$ and Y of each compound is defined in one row of table C.4 below.

The compounds 4-1 and 4-2 were obtained from the corresponding racemic compound example 1-7 by separation using a preparative chiral HPLC (method B). Assignment of the absolute configuration was done by X-ray crystallography.

Method B (preparative chiral HPLC). Instrument: Thar SFC Pre-80. Column: Chiralpak AS-H 5 mm, 3.0 cm id×25 cm L Mobile phase: A for SFC $CO_2$ and B for MeOH (0.1% $NH_4OH$). Gradient: A:B=65:35. Flow rate: 70 mL/min. Detection wavelength: 220 nm. System Back Pressure: 100 bar.

Method C (analytical chiral HPLC). Instrument: Thar analytical SFC. Column: Chiralpak AS-H 5 mm, 0.46 cm id×15 cm L Mobile phase: A for SFC $CO_2$ and B for Methanol (0.05% Isopropylamine). Gradient: B in A from 10% to 40% in 5 minutes. Flow rate: 4.0 mL/min. Detection wavelength: 220 nm. System Back Pressure: 100 bar.

TABLE C.4

| Ex. | $R^{111}$ | $R^{222}$ | —Y | Chiral analytical HPLC Method, retention time | |
|---|---|---|---|---|---|
| 4-1 | 3,5-Dichloro-4-fluoro-phenyl | $CF_3$ | —$NHCH_2$-(2-pyrimidinyl) | C | 2.78 min |
| 4-2 | $CF_3$ | 3,5-Dichloro-4-fluoro-phenyl | —$NHCH_2$-(2-pyrimidinyl) | C | 3.44 min |

C.5 Compound Examples 5

Compound examples 5-1 to 5-2 corresponds to compounds of formula C.5:

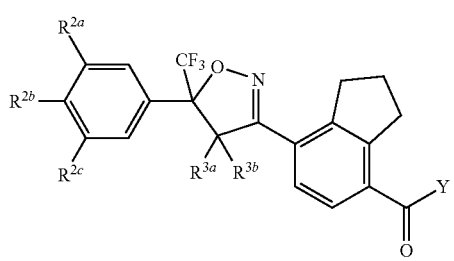

C.5 wherein $R^{2a}$, $R^{2b}$, $R^{2c}$ $R^{3a}$, $R^{3b}$ and Y of each synthesized compound is defined in one row of table C.5 below.

The compounds were synthesized in analogy to Synthesis Example S.4.

Synthesis Example S.4

7-[5-(3,5-Dichloro-4-fluoro-phenyl)-4-fluoro-5-(trifluoromethyl)-4H-isoxazol-3-yl]-N-(2-pyridylmethyl) indane-4-carboxamide (Compound example 5-2; compound of formula C.5, wherein $R^{2a}$ and $R^{2c}$ are Cl, $R^{2b}$ is F, $R^{3a}$ is F and $R^{3b}$ is H, and —Y is —$NHCH_2$-(2-pyridyl))

Step 1: Methyl 7-[5-(3,5-dichloro-4-fluoro-phenyl)-4-fluoro-5-(trifluoromethyl)-4H-isoxazol-3-yl]indane-4-carboxylate (Compound Example 5-1)

To a solution of 7-[5-(3,5-dichloro-4-fluoro-phenyl)-5-(trifluoromethyl)-4H-isoxazol-3-yl]indane-4-carboxylate (compound example 1-1, 2 g) in THF (30 mL) under nitrogen at −78° C. was added), lithium hexamethyldisilazide ("LiHMDS", 4.6 mL, 1 M solution in THF) and the mixture was stirred for 1.5 h at −78° C. Then, N-fluorobenzenesulfonimide ("NFSI", 1.7 g) was added at −78° C. in one portion and the mixture was stirred at −78° C. for another 3 h. Then, the reaction was quenched with saturated aqueous $NH_4Cl$ solution. Ethyl acetate was added (300 mL) and the organic layer was washed with water (3×), dried ($Na_2SO_4$), filtered, and concentrated to afford a residue that was purified by flash chromatography on silica gel (ethyl acetate/cyclohexane) to afford the product (0.4 g, 19%).
$^1$H NMR (400 MHz, $CDCl_3$): δ 7.9 (d, 1H), 7.6 (m, 2H), 7.45 (d, 1H), 6.5 (d, 1H), 3.9 (s, 3H), 3.35 (m, 2H), 3.2 (m, 2H), 2.15 (m, 2H).

Step 2: 7-[5-(3,5-Dichloro-4-fluoro-phenyl)-4-fluoro-5-(trifluoromethyl)-4H-isoxazol-3-yl]indane-4-carboxylic acid The product of step 1 (0.4 g) in THF (7.5 mL) was treated with a solution of LiOH (0.08 g) in water (2.5 mL), and the mixture stirred at r.t. overnight. Then, diethyl ether (300 mL) was added and the pH of the solution was adjusted to pH 3-4 using 10% aqueous HCl solution. The organic layer was separated, washed with water (2×), dried ($Na_2SO_4$), filtered, and concentrated to afford the product (0.37 g, 95%), which was used in the next step without any further purification.

Step 3: 7-[5-(3,5-Dichloro-4-fluoro-phenyl)-4-fluoro-5-(trifluoromethyl)-4H-isoxazol-3-yl]-N-(2-pyridylmethyl)indane-4-carboxamide (Compound Example 5-2)

To a solution of the product of step 2 (0.36 g), 2-picolylamine (0.1 g, CAS 3731-51-9) and PyBroP (0.42 g) in $CH_2Cl_2$ (40 mL) at r.t. was added N,N-diisopropylethylamine (0.31 g). The reaction was stirred at r.t. overnight. Then, the reaction was quenched with water. The organic layer was separated, dried ($Na_2SO_4$), filtered and concentrated to give

TABLE C.5

| Ex. | $R^{2a}$, $R^{2b}$, $R^{2c}$ | $R^{3a}$, $R^{3b}$ | —Y | HPLC-MS: Method, $R_t$ (min) & $[M + H]^+$ or $^1$H-NMR | | |
|---|---|---|---|---|---|---|
| 5-1 | Cl, F, Cl | F, H | —$OCH_3$ | $^1$H NMR (400 MHz, $CDCl_3$): δ 7.9 (d, 1H), 7.6 (m, 2H), 7.45 (d, 1H), 6.5 (d, 1H), 3.9 (s, 3H), 3.35 (m, 2H), 3.2 (m, 2H), 2.15 (m, 2H) | | |
| 5-2 | Cl, F, Cl | F, H | —$NHCH_2$-(2-pyridyl) | A | 1.248 | 570.0 | a residue, which was purified by flash chromatography on silica gel to afford the product (0.29 g, 68%).

HPLC-MS (method A): 1.248 min, M=570.0.

C.6 Compound Examples 6

Compound example 6-1 corresponds to a compound of formula C.6:

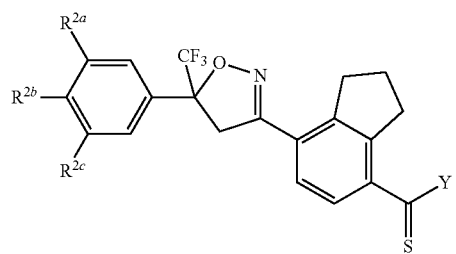

wherein $R^{2a}$, $R^{2b}$, $R^{2c}$ and Y of each synthesized compound is defined in one row of table C.6 below.

The compound was synthesized in analogy to Synthesis Example S.5.

TABLE C.6

| Ex. | $R^{2a}$, $R^{2b}$, $R^{2c}$ | —Y | HPLC-MS: Method, $R_t$ (min) & [M + H]$^+$ or $^1$H-NMR | | |
|---|---|---|---|---|---|
| 6-1 | Cl, H, Cl | —NHCH$_2$-(2-pyridyl) | A | 1.248 | 570.0 |

Synthesis Example S.5

7-[5-(3,5-dichlorophenyl)-5-(trifluoromethyl)-4H-isoxazol-3-yl]-N-(2-pyridylmethyl)indane-4-carbothioamide (Compound example 6-1; compound of formula C.5, wherein $R^{2a}$ and $R^{2c}$ are Cl, $R^{2b}$ is H, and —Y is —NHCH$_2$-(2-pyridyl))

A solution of 7-[5-(3,5-dichlorophenyl)-5-(trifluoromethyl)-4H-isoxazol-3-yl]-N-(2-pyridylmethyl)indane-4-carboxamide (compound example 1-27, 190 mg) and Lawesson's reagent (90 mg, CAS 19172-47-5) in toluene (15 mL) was refluxed for 5 h and then stirred at r.t. overnight. Ethyl acetate was added (200 mL) and the organic layer was washed with water (3×), dried (Na$_2$SO$_4$), filtered and concentrated to give a residue, which was purified by flash chromatography on silica gel to afford the product (70 mg, 60%).

HPLC-MS (method A): 1.335 min, M=550.0.

II. Evaluation of Pesticidal Activity

The activity of the compounds of formula I of the present invention can be demonstrated and evaluated by the following biological test.

B.1 Diamond back moth (*Plutella xylostella*)

The active compound was dissolved at the desired concentration in a mixture of 1:1 (vol:vol) distilled water:acetone. Surfactant (Kinetic HV) was added at a rate of 0.01% (vol/vol). The test solution was prepared at the day of use.

Leaves of cabbage were dipped in test solution and air-dried. Treated leaves were placed in petri dishes lined with moist filter paper and inoculated with ten 3$^{rd}$ instar larvae. Mortality was recorded 72 hours after treatment.

In this test, the compounds 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 2-1, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 4-1, 4-2 at 300 ppm, respectively, showed a mortality of at least 75% in comparison with untreated controls.

B.2 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 1-73, 1-74, 1-75, 1-76, 1-77, 1-78, 1-79, 1-80, 1-82, 2-1, 2-2, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 3-7, 3-8, 3-9, 3-10, 3-11, 3-12, 3-13, 4-1, 4-2 at 2500 ppm, respectively, showed a mortality of at least 75% in comparison with untreated controls.

B.3 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 1-73, 1-74, 1-75, 1-76, 1-77, 1-78, 1-79, 1-80, 1-82, 2-2, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 3-7, 3-8, 3-9, 3-10, 3-11, 3-12, 3-13, 4-1, 4-2 at 2500 ppm, respectively, showed a mortality of at least 75% in comparison with untreated controls.

B.4 Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-82, 2-1, 2-2, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 3-7, 3-8, 3-9, 3-10, 3-11, 3-12, 3-13, 4-1, 4-2 at 2500 ppm, respectively, showed a mortality of at least 75% in comparison with untreated controls.

B.5 Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25±1° C. and about 75±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 1-73, 1-74, 1-75, 1-76, 1-77, 1-78, 1-79, 1-80, 1-81, 1-82, 2-1, 2-2, 2-3, 2-4, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 3-2, 3-3, 3-4, 3-5, 3-6, 3-7, 3-8, 3-9, 3-10, 3-11, 3-12, 3-13, 4-1, 4-2 at 2500 ppm, respectively, showed a mortality of at least 75% in comparison with untreated controls.

B.6 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-3, 1-4, 1-5, 1-6, 1-7, 1-8, 1-9, 1-10, 1-11, 1-12, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 1-73, 1-74, 1-75, 1-76, 1-77, 1-78, 1-79, 1-80, 1-82, 2-3, 2-4, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 3-3, 3-4, 3-5, 3-6, 3-7, 3-8, 3-9, 3-10, 3-11, 3-12, 3-13, 4-1, 4-2 at 2500 ppm showed a mortality of at least 75% in comparison with untreated controls.

B.7 Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, the compounds 1-1, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-68, 1-69, 1-70, 1-71, 1-72, 2-2, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 4-1, 4-2 at 300 ppm, respectively, showed a mortality of at least 75% in comparison with untreated controls.

B.8 Rice Green Leafhopper (*Nephotettix virescens*)

Rice seedlings were cleaned and washed 24 hours before spraying. The active compounds were formulated in 1:1 acetone:water (vol:vol), and 0.01% vol/vol surfactant (Kinetic HV) was added. Potted rice seedlings were sprayed with 5-6 ml test solution, air dried, covered with Mylar cages and inoculated with 10 adults.

Treated rice plants were kept at about 28-29° C. and relative humidity of about 50-60%. Percent mortality was recorded after 72 hours.

In this test, the compounds 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-25, 1-26, 1-27, 1-28, 1-29, 1-30, 1-31, 1-32, 1-33, 1-34, 1-35, 1-36, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 2-3, 2-4, 2-5, 2-6, 2-7, 2-8, 2-9, 2-10, 2-11, 2-12, 2-13, 2-14, 2-17, 2-18, 2-19, 2-20, 2-21, 2-23, 2-24, 3-3, 3-4, 3-5, 3-6, 4-2 at 300 ppm, respectively, showed a mortality of at least 75% in comparison with untreated controls.

B.9 Red Spider Mite (*Tetranychus kanzawai*)

The active compound was dissolved at the desired concentration in a mixture of 1:1 (vol:vol) distilled water: acetone. Add surfactant (Kinetic HV) was added at a rate of 0.01% (vol/vol). The test solution was prepared at the day of use.

Potted cowpea beans of 4-5 days of age were cleaned with tap water and sprayed with 1-2 ml of the test solution using air driven hand atomizer. The treated plants were allowed to air dry and afterwards inoculated with 30 or more mites by clipping a cassava leaf section from rearing population. Treated plants were placed inside a holding room at about 25-27° C. and about 50-60% relative humidity. Percent mortality was assessed 72 hours after treatment.

In this test, the compounds 1-3, 1-4, 1-5, 1-6, 1-7, 1-8, 1-9, 1-10, 1-11, 1-12, 1-13, 1-14, 1-18, 1-20, 1-21, 1-22, 1-23, 1-26, 1-27, 1-28, 1-29, 1-30, 1-31, 1-32, 1-33, 1-34, 1-35, 1-36, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-57, 1-58, 1-59, 1-60, 1-61, 1-62, 1-63, 1-64, 1-65, 1-66, 1-67, 1-69, 1-70, 1-71, 1-72, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 3-5, 3-6, 4-2 at 300 ppm showed a mortality of at least 75% in comparison with untreated controls.

B.10 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-5, 1-6, 1-7, 1-10, 1-12, 1-14, 1-16, 1-17, 1-21, 1-23, 1-25, 1-26, 1-27, 1-28, 1-29, 1-30, 1-31, 1-32, 1-33, 1-34, 1-38, 1-42, 1-49, 1-51, 2-3, 2-4, 2-5, 2-6, 2-7, 2-8, 2-9, 2-10, 2-11, 2-12, 2-13, 2-14, 4-2 at 1 ppm showed a mortality of at least 75% in comparison with untreated controls.

B.11 Green Soldier Stink Bug (*Nezara viridula*)

The active compound was dissolved at the desired concentration in a mixture of 1:1 (vol:vol) distilled water: acetone. Surfactant (Kinetic HV) was added at a rate of 0.01% (vol/vol). The test solution was prepared at the day of use.

Soybean pods were placed in glass Petri dishes lined with moist filter paper and inoculated with ten late 3rd instar *N. viridula*. Using a hand atomizer, approximately 2 ml solution is sprayed into each Petri dish. Assay arenas were kept at about 25° C. Percent mortality was recorded after 5 days.

In this test, the compounds 1-3, 1-4, 1-5, 1-6, 1-7, 1-8, 1-9, 1-10, 1-11, 1-12, 1-13, 1-14, 1-15, 1-16, 1-17, 1-18, 1-20, 1-21, 1-22, 1-23, 1-25, 1-26, 1-27, 1-28, 1-29, 1-3, 1-30, 1-31, 1-32, 1-33, 1-34, 1-35, 1-36, 1-38, 1-39, 1-40, 1-41, 1-42, 1-44, 1-45, 1-46, 1-47, 1-48, 1-49, 1-50, 1-51, 1-53, 1-54, 1-55, 1-57, 1-58, 1-59, 1-60, 1-61, 1-62, 1-63, 1-64, 1-65, 1-66, 1-67, 1-72, 2-3, 2-4, 2-5, 2-6, 2-7, 2-8, 2-9, 2-10, 2-11, 2-12, 2-13, 2-14, 2-17, 2-18, 2-19, 2-20, 2-21, 2-22, 2-23, 2-24, 3-3, 3-4, 4-2 at 300 ppm showed a mortality of at least 75% in comparison with untreated controls.

B.12 Neotropical Brown Stink Bug (*Euschistus heros*)

The active compound was dissolved at the desired concentration in a mixture of 1:1 (vol:vol) distilled water: acetone. Surfactant (Kinetic HV) was added at a rate of 0.01% (vol/vol). The test solution was prepared at the day of use.

Soybean pods were placed in microwavable plastic cups and inoculated with ten adult stage *E. heros*. Using a hand atomizer, approximately 1 ml solution is sprayed into each cup, insects and food present. A water source was provided (cotton wick with water). Each treatment was replicated 2-fold. Assay arenas were kept at about 25° C. Percent mortality was recorded after 5 days.

In this test, the compounds 1-3, 1-4, 1-5, 1-6, 1-7, 1-8, 1-9, 1-10, 1-11, 1-12, 1-13, 1-14, 1-17, 1-18, 1-20, 1-21, 1-23, 1-25, 1-26, 1-27, 1-28, 1-30, 1-31, 1-32, 1-33, 2-3, 2-4, 2-6, 2-7, 2-8, 2-9, 2-10, 2-11 at 100 ppm showed a mortality of at least 75% in comparison with untreated controls.

B.13 Brown Marmorated Stink Bug (*Halyomorpha halys*)

The active compound was dissolved at the desired concentration in a mixture of 1:1 (vol:vol) distilled water: acetone. Surfactant (Kinetic HV) was added at a rate of 0.01% (vol/vol). The test solution was prepared at the day of use.

Row peanuts and soybean seeds were placed into microwavable plastic cups and inoculated with five adult stage *H. halys*. Using a hand atomizer, approximately 1 ml solution is sprayed into each cup, insects and food present. A water source was provided (cotton wick with water). Each treatment is replicated 4-fold. Assay arenas are kept at about 25° C. Percent mortality was recorded after 5 days.

In this test, the compounds 1-3, 1-4, 1-5, 1-6, 1-7, 1-9, 1-11, 1-12, 1-14, 1-16, 1-20, 1-21, 1-25, 1-26, 1-27, 1-28, 1-30, 1-31, 1-32, 1-33, 2-3, 2-4, 2-5, 2-6, 2-7, 2-8, 2-9, 2-10 at 100 ppm showed a mortality of at least 75% in comparison with untreated controls.

We claim:

1. An azoline compound of the formula I

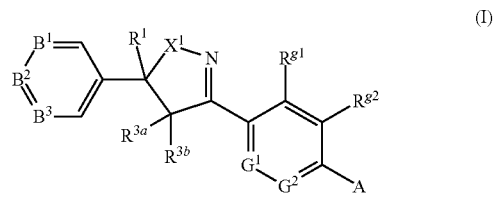

(I)

wherein
$X^1$ is O or $CH_2$;
A is a group of following formula:

(A)

wherein
# denotes the bond to the aromatic ring of formula (I);
W is selected from O and S;
Y is selected from hydrogen, —N(R⁵)R⁶ and —OR⁹;
B¹, B² and B³ are each independently CR²;
G¹ and G² are each independently CR⁴;
R^{g1} and R^{g2} form together a bridging group selected from —CH₂CH₂CH₂CH₂— and —CH₂CH₂CH₂—;
R¹ is CF₃;
each R² is independently selected from the group consisting of hydrogen, halogen, C₁-C₂-haloalkoxy and C₁-C₂-haloalkyl;
R^{3a}, R^{3b} are each independently selected from the group consisting of hydrogen, halogen, hydroxyl, —CO₂R^{3d}, C₂-C₃-alkenyl, C₂-C₃-alkynyl, C₁-C₃-alkoxy, C₁-C₃-haloalkoxy, C₁-C₃-haloalkylthio, C₁-C₃-alkylsulfonyl and C₁-C₃-haloalkylsulfonyl; or
R^{3a} and R^{3b} together form a group =O, =C(R^{3c})₂, =NOH or =NOCH₃;
each R^{3c} is independently selected from the group consisting of hydrogen, halogen, CH₃ and CF₃;
R^{3d} is selected from the group consisting of hydrogen, C₁-C₆-alkyl and C₁-C₃-alkyloxy-C₁-C₃-alkyl-;
each R⁴ is independently selected from the group consisting of hydrogen, halogen and cyano;
R⁵ selected from hydrogen, C₁-C₆-alkyl, C₂-C₃-alkynyl and CH₂—CN;
R⁶ is selected from hydrogen, C₁-C₆-alkyl, C₁-C₄-alkyl which carries one radical R⁸, C₂-C₆-alkenyl, C₂-C₆-haloalkenyl, C₂-C₆-alkynyl, C₃-C₆-cycloalkyl which may be substituted by 1 or 2 substituents selected from F, CN and pyridyl;

—N(R^{101a})R^{101b}, wherein
R^{101a} is selected from hydrogen and C₁-C₆-alkyl; and
R^{101b} is selected from hydrogen, —C(=O)N(R^{14a})R^{14b}, wherein
R^{14a} is selected from the group consisting of hydrogen and C₁-C₆-alkyl; and
R^{14b} is selected from the group consisting of hydrogen, C₁-C₆-alkyl, C₂-C₄-alkynyl, CH₂—CN, C₁-C₆-haloalkyl, C₃-C₆-cycloalkyl, C₃-C₆-halocycloalkyl, C₁-C₄-alkoxy and C₁-C₄-haloalkoxy;
phenyl, optionally substituted with 1, 2, 3, 4 or 5 substituents R¹⁶, and a heterocyclic ring selected from rings of formulae E-1 to E-42

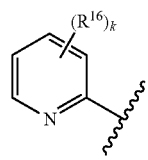

E-1

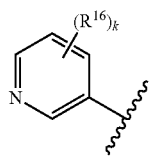

E-2

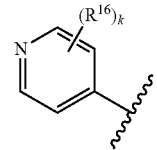

E-3

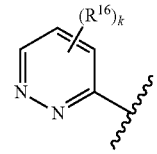

E-4

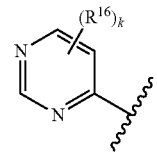

E-5

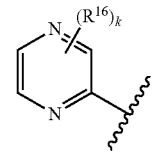

E-6

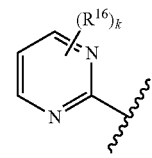

E-7

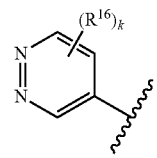

E-8

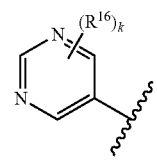

E-9

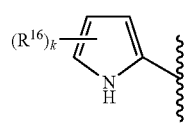

E-10

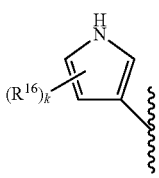

E-11

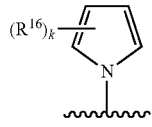

E-12

-continued

| | |
|---|---|
| E-13 (R¹⁶)ₖ-thiophen-2-yl | |
| E-14 (R¹⁶)ₖ-thiophen-3-yl | |
| E-15 (R¹⁶)ₖ-furan-2-yl | |
| E-16 (R¹⁶)ₖ-furan-3-yl | |
| E-17 (R¹⁶)ₖ-isoxazol-5-yl | |
| E-18 (R¹⁶)ₖ-isoxazol-4-yl | |
| E-19 (R¹⁶)ₖ-isoxazol-3-yl | |
| E-20 (R¹⁶)ₖ-isothiazol-5-yl | |
| E-21 (R¹⁶)ₖ-isothiazol-4-yl | |
| E-22 (R¹⁶)ₖ-isothiazol-3-yl | |
| E-23 (R¹⁶)ₖ-pyrazol-5-yl | |
| E-24 (R¹⁶)ₖ-pyrazol-4-yl | |
| E-25 (R¹⁶)ₖ-pyrazol-3-yl | |
| E-26 (R¹⁶)ₖ-oxazol-5-yl | |
| E-27 (R¹⁶)ₖ-oxazol-4-yl | |
| E-28 (R¹⁶)ₖ-oxazol-2-yl | |
| E-29 (R¹⁶)ₖ-thiazol-5-yl | |
| E-30 (R¹⁶)ₖ-thiazol-4-yl | |
| E-31 (R¹⁶)ₖ-thiazol-2-yl | |
| E-32 (R¹⁶)ₖ-imidazol-5-yl | |
| E-33 (R¹⁶)ₖ-imidazol-4-yl | |
| E-34 (R¹⁶)ₖ-imidazol-2-yl | |

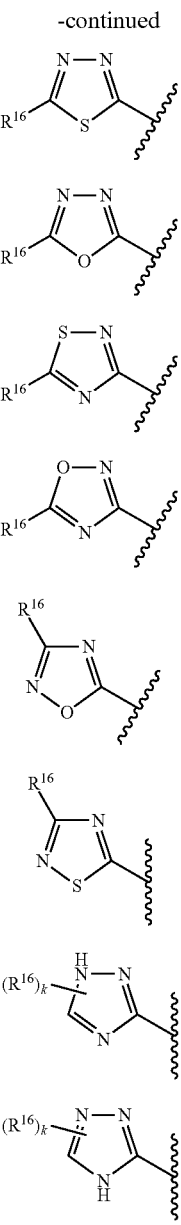

E-35

E-36

E-37

E-38

E-39

E-40

E-41

E-42 where in these rings E-1 to E-42 as a meaning for $R^{101b}$
the zigzag line denotes the attachment point to the remainder of the molecule;

k is 0, 1, 2 or 3, and each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl;

—CH═NOR$^{9a}$, wherein $R^{9a}$ is selected from hydrogen, $C_1$-$C_6$-alkyl and $C_1$-$C_6$-haloalkyl;

phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;

wherein each $R^{11}$ is independently selected from the group consisting of halogen, cyano, nitro, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated heterocyclic ring may form together ═O or ═S; or two $R^{11}$ present on the same S or SO ring member of a heterocyclic ring may together form a group ═N($C_1$-$C_6$-alkyl), ═NO($C_1$-$C_6$-alkyl), ═NN(H)($C_1$-$C_6$-alkyl) or ═NN($C_1$-$C_6$-alkyl)$_2$;

each $R^8$ is independently selected from OH, CN, $C_3$-$C_8$-cycloalkyl which optionally carries a CN or a $C_1$-$C_2$-haloalkyl substituent; $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(═O)N($R^{102a}$)$R^{102b}$, phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2, 3 or 4 heteroatoms or heteroatom groups independently selected from N, O, S, NO, SO and $SO_2$, as ring members, where the heteromonocyclic ring may be substituted with one or more substituents $R^{16}$;

wherein $R^{102a}$ is selected from the group consisting of hydrogen, $C_1$-$C_6$-alkyl, $C_2$-$C_3$-alkynyl and $CH_2$—CN;

$R^{102b}$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_6$-alkoxy, $C_1$-$C_6$-haloalkoxy, phenyl which is optionally substituted with 1, 2, 3, 4 or 5 substituents selected from the group consisting of halogen, cyano, nitro, $C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-42 as defined above and E-43 to E-57:

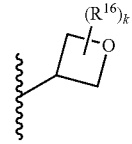

E-43

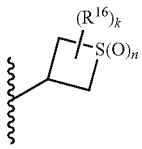

E-44

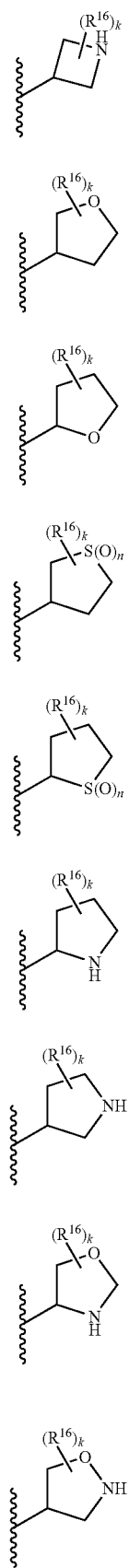

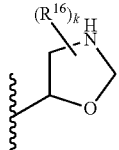
E-54

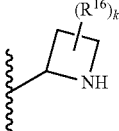
E-55

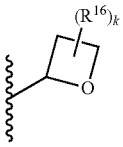
E-56

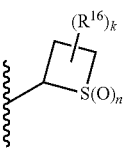
E-57 where in these rings E-43 to E-57
the zigzag line denotes the attachment point to the remainder of the molecule;
k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or
two $R^{16}$ present on the same carbon atom of a saturated ring may form together =O or =S; and
each $R^{16}$ as a substituent on phenyl (as a meaning of $R^8$) or the heterocyclic rings (as a meaning of $R^8$) is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated heterocyclic ring may form together =O or =S; or
two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;
or
$R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

or $R^5$ and $R^6$ together form a group =$S(R^{9b})_2$, where $R^{9b}$ is selected from $C_1$-$C_6$-alkyl and $C_1$-$C_6$-haloalkyl;

$R^9$ is selected from the group consisting of hydrogen, $C_1$-$C_6$-alkyl, $C_1$-$C_6$-haloalkyl and $C_1$-$C_6$-alkyl substituted by one radical $R^{13}$; where $R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-57 as defined above;

where in these rings E-1 to E-57 as a meaning of $R^{13}$ the zigzag line denotes the attachment point to the remainder of the molecule;

k is 0, 1, 2 or 3, n is 0, 1 or 2; and each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)amino-carbonyl; or two $R^{16}$ present on the same carbon atom of a saturated ring may form together =O or =S; and each $R^{16}$ in all other cases is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;

$C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl; or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or or two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-alkoxy and $C_1$-$C_4$-haloalkoxy;

and the N-oxides, stereoisomers and agriculturally or veterinarily acceptable salts thereof.

2. The compound as claimed in claim 1, where each $R^8$ is independently selected from OH, CN, $C_3$-$C_8$-cycloalkyl which optionally carries a CN or $CF_3$ substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{16}$; where $R^{102a}$, $R^{102b}$ and $R^{16}$ are as defined in claim 1.

3. The compound as claimed in claim 1, where $X^1$ is O.

4. The compound as claimed in claim 1, where $X^1$ is $CH_2$.

5. The compound as claimed in claim 1, where W is O.

6. The compound as claimed in claim 1, where in A Y is —$OR^9$.

7. The compound as claimed in claim 1, where in A Y is —N($R^5$)$R^6$; wherein $R^5$ and $R^6$ are as defined in claim 1.

8. The compound as claimed in claim 7, where $R^5$ is hydrogen or $C_1$-$C_3$-alkyl;

$R^6$ is selected from hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;

—N($R^{101a}$)$R^{101b}$, wherein $R^{101a}$ is selected from hydrogen and $C_1$-$C_6$-alkyl; and $R^{101b}$ is selected from hydrogen, —C(=O)N($R^{14a}$)$R^{14b}$, wherein $R^{14a}$ is selected from the group consisting of hydrogen and $C_1$-$C_6$-alkyl; and $R^{14b}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy;

phenyl, optionally substituted with 1, 2, 3, 4 or 5 substituents wherein $R^{16}$ is as defined below; and a heteroaromatic ring selected from rings of formulae E-1 to E-42 as defined in claim 1;

—CH=NOR$^{9a}$, wherein $R^{9a}$ is selected from hydrogen, $C_1$-$C_6$-alkyl and $C_1$-$C_6$-haloalkyl;

phenyl which may be substituted with 1, 2, 3, 4, or 5 substituents $R^{11}$, wherein $R^{11}$ is as defined below; and a heteromonocyclic ring selected from rings of formulae F-1 to F-60

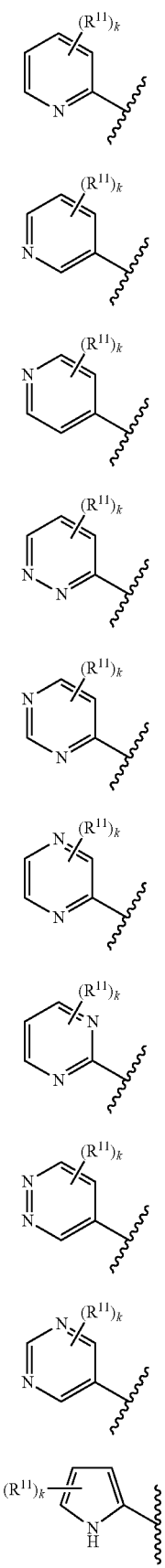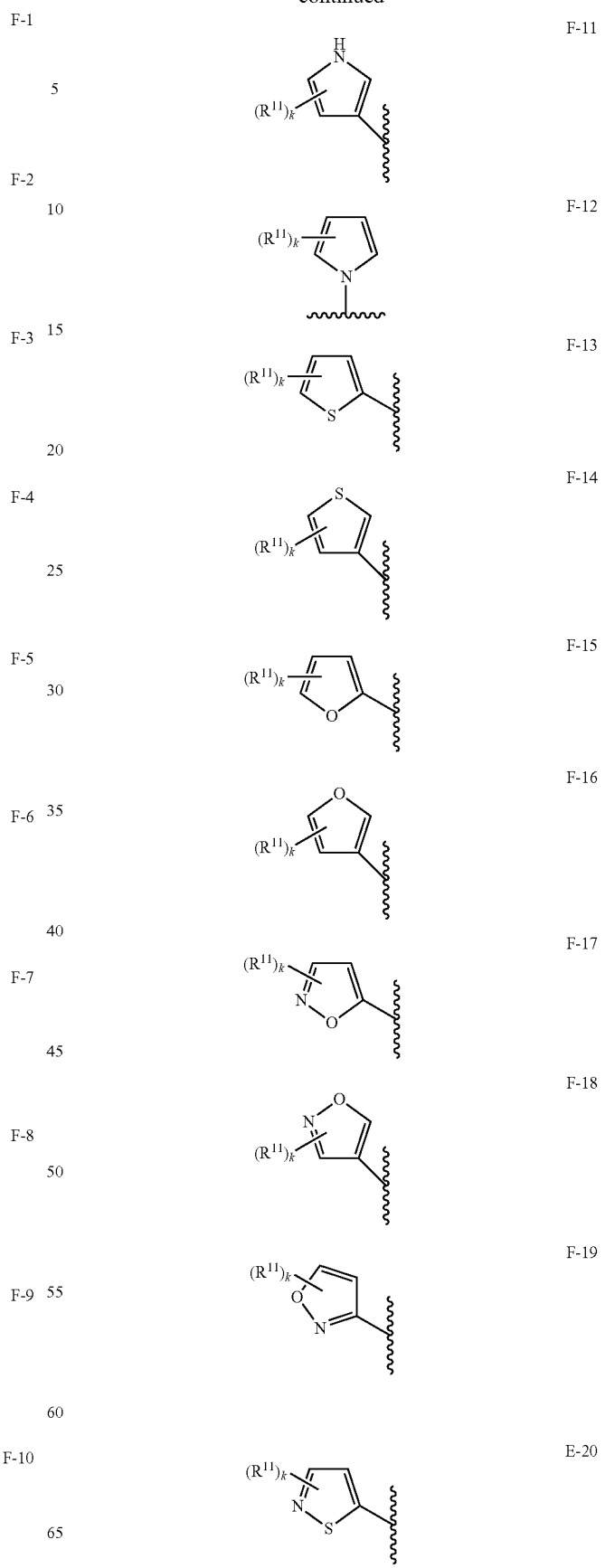

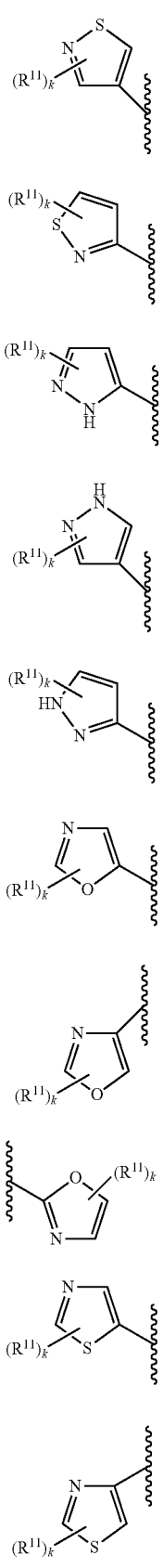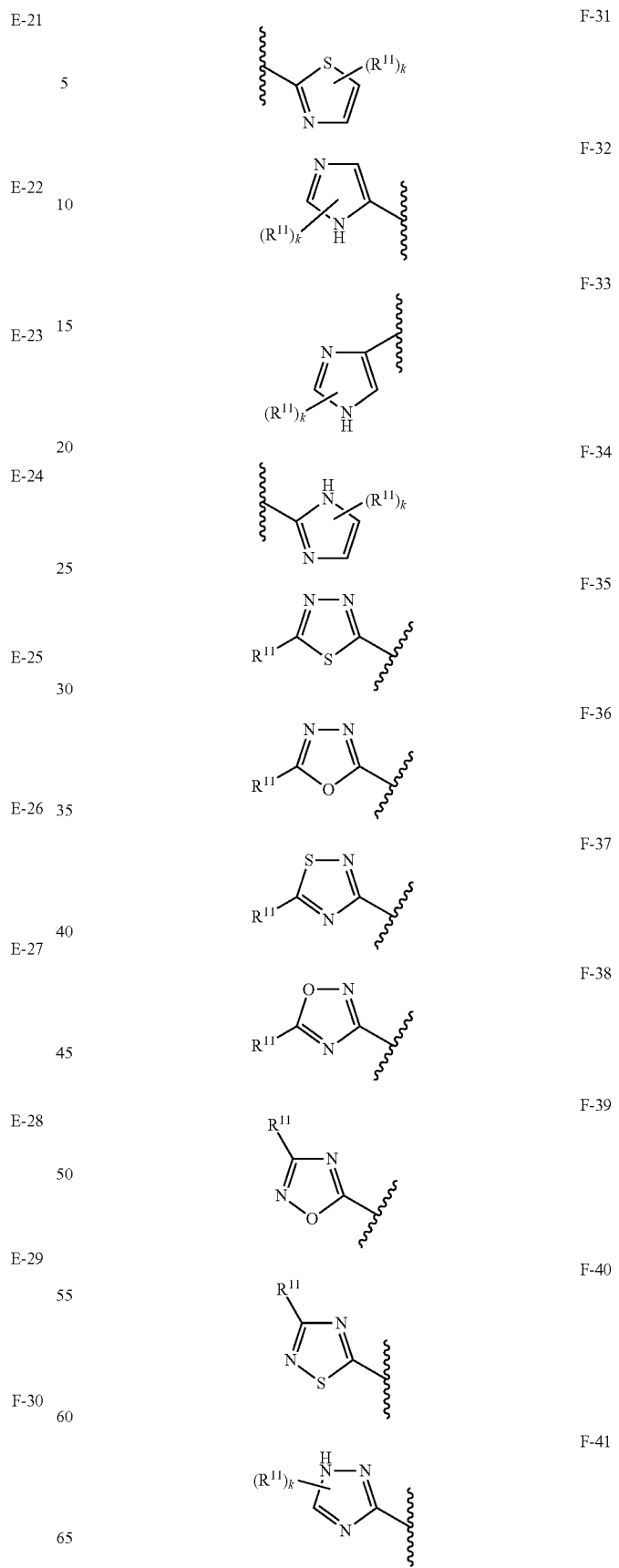

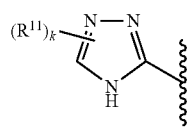 F-42
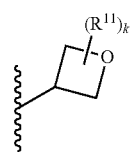 F-43
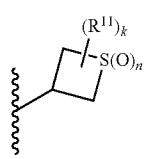 F-44
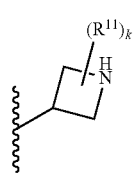 F-45
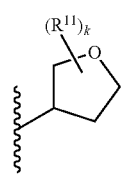 F-46
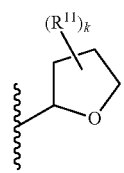 F-47
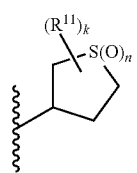 F-48
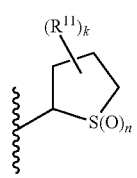 F-49
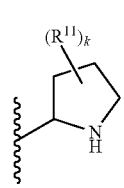 F-50
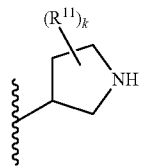 F-51
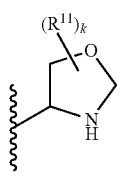 F-52
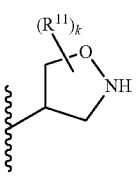 F-53
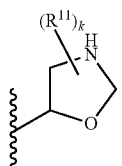 F-54
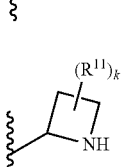 F-55
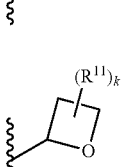 F-56
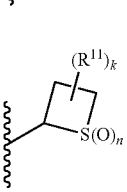 F-57
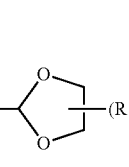 F-58
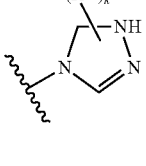 F-59

-continued

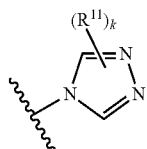
F-60 wherein
the zigzag line denotes the attachment point to the remainder of the molecule;
k is 0, 1, 2 or 3,
n is 0, 1 or 2, and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{11}$ present on the same carbon atom of a saturated or partially unsaturated heterocyclic ring may form together =O or =S; or
two $R^{11}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

$R^8$ is selected from OH, CN, $C_3$-$C_8$-cycloalkyl which optionally carries a CN, $CHF_2$ or $CF_3$ substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a heterocyclic ring selected from rings of formulae E-1 to E-57 as defined in claim 1 and additionally from 1,3-dioxolan-2-yl which may carry 1, 2 or 3 substituents $R^{16}$ as defined in claim 1;
wherein
$R^{102a}$ is selected from the group consisting of hydrogen and $C_1$-$C_6$-alkyl;
$R^{102b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_6$-alkoxy and $C_1$-$C_6$-haloalkoxy; and
each $R^{16}$ as a substituent on phenyl or heterocyclic rings of formulae E-1 to E-57 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{16}$ present on the same carbon atom of a saturated heterocyclic ring may form together =O or =S; or
two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$.

9. The compound as claimed in claim 8, where
$R^5$ is as defined in claim 8;
$R^6$ is selected from hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;
—N($R^{101a}$)$R^{101b}$, wherein $R^{101a}$ and $R^{101b}$ are as defined in claim 8;
—CH=NOR$^{9a}$, wherein $R^{9a}$ is as defined in claim 8;
phenyl which may be substituted with 1, 2, 3, 4, or 5 substituents $R^{11}$, wherein $R^{11}$ is as defined below;
and a heteromonocyclic ring selected from rings of formulae F-1 to F-57 as defined in claim 8; wherein
$R^8$ is selected from OH, CN, $C_3$-$C_8$-cycloalkyl which optionally carries a CN or $CF_3$ substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{102a}$)$R^{102b}$, phenyl, optionally substituted with 1, 2, 3, 4 or 5 substituents $R^{16}$, and a heterocyclic ring selected from rings of formulae E-1 to E-57 as defined in claim 1;
wherein $R^{102a}$, $R^{102b}$, and $R^{16}$ are as defined in claim 8; and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{11}$ present on the same carbon atom of a saturated heterocyclic ring may form together =O or =S; or
two $R^{11}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$.

10. The compound as claimed in claim 1, where the saturated heteromonocyclic ring $R^6$ is selected from rings of formulae F-44-1 and F-53-1, and the heterocyclic ring $R^8$ is selected from rings of formulae E-44-1 and E-57-1

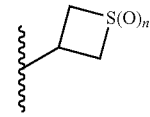
F-44-1

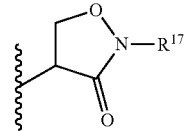
F-53-1

-continued

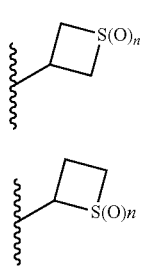

E-44-1

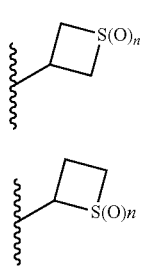

E-57-1 wherein
n is 0, 1 or 2; and
R$^{17}$ is selected from the group consisting of hydrogen, C$_1$-C$_4$-alkyl, C$_1$-C$_4$-haloalkyl, C$_3$-C$_6$-cycloalkyl, C$_3$-C$_6$-halocycloalkyl, C$_2$-C$_4$-alkenyl, C$_2$-C$_4$-haloalkenyl, C$_2$-C$_4$-alkynyl, C$_2$-C$_4$-haloalkynyl and CH$_2$—(C$_3$-C$_6$-cycloalkyl).

11. The compound as claimed in claim 1, where B$^1$ is CR$^2$, where R$^2$ is not hydrogen, and B$^2$ and B$^3$ are CR$^2$, where R$^2$ is selected from hydrogen, F, Cl, Br, OCF$_3$ and CF$_3$.

12. The compounds as claimed in claim 1, where R$^4$ is hydrogen.

13. The compound as claimed in claim 1, where R$^{g1}$ and R$^{g2}$ form together a bridging group —CH$_2$—CH$_2$—CH$_2$—.

14. The compound as claimed in claim 1, where R$^{g1}$ and R$^{g2}$ form together a bridging group —CH$_2$—CH$_2$—CH$_2$—CH$_2$—.

15. The compound as claimed in claim 1, where R$^{3a}$ and R$^{3b}$ are hydrogen or fluorine.

16. The compound as claimed in claim 1, of formula IB

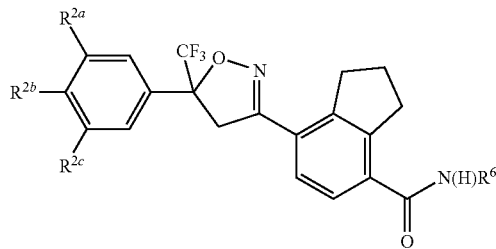

IB wherein R$^{2a}$ is Cl, R$^{2b}$ is F, R$^{2c}$ is Cl, and
R$^6$ is CH$_2$—C(O)—N(H)—R$^{102b}$, wherein
R$^{102b}$ is selected from the group consisting of C$_1$-C$_4$-alkyl, C$_2$-C$_4$-alkyl substituted with 1 or 2 fluorine atoms, C$_2$-C$_4$-alkenyl, C$_2$-C$_4$-alkynyl, CH$_2$—CN, C$_3$-C$_6$-cycloalkyl, C$_3$-C$_6$-halocycloalkyl and C$_3$-C$_6$-cycloalkylmethyl;
and the stereoisomers and agriculturally or veterinarily acceptable salts thereof.

17. The compound as claimed in claim 1, of formula IB as defined in claim 16, wherein R$^{2a}$ is Cl, R$^{2b}$ is F, R$^{2c}$ is Cl, and R$^6$ is —CH$_2$—R$^8$, wherein
R$^8$ is selected from rings E-5, E-6, E-7, E-19, E-25, E-27, E-44-1 and E-57-1 as defined in claim 1, where the rings E-5, E-6, E-7, E-19 and E-27 are unsubstituted (k is 0) or carry 1 or 2 substituents R$^{16}$ (k is 1 or 2), wherein
each R$^{16}$ is independently selected from halogen, cyano, nitro, C$_1$-C$_2$-alkyl, C$_1$-C$_2$-haloalkyl, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylsulfinyl, C$_1$-C$_2$-haloalkylsulfinyl, C$_1$-C$_2$-alkylsulfonyl, C$_1$-C$_2$-haloalkylsulfonyl, C$_3$-C$_4$-cycloalkyl, C$_3$-C$_4$-halocycloalkyl, C$_2$-C$_3$-alkenyl, C$_2$-C$_3$-alkynyl; and
where ring E-25 carries one substituent R$^{16}$ on the nitrogen atom in the 1-position and optionally carries 1 or 2 further substituents R$^{16}$, where R$^{16}$ is as defined above; where however R$^{16}$ bound in the 1-position is not is not halogen, cyano, nitro, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylsulfinyl, C$_1$-C$_2$-haloalkylsulfinyl, C$_1$-C$_2$-alkylsulfonyl or C$_1$-C$_2$-haloalkylsulfonyl;
and the stereoisomers and agriculturally or veterinarily acceptable salts thereof.

18. The compound as claimed in claim 1, of formula IB as defined in claim 16, wherein R$^{2a}$ is Cl, R$^{2b}$ is F, R$^{2c}$ is Cl, and R$^6$ is selected from rings F-2, F-4, F-6, F-8, F-9, F-44-1, F-46, F-51 and F-53-1 as defined in claim 8, where the rings F-2, F-4, F-6, F-8, F-9 and F-46 are unsubstituted (k is 0) or carry 1 or 2 substituents R$^{11}$ (k is 1 or 2), wherein
each R$^{11}$ is independently selected from halogen, cyano, nitro, C$_1$-C$_2$-alkyl, C$_1$-C$_2$-alkoxy, C$_1$-C$_2$-haloalkoxy, C$_1$-C$_2$-haloalkylthio, C$_1$-C$_2$-alkylsulfonyl, C$_1$-C$_2$-haloalkylsulfonyl, C$_3$-C$_4$-cycloalkyl, C$_3$-C$_4$-halocycloalkyl, C$_2$-C$_3$-alkenyl and C$_2$-C$_3$-alkynyl; and
where ring F-51 is a ring of formula F-51-1

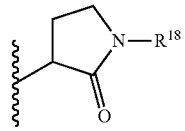

F-51-1 wherein
R$^{18}$ is selected from the group consisting of hydrogen, C$_1$-C$_2$-alkyl, C$_3$-C$_4$-cycloalkyl, C$_3$-C$_4$-halocycloalkyl, C$_2$-C$_3$-alkenyl and C$_2$-C$_3$-alkynyl;
and the stereoisomers and agriculturally or veterinarily acceptable salts thereof.

19. The compound as claimed in claim 1, of formula IB as defined in claim 16, wherein R$^{2a}$ is Cl, R$^{2b}$ is F, R$^{2c}$ is Cl, and R$^6$ is selected from C$_2$-C$_4$-alkyl which may be substituted with 1 or 2 fluorine atoms, cyclopropyl, C$_3$-C$_5$-halocycloalkyl, CH$_2$—(C$_3$-C$_5$-halocycloalkyl), CH$_2$-(1-cyano-(C$_3$-C$_5$-cycloalkyl)), C$_2$-C$_4$-alkenyl, C$_2$-C$_4$-alkynyl, CH$_2$—CN and —CH=NOR$^{9a}$, wherein R$^{9a}$ is selected from C$_1$-C$_3$-alkyl and C$_1$-C$_3$-haloalkyl;
and the stereoisomers and agriculturally or veterinarily acceptable salts thereof.

20. The compound as claimed in claim 1, of formula IB as defined in claim 16, wherein R$^{2a}$ is Cl, R$^{2b}$ is F, R$^{2c}$ is Cl, and R$^6$ is N(H)R$^{101b}$, wherein
R$^{101b}$ is selected from —C(O)—N(H)R$^{14b}$ and rings E-1 and E-7 as defined in claim 1, where
R$^{14b}$ is selected from C$_1$-C$_3$-alkyl, C$_1$-C$_3$-haloalkyl and cyclopropyl; and
where in rings E-1 and E-7
k is 0, 1 or 2; and
each R$^{16}$ is independently selected from halogen, cyano, nitro, C$_1$-C$_2$-alkyl, C$_1$-C$_2$-haloalkyl, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylsulfinyl, C$_1$-C$_2$-haloalkylsulfinyl, C$_1$-C$_2$-alkylsulfonyl, C$_1$-C$_2$- haloalkylsulfonyl, $C_3$-$C_4$-cycloalkyl, $C_3$-$C_4$-halocycloalkyl, $C_2$-$C_3$-alkenyl, $C_2$-$C_3$-alkynyl;

and the stereoisomers and agriculturally or veterinarily acceptable salts thereof.

21. An agricultural or veterinary composition comprising at least one compound of the formula I, as defined in claim 1, a stereoisomer thereof and/or at least one agriculturally or veterinarily acceptable salt thereof, and at least one inert liquid and/or solid agriculturally or veterinarily acceptable carrier.

22. A method for controlling invertebrate pests which method comprises treating the pests, their food supply, their habitat or their breeding ground or a cultivated plant, plant propagation materials, soil, area, material or environment in which the pests are growing or may grow, or the materials, cultivated plants, plant propagation materials, soils, surfaces or spaces to be protected from pest attack or infestation with a pesticidally effective amount of a compound of claim 1 or stereoisomer and/or an agriculturally acceptable salt thereof.

23. A method for protecting plant propagation material and/or the plants which grow therefrom from attack or infestation by invertebrate pests, which method comprises treating the plant propagation material with a pesticidally effective amount of at least one compound of the formula I as defined in claim 1, a stereoisomer and/or at least one agriculturally acceptable salt thereof.

\* \* \* \* \*